US011021716B2

(12) United States Patent
Altier et al.

(10) Patent No.: US 11,021,716 B2
(45) Date of Patent: Jun. 1, 2021

(54) INSECTICIDAL PROTEINS AND METHODS FOR THEIR USE

(71) Applicant: PIONEER HI-BRED INTERNATIONAL, INC., Johnston, IA (US)

(72) Inventors: Daniel J Altier, Granger, IA (US); Jennifer Kara Barry, Ames, IA (US); Ryan Michael Gerber, Apex, NC (US); Steven D Gruver, Pacifica, CA (US); Lu Liu, Palo Alto, CA (US); Ute Schellenberger, Palo Alto, CA (US); Jun-Zhi Wei, Hayward, CA (US); Weiping Xie, East Palo Alto, CA (US); Nasser Yalpani, Kelowna (CA); Genhai Zhu, San Jose, CA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/345,764

(22) PCT Filed: Sep. 14, 2017

(86) PCT No.: PCT/US2017/051460
§ 371 (c)(1),
(2) Date: Apr. 29, 2019

(87) PCT Pub. No.: WO2018/084936
PCT Pub. Date: May 11, 2018

(65) Prior Publication Data

US 2020/0055906 A1 Feb. 20, 2020

Related U.S. Application Data

(60) Provisional application No. 62/415,781, filed on Nov. 1, 2016.

(51) Int. Cl.

| | |
|---|---|
| ***C12N 15/82*** | (2006.01) |
| ***C07K 14/21*** | (2006.01) |
| ***C07K 14/265*** | (2006.01) |
| ***C07K 14/32*** | (2006.01) |
| ***C07K 14/33*** | (2006.01) |
| ***A01N 37/46*** | (2006.01) |

(52) U.S. Cl.
CPC ......... *C12N 15/8286* (2013.01); *A01N 37/46* (2013.01); *C07K 14/21* (2013.01); *C07K 14/265* (2013.01); *C07K 14/32* (2013.01); *C07K 14/33* (2013.01)

(58) Field of Classification Search
None
See application file for complete search history.

(56) References Cited

U.S. PATENT DOCUMENTS 10,231,460 B2 * 3/2019 Gruver ............... C12N 15/8286

FOREIGN PATENT DOCUMENTS

WO 2016114973 A1 7/2016

OTHER PUBLICATIONS

Uniprot A0A109LFP8_PSEFL, 2016, https://www.uniprot.org/uniprot/A0A109LFP8.*
Guo et al, 2004, Proc. Natl. Acad. Sci. USA 101: 9205-9210.*
Anderson et al, 2018, Transgenic Res. 27:103-113.*
Database UNIPROT: EBI Accession No. UNIPROT: A0A0R3A4NO, Jan. 20, 2016 (Jan. 20, 2016), XP002775926.
Gao Yong.; et al: "Characterization of Cry34Ab1 and Cry35Ab1 insecticidal crystal proteins expressed in transgenic corn plants and Pseudomonas fluorescens", Journal of Agricultural and Food Chemistry, American Chemical Society, Books and Journals Division, Dec. 29, 2004 (Dec. 29, 2004), vol. 52, No. 26, pp. 8057-8065.
Daxu Li.; et al: "Agrobacterium-mediated genetic transformation of Elymus breviaristatus with Pseudomonas pseudoalcaligenes insecticidal protein gene", Plant Cell, Tissue and Organ Culture, Kluwer Academic Publishers, Jun. 14, 2007 (Jun. 14, 2007), vol. 89, No. 2-3, pp. 159-168.
International Search Report and Written Opinion for International Application PCT/US2017/051460, dated Feb. 9, 2018.

* cited by examiner

*Primary Examiner* — Anne Kubelik

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

4 Claims, 6 Drawing Sheets

Specification includes a Sequence Listing.

FIG. 1B

```
                  1                                                                              80
IPD086Aa-1   (1)  MFLTRVEHSLSDCKCAHQNIYETEIYDGTSWVAHGQMVVLEDAVTHNGVHAHNIGYNGSNHSLVLQGGTGRQRYNARLNL
IPD086Ab-1   (1)  MFLTRVEHSLSDCKCAHQNIYETEIYDGTSWVAHGQMVVLEDAVTHNGVHAHNIGYNGSNHSLVLQGGTGRQRYNARLNL
IPD086Ad-1   (1)  MFLTRVEHSLSDCKCAHQNIYETEIYDGTSWVAHGQMVVLEDAVTHNGVHAHNIGYNGSNHSLVLQGGTGRQRYNARLNL
IPD086Af-1   (1)  MFLTRVEHSLSDCKCAHQNIYETEIYDGTSWVAHGQMVVLEDAVTHNGVHAHNIGYNGSNHSLVLQGGTGRQRYNARLNL
IPD086Ag-1   (1)  MFLTRVEHSLSDCKCAHQNIYETEIYDGTSWVAHGQMVVLEDAVTHNGVHAHNIGYNGSNHSLVLQGGTGRQRYNARLNL
                  81                                                                            160
IPD086Aa-1  (81)  TECGSAFVGTL[illegible]VAGDAP[illegible]AIRGVALANVFDTKRYLRPKPKTKDDPAVKCDPNAPSVAWDQFSIKAQWIDNVLTVTYLLG
IPD086Ab-1  (81)  TECGSAFVGTL[illegible]VAGDAP[illegible]AIRGVALANVFDTKRYLRPKPKTKDDPAVKCDPNAPSVAWDQFSIKAQWIDNVLTVTYLLG
IPD086Ad-1  (81)  TECGSAFVGTL[illegible]VAGDAP[illegible]AIRGVALANVFDTKRYLRPKPKTKDDPAVKCDPNAPSVAWDQFSIKAQWIDNVLTVTYLLG
IPD086Af-1  (81)  TECGSAFVGTLEVAGDAP[illegible]AIRGVALANVFDTKRYLRPKPKTKDDPAVKCDPNAPSVAWDQFSIKAQWIDNVLTVTYLLG
IPD086Ag-1  (81)  TECGSAFVGTLEVAGDAP[illegible]AIRGVALANVFDTKRYLRPKPKTKDDPAVKCDPNAPSVAWDQFSIKAQWIDNVLTVTYLLG
                  161                                                                           240
IPD086Aa-1 (161)  [illegible]VDVSNRVRVTAVDR[illegible]KGETTLEMVPQLDPPGPQDSFVITLYSGNRTFGGEYTSDDEEAYCWFGSSTPSISEQRSRVFAE
IPD086Ab-1 (161)  [illegible]VDVSNRVRVTAVDR[illegible]KGETTLEMVPQLDPPGPQDSFVITLYSGNRTFGGEYTSDDEEAYCWFGSSTPSISEQRSRVFAE
IPD086Ad-1 (161)  LVDVSNRVRVTAVDR[illegible]KGETTLEMVPQLDPPGPQDSFVITLYSGNRTFGGEYTSDDEEAYCWFGSSTPSISEQRSRVFAE
IPD086Af-1 (161)  [illegible]VDVSNRVRVTAVDR[illegible]KGETTLEMVPQLDPPGPQDSFVITLYSGNRTFGGEYTSDDEEAYCWFGSSTPSISEQRSRVFAE
IPD086Ag-1 (161)  [illegible]VDVSNRVRVTAVDR[illegible]KGETTLEMVPQLDPPGPQDSFVITLYSGNRTFGGEYTSDDEEAYCWFGSSTPSISEQRSRVFAE
                  241                                                                           320
IPD086Aa-1 (241)  VREGAAALATTA[illegible]ISTPLEGDAATRTLQDLDNISSLTVVTDKDGNRMTIDHAQTTCGGYFNKCLVNALDSKWIEGIYGHA
IPD086Ab-1 (241)  VREGAAALATTA[illegible]ISTPLEGDAATRTLQDLDNISSLTVVTDKDGNRMTIDHAQTTCGGYFNKCLVNALDSKWIEGIYGHA
IPD086Ad-1 (241)  VREGAAALATTA[illegible]ISTPLEGDAATRTLQDLDNISSLTVVTDKDGNRMTIDHAQTTCGGYFNKCLVNALDSKWIEGIYGHA
IPD086Af-1 (241)  VREGAAALATTA[illegible]ISTPLEGDAATRTLQDLDNISSLTVVTDKDGNRMTIDHAQTTCGGYFNKCLVNALDSKWIEGIYGHA
IPD086Ag-1 (241)  VREGAAALATTA[illegible]ISTPLEGDAATRTLQDLDNISSLTVVTDKDGNRMTIDHAQTTCGGYFNKCLVNALDSKWIEGIYGHA
                  321                                                                           400
IPD086Aa-1 (321)  Y[illegible]LPGGVQKVFNDKKSFFQKKAVLGTGQMLYDNLGTSPTYADLIKRIKGDAMKQSWKSLGDTKGGDKDESLAYQEASNAL
IPD086Ab-1 (321)  YSLPGGVQKVFNDKKSFFQKKAVLGTGQMLYDNLGTSPTYADLIKRIKGDAMKQSWKSLGDTKGGDKDESLAYQEASNAL
IPD086Ad-1 (321)  YSLPGGVQKVFNDKKSFFQKKAVLGTGQMLYDNLGTSPTYADLIKRIKGDAMKQSWKSLGDTKGGDKDESLAYQEASNAL
IPD086Af-1 (321)  Y[illegible]LPGGVQKVFNDKKSFFQKKAVLGTGQMLYDNLGTSPTYADLIKRIKGDAMKQSWKSLGDTKGGDKDESLAYQEASNAL
IPD086Ag-1 (321)  Y[illegible]LPGGVQKVFNDKKSFFQKKAVLGTGQMLYDNLGTSPTYADLIKRIKGDAMKQSWKSLGDTKGGDKDESLAYQEASNAL
                  401                                                                           480
IPD086Aa-1 (401)  YIEGYRDGVPEMQFYLQDNPKKWAADYFAWLSDEANLLTWSIQVASKMFDNVRQRMYEWYVKLQVLDPD[illegible]NYGQRFMTIA
IPD086Ab-1 (401)  YIEGYRDGVPEMQPYLQDNPKKWAADYFAWLSDEANLLTWSIQVASKMFDNVRQRMYEWYVKLQVLDPD[illegible]NYGQRFMTIA
IPD086Ad-1 (401)  YIEGYRDGVPEMQPYLQDNPKKWAADYFAWLSDEANLLTWSIQVASKMFDNVRQRMYEWYVKLQVLDPD[illegible]NYGQRFMTIA
IPD086Af-1 (401)  YIEGYRDGVPEMQPYLQDNPKKWAADYFAWLSDEANLLTWSIQVASKMFDNVRQRMYEWYVKLQVLDPD[illegible]NYGQRFMTIA
IPD086Ag-1 (401)  YIEGYRDGVPEMQPYLQDNPKKWAADYFAWLSDEANLLTWSIQVASKMFDNVRQRMYEWYVKLQVLDPD[illegible]NYGQRFMTIA
                  481                                                                           560
IPD086Aa-1 (481)  YAALLGVNYSKSRWSDDLKPFLTSLIEQAIAGKVDPTLMDQIQQQAALENQELLKTLITTTDSIHNLVDGIAAAITEYQL
IPD086Ab-1 (481)  YAALLGVNYSKSRWSDDLKPFLTSLIEQAIAGKVDPTLMDQIQQQAALENQELLKTLITTTDSIHNLVDGIAAAITEYQL
IPD086Ad-1 (481)  YAALLGVNYSKSRWSDDLKPFLTSLIEQAIAGKVDPTLMDQIQQQAALENQELLKTLITTTDSIHNLVDGIAAAITEYQL
IPD086Af-1 (481)  YAALLGVNYSKSRWSDDLKPFLTSLIEQAIAGKVDPTLMDQIQQQAALENQELLKTLITTTDSIHNLVDGIAAAITEYQL
IPD086Ag-1 (481)  YAALLGVNYSKSRWSDDLKPFLTSLIEQAIAGKVDPTLMDQIQQQAALENQELLKTLITTTDSIHNLVDGIAAAITEYQL
                  561                                                                           640
IPD086Aa-1 (561)  KKGNQPLSRIAQDPELQGMIGQRLDGQQYKAWGELSRKGKVGGVLTVVFYGASAGYLIYSLADNPGRPLTPKEIIEKINL
IPD086Ab-1 (561)  KKGNQPLSRIAQDPELQGMIGQRLDGQQYKAWGELSRKGKVGGVLTVVFYGASAGYLIYSLADNPGRPLTPKEIIEKINL
IPD086Ad-1 (561)  KKGNQPLSRIAQDPELQGMIGQRLDGQQYKAWGELSRKGKVGGVLTVVFYGASAGYLIYSLADNPGRPLTPKEIIEKINL
IPD086Af-1 (561)  KKGNQPLSRIAQDPELQGMIGQRLDGQQYKAWGELSRKGKVGGVLTVVFYGASAGYLIYSLADNPGRPLTPKEIIEKINL
IPD086Ag-1 (561)  KKGNQPLSRIAQDPELQGMIGQRLDGQQYKAWGELSRKGKVGGVLTVVFYGASAGYLIYSLADNPGRPLTPKEIIEKINL
                  641                                                                           720
IPD086Aa-1 (641)  GLLALATLVKGVQKMMSIGVGRFLENFSKAAEGGAFRAFAGDIATWFKAGGKIVPEGKLGKAFVTIFGESSAEFMARRIG
IPD086Ab-1 (641)  GLLALATLVKGVQKMMSIGVGRFLENFSKAAEGGAFRAFAGDIATWFKAGGKIVPEGKLGKAFVTIFGESSAEFMARRIG
IPD086Ad-1 (641)  GLLALATLVKGVQKMMSIGVGRFLENFSKAAEGGAFRAFAGDIATWFKAGGKIVPEGKLGKAFVTIFGESSAEFMARRIG
IPD086Af-1 (641)  GLLALATLVKGVQKMMSIGVGRFLENFSKAAEGGAFRAFAGDIATWFKAGGKIVPEGKLGKAFVTIFGESSAEFMARRIG
IPD086Ag-1 (641)  GLLALATLVKGVQKMMSIGVGRFLENFSKAAEGGAFRAFAGDIATWFKAGGKIVPEGKLGKAFVTIFGESSAEFMARRIG
                  721                                                                           800
IPD086Aa-1 (721)  PALAVVGMILSSFMLYDAIKSGAVREIVFEALNTFFALADVVFIGLELFSVGWAGPVGLAIAVVGVIVILVQFIWNLIEP
IPD086Ab-1 (721)  PALAVVGMILSSFMLYDAIKSGAVREIVFEALNTFFALADVVFIGLELFSVGWAGPVGLAIAVVGVIVILVQFIWNLIEP
IPD086Ad-1 (721)  PALAVVGMILSSFMLYDAIKSGAVREIVFEALNTFFALADVVFIGLELFSVGWAGPVGLAIAVVGVIVILVQFIWNLIEP
IPD086Af-1 (721)  PALAVVGMILSSFMLYDAIKSGAVREIVFEALNTFFALADVVFIGLELFSVGWAGPVGLAIAVVGVIVILVQFIWNLIEP
IPD086Ag-1 (721)  PALAVVGMILSSFMLYDAIKSGAVREIVFEALNTFFALADVVFIGLELFSVGWAGPVGLAIAVVGVIVILVQFIWNLIEP
                  801                      825
IPD086Aa-1 (801)  PTPAPDPITEFVNGPMVNQGFAVSA
IPD086Ab-1 (801)  PTPAPDPITEFVNGPMVNQGFAVSA
IPD086Ad-1 (801)  PTPAPDPITEFVNGPMVNQGFAVSA
IPD086Af-1 (801)  PTPAPDPITEFVNGPMVNQGFAVSA
IPD086Ag-1 (801)  PTPAPDPITEFVNGPMVNQGFAVSA
```

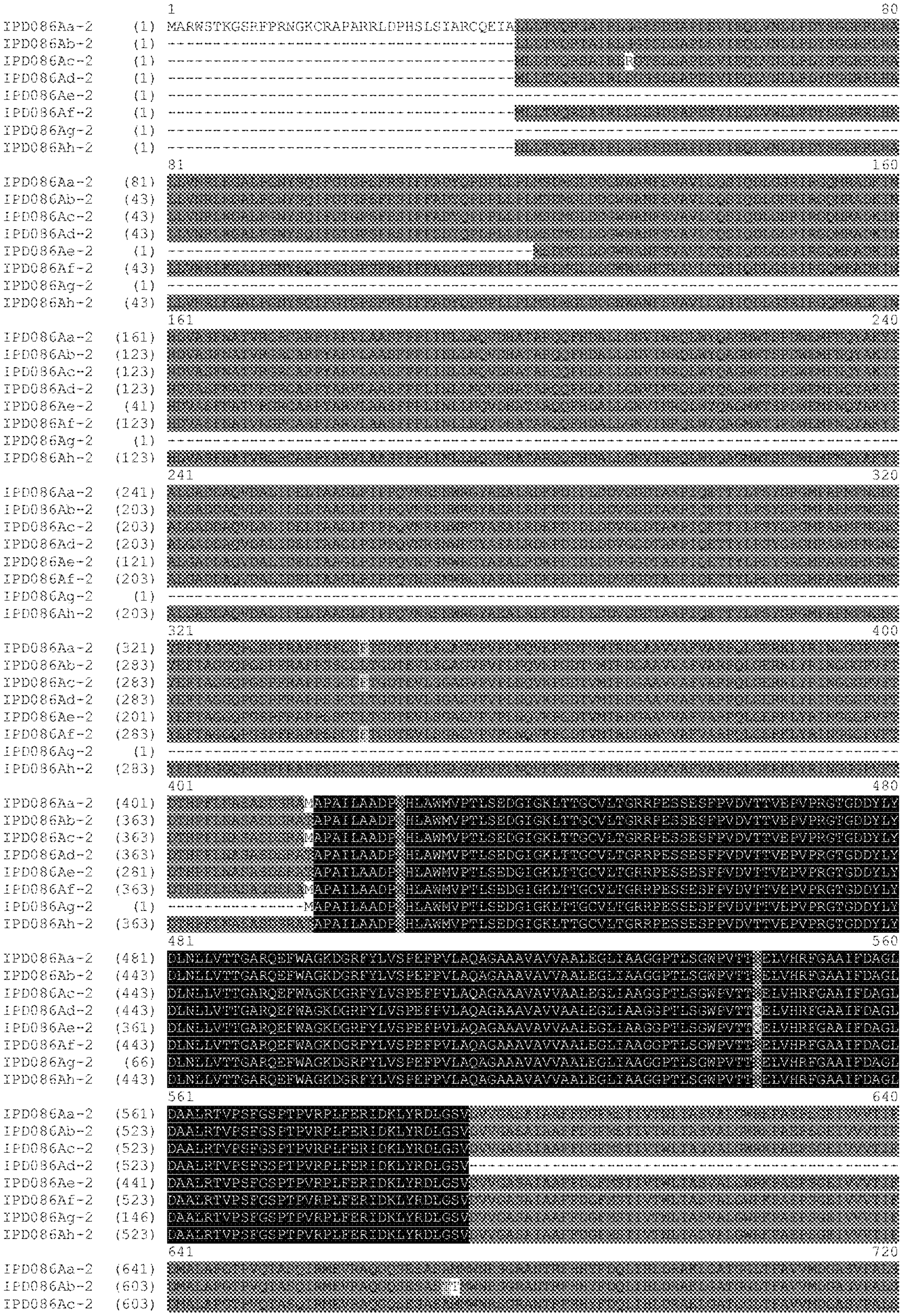

FIG. 1C

```
                1                                                              80
IPD086Aa-2  (1) MARWSTKGSRFPRNGKCRAPARRLDPHSLSIARCQEIA
IPD086Ab-2  (1) -------------------------------------
IPD086Ac-2  (1) -------------------------------------
IPD086Ad-2  (1) -------------------------------------
IPD086Ae-2  (1) -------------------------------------
IPD086Af-2  (1) -------------------------------------
IPD086Ag-2  (1) -------------------------------------
IPD086Ah-2  (1) -------------------------------------
                81                                                             160
IPD086Aa-2  (81)
IPD086Ab-2  (43)
IPD086Ac-2  (43)
IPD086Ad-2  (43)
IPD086Ae-2  (1)  ----------------------------------------
IPD086Af-2  (43)
IPD086Ag-2  (1)  ----------------------------------------
IPD086Ah-2  (43)
                161                                                            240
IPD086Aa-2  (161)
IPD086Ab-2  (123)
IPD086Ac-2  (123)
IPD086Ad-2  (123)
IPD086Ae-2  (41)
IPD086Af-2  (123)
IPD086Ag-2  (1)  ----------------------------------------
IPD086Ah-2  (123)
                241                                                            320
IPD086Aa-2  (241)
IPD086Ab-2  (203)
IPD086Ac-2  (203)
IPD086Ad-2  (203)
IPD086Ae-2  (121)
IPD086Af-2  (203)
IPD086Ag-2  (1)  ----------------------------------------
IPD086Ah-2  (203)
                321                                                            400
IPD086Aa-2  (321)
IPD086Ab-2  (283)
IPD086Ac-2  (283)
IPD086Ad-2  (283)
IPD086Ae-2  (201)
IPD086Af-2  (283)
IPD086Ag-2  (1)  ----------------------------------------
IPD086Ah-2  (283)
                401                                                            480
IPD086Aa-2  (401)                    APAILAADE HLAWMVPTLSEDGIGKLTTGCVLTGRRPESSESFPVDVTTVEPVPRGTGDDYLY
IPD086Ab-2  (363)                    APAILAADE HLAWMVPTLSEDGIGKLTTGCVLTGRRPESSESFPVDVTTVEPVPRGTGDDYLY
IPD086Ac-2  (363)                    APAILAADE HLAWMVPTLSEDGIGKLTTGCVLTGRRPESSESFPVDVTTVEPVPRGTGDDYLY
IPD086Ad-2  (363)                    APAILAADE HLAWMVPTLSEDGIGKLTTGCVLTGRRPESSESFPVDVTTVEPVPRGTGDDYLY
IPD086Ae-2  (281)                    APAILAADE HLAWMVPTLSEDGIGKLTTGCVLTGRRPESSESFPVDVTTVEPVPRGTGDDYLY
IPD086Af-2  (363)                    APAILAADE HLAWMVPTLSEDGIGKLTTGCVLTGRRPESSESFPVDVTTVEPVPRGTGDDYLY
IPD086Ag-2  (1)  ----------------M APAILAADE HLAWMVPTLSEDGIGKLTTGCVLTGRRPESSESFPVDVTTVEPVPRGTGDDYLY
IPD086Ah-2  (363)                    APAILAADE HLAWMVPTLSEDGIGKLTTGCVLTGRRPESSESFPVDVTTVEPVPRGTGDDYLY
                481                                                            560
IPD086Aa-2  (481) DLNLLVTTGARQEFWAGKDGRFYLVSPEFPVLAQAGAAAVAVVAALEGLIAAGGPTLSGWPVTT ELVHRFGAAIFDAGL
IPD086Ab-2  (443) DLNLLVTTGARQEFWAGKDGRFYLVSPEFPVLAQAGAAAVAVVAALEGLIAAGGPTLSGWPVTT ELVHRFGAAIFDAGL
IPD086Ac-2  (443) DLNLLVTTGARQEFWAGKDGRFYLVSPEFPVLAQAGAAAVAVVAALEGLIAAGGPTLSGWPVTT ELVHRFGAAIFDAGL
IPD086Ad-2  (443) DLNLLVTTGARQEFWAGKDGRFYLVSPEFPVLAQAGAAAVAVVAALEGLIAAGGPTLSGWPVTT ELVHRFGAAIFDAGL
IPD086Ae-2  (361) DLNLLVTTGARQEFWAGKDGRFYLVSPEFPVLAQAGAAAVAVVAALEGLIAAGGPTLSGWPVTT ELVHRFGAAIFDAGL
IPD086Af-2  (443) DLNLLVTTGARQEFWAGKDGRFYLVSPEFPVLAQAGAAAVAVVAALEGLIAAGGPTLSGWPVTT ELVHRFGAAIFDAGL
IPD086Ag-2  (66)  DLNLLVTTGARQEFWAGKDGRFYLVSPEFPVLAQAGAAAVAVVAALEGLIAAGGPTLSGWPVTT ELVHRFGAAIFDAGL
IPD086Ah-2  (443) DLNLLVTTGARQEFWAGKDGRFYLVSPEFPVLAQAGAAAVAVVAALEGLIAAGGPTLSGWPVTT ELVHRFGAAIFDAGL
                561                                                            640
IPD086Aa-2  (561) DAALRTVPSFGSPTPVRPLFERIDKLYRDLGSV
IPD086Ab-2  (523) DAALRTVPSFGSPTPVRPLFERIDKLYRDLGSV
IPD086Ac-2  (523) DAALRTVPSFGSPTPVRPLFERIDKLYRDLGSV
IPD086Ad-2  (523) DAALRTVPSFGSPTPVRPLFERIDKLYRDLGSV-------
IPD086Ae-2  (441) DAALRTVPSFGSPTPVRPLFERIDKLYRDLGSV
IPD086Af-2  (523) DAALRTVPSFGSPTPVRPLFERIDKLYRDLGSV
IPD086Ag-2  (146) DAALRTVPSFGSPTPVRPLFERIDKLYRDLGSV
IPD086Ah-2  (523) DAALRTVPSFGSPTPVRPLFERIDKLYRDLGSV
                641                                                            720
IPD086Aa-2  (641)
IPD086Ab-2  (603)
IPD086Ac-2  (603)
```

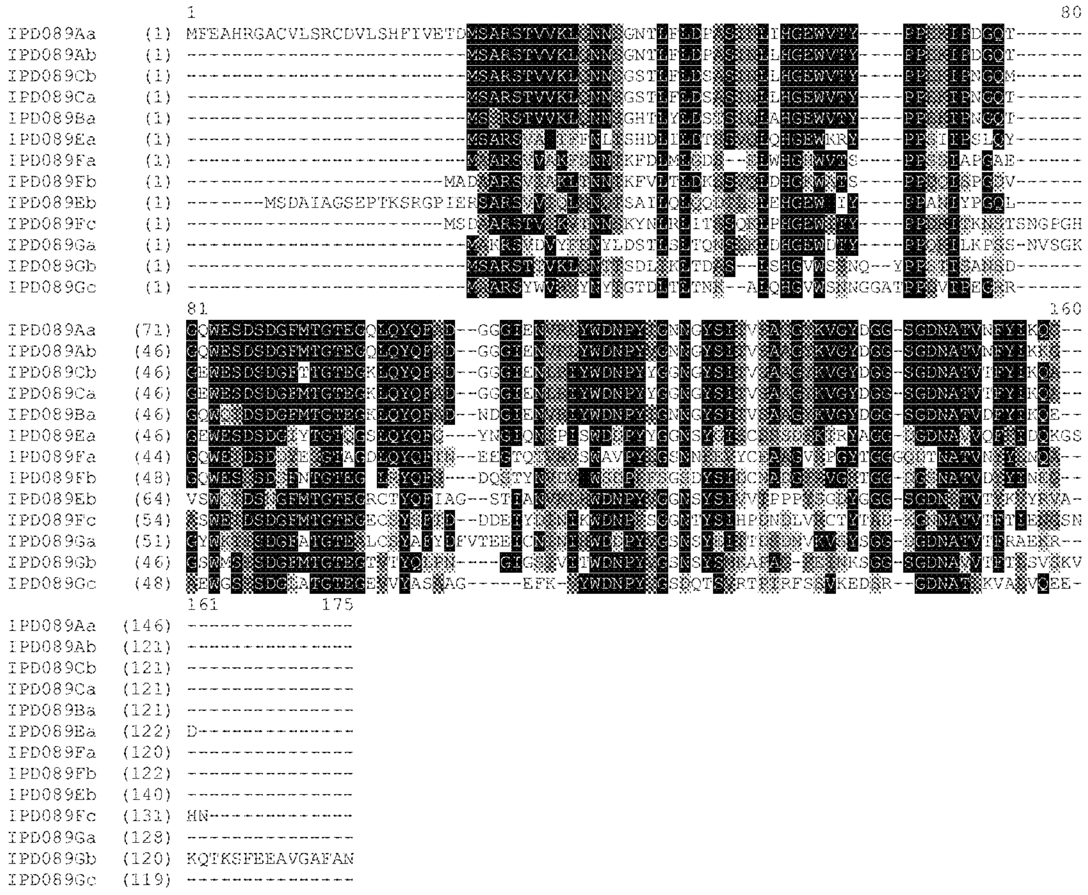

FIG. 1D

```
                   1                                                                          80
IPD089Aa    (1)  MFEAHRGACVLSRCDVLSHFIVETDMSARSTVVKI NN GNT F LD    LHGEWVTY----P   I DGQT------
IPD089Ab    (1)  ------------------------MSARSTVVKI NN GNT F LD    LHGEWVTY----P   I DGQT------
IPD089Cb    (1)  ------------------------MSARSTVVKI NN GST F L     LHG  VTY----P   I NGQM------
IPD089Ca    (1)  ------------------------MSARSTVVKI NN GST F LDS   LHGEWVTY----P   I NGQT------
IPD089Ba    (1)  ------------------------MS RSTVVKI NN GHT Y L S S LHGEWVTY----P   I NGQT------
IPD089Ea    (1)  ------------------------MSARS   T  NL SHDL          QHGEWKR ----P    P SL Y------
IPD089Fa    (1)  ------------------------- ARS  V  NN KFD    SD  - WHE  V S----P   AP AE------
IPD089Fb    (1)  ---------------------MAD ARS  K  NN KFV TLD  S  DHG  N S----P   SP  V------
IPD089Eb    (1)  --------MSDAIAGSEPTKSRGPIEF ARS  V  NN  SA   Q  C   HGEW I ----  AR YP QL------
IPD089Fc    (1)  -----------------------MSD ARSTV    NN KYN RE I   D  HGE  T ----P   KK TSNGPGH
IPD089Ga    (1)  ------------------------ KR  DV Y  YLDST  TQK S  DHGEWD T----P   LKP S-NVSGK
IPD089Gb    (1)  ------------------------MSARST VK  N  SDL K TD S -- HGWS NQ--YP   T AN D------
IPD089Gc    (1)  ------------------------- ARSYW  K  NY GTDL T TN - A  HGWS NGGATP V  P  R------
                  81                                                                         160
IPD089Aa   (71)  GQWESDSDGFMTGTEG LQYQE D--GG  E    YWDNPY GNN YS V A G KVG D GG-SGDNATV EY KQ --
IPD089Ab   (46)  GQWESDSDGFMTGTEG LQYQE D--GG  E    YWDNPY GNN YS V A G KVG D GG-SGDNATV EY KK --
IPD089Cb   (46)  G WESDSDGF TGTEGK LQYQE D--GG  E N  YWDNPY GNN YS V A G KVG D GG-SGDNATV EY KQ --
IPD089Ca   (46)  G WESDSDGFMTGTEG  LQYQE D--GG  E N  YWDNPY GNN YS V A G KVG D GG-SGDNATV EY KQ --
IPD089Ba   (46)  GQW  DSDG MTGTEG RLQYQE D--ND  E N  YWDNPY GNN YS  A G KVG Y DGG-SGDNATV DY  E--
IPD089Ea   (46)  G WESDSDG  TGT GS QYQE ----YN  D  PY S  Y GN   R A GR  A GG -GDNA  R T KGS
IPD089Fa   (44)  GQWE DBD   ST A  RQYQE E--EE TQ    AVE GS N  YC        PGY TGG GT NATV   Q R--
IPD089Fb   (48)  G WES  DG MTGTEG LY E -----DQ TY    GKE  GS N YS C A   GD    G  A ATV  Y  N--
IPD089Eb   (64)  VSW    DS GFMTGTE  RCTY  IAG--ST AK    WDNPY GGN YS  V  FPP G   GG-SGDN TV VK Y VA-
IPD089Fc   (54)  K SWE DSDGFMTGTE C  Y   --DDE YK     WDNE CG TYS HP ND LV CT LE -- NATV ET     SN
IPD089Ga   (51)  Y K  SDGEATGTE LC  A Y FVTEE C L    P GSN YT    V KV G- -SGDNATV  RAE R--
IPD089Gb   (46)  S   SDGFMTGTE  T  Q N ---  C  VF   WDNPY GSN KS  A A  -- KRS GC -SGDNA  FT S V KV
IPD089Gc   (48)  PWG SDG ATG E  VY AS AG------EFK   YWDNPY GS QT  RT RFS KED R--GDNAT KVA  EE-
                 161     175
IPD089Aa  (146)  ----------------
IPD089Ab  (121)  ----------------
IPD089Cb  (121)  ----------------
IPD089Ca  (121)  ----------------
IPD089Ba  (121)  ----------------
IPD089Ea  (122)  D---------------
IPD089Fa  (120)  ----------------
IPD089Fb  (122)  ----------------
IPD089Eb  (140)  ----------------
IPD089Fc  (131)  HN--------------
IPD089Ga  (128)  ----------------
IPD089Gb  (120)  KQTKSFEEAVGAFAN
IPD089Gc  (119)  ----------------
```

INSECTICIDAL PROTEINS AND METHODS FOR THEIR USE

CROSS-REFERENCE TO RELATED APPLICATIONS

This application claims priority to International Patent Application PCT/US2017/51460 filed on Sep. 14, 2017, which claims priority to U.S. Provisional Application No. 62/415,781, filed Nov. 1, 2016, the contents of which are herein incorporated by reference in their entirety.

REFERENCE TO SEQUENCE LISTING SUBMITTED ELECTRONICALLY

A sequence listing having the file name "6000WOPCT_SequenceList.txt" created on Sep. 1, 2017, and having a size of 199 kilobytes is filed in computer readable form concurrently with the specification. The sequence listing is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of Bt. These genetically engineered crops are now widely used in agriculture and have provided the farmer with an environmentally friendly alternative to traditional insect-control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera including but not limited to insect pests that have developed resistance to existing insecticides.

SUMMARY

Compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues and seeds.

In particular, isolated or recombinant nucleic acid molecules are provided encoding Insecticidal Proteins IPD078-1, IPD078-2, IPD084, IPD086-1, IPD086-2, IPD087, and IPD089 polypeptides including amino acid substitutions, deletions, insertions, and fragments thereof, and combinations thereof. Additionally, amino acid sequences corresponding to the IPD078-1, IPD078-2, IPD084, IPD086-1, IPD086-2, IPD087, and IPD089 polypeptides are encompassed. Provided are isolated or recombinant nucleic acid molecules capable of encoding a IPD078-1, IPD078-2, IPD084, IPD086-1, IPD086-2, IPD087, and IPD089 polypeptides of SEQ ID NOs: 43-82 as well as amino acid substitutions, deletions, insertions, fragments thereof and combinations thereof. Nucleic acid sequences that are complementary to a nucleic acid sequence of the embodiments or that hybridize to a sequence of the embodiments are also encompassed. Also provided are isolated or recombinant IPD078-1, IPD078-2, IPD084, IPD086-1, IPD086-2, IPD087, and IPD089 polypeptides of SEQ ID NO: 43-82 as well as amino acid substitutions, deletions, insertions, fragments thereof and combinations thereof.

Methods are provided for producing the insecticidal polypeptides and for using these polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional pesticidal proteins, for example, one or more additional genes for controlling Coleopteran, Lepidopteran, Hemipteran or nematode pests. It will be understood by one of skill in the art that the transgenic plant may comprise any gene imparting an agronomic trait of interest.

Methods for detecting the nucleic acids and polypeptides of the embodiments in a sample are also included. A kit for detecting the presence of an insecticidal polypeptide of the disclosure or detecting the presence of a nucleotide sequence encoding an insecticidal polypeptide of the disclosure in a sample is provided. The kit may be provided along with all reagents and control samples necessary for carrying out a method for detecting the intended agent, as well as instructions for use.

The compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of the insecticidal polypeptides of the disclosure or nucleic acids encoding same in products or organisms.

DESCRIPTION OF THE FIGURES

FIGS. 1A-1D. Protein sequence alignments for members of the (FIG. 1A) IPD085, (FIG. 1B) IPD086-1, (FIG. 1C) IPD086-2, and (FIG. 1D) IPD089 classes of protein.

DETAILED DESCRIPTION

Figure 1A:
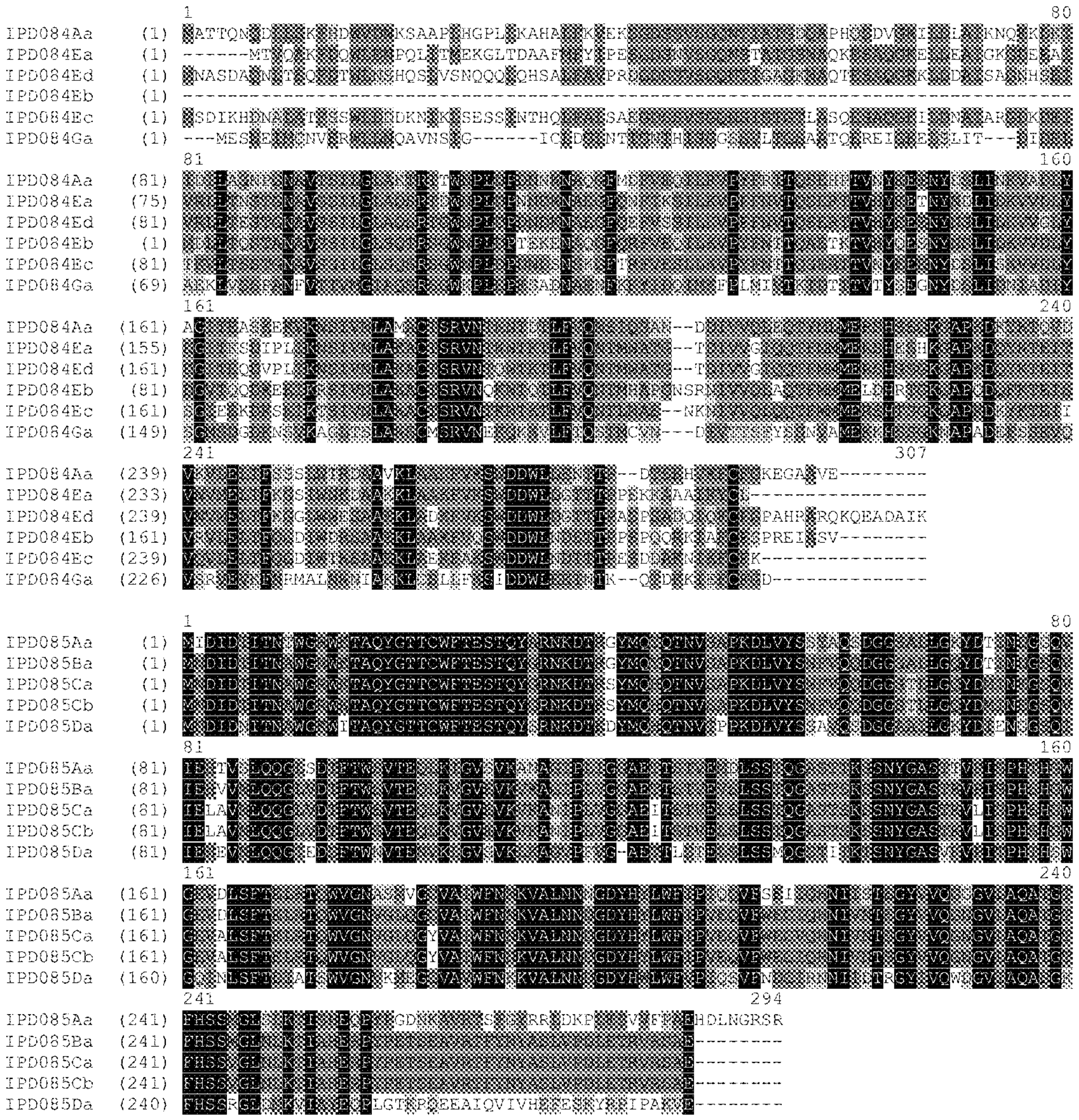

It is to be understood that this disclosure is not limited to the particular methodology, protocols, cell lines, genera, and reagents described, as such may vary. It is also to be understood that the terminology used herein is for the purpose of describing particular embodiments only, and is not intended to limit the scope of the present disclosure.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

The present disclosure is drawn to compositions and methods for controlling pests. The methods involve transforming organisms with nucleic acid sequences encoding an insecticidal polypeptide of the disclosure. In particular, the nucleic acid sequences of the embodiments are useful for preparing plants and microorganisms that possess pesticidal activity. Thus, transformed bacteria, plants, plant cells, plant tissues and seeds are provided. The compositions are pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered insecticidal polypeptides by methods known in the art, such as site-directed mutagenesis, domain swapping or DNA shuffling. The insecticidal polypeptides of the disclosure find use in controlling or killing Lepidopteran, Coleopteran, Dipteran, fungal, Hemipteran and nematode pest populations and for producing compositions with pesticidal activity. Insect pests of interest include, but are not limited to, Lepidoptera species including but not limited to: diamond-back moth, e.g., *Helicoverpa zea* Boddie; soybean looper, e.g., *Pseudoplusia includens* Walker; and velvet bean caterpillar e.g., *Anticarsia gemmatalis*; Hübner and Coleoptera species including but not limited to Western corn rootworm (*Diabrotica virgifera*)—WCRW, Southern corn rootworm (*Diabrotica undecimpunctata howardi*)—SCRW, and Northern corn rootworm (*Diabrotica barberi*)—NCRW.

By "pesticidal toxin" or "pesticidal protein" is used herein to refer to a toxin that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans, Burkholderia* sp., *Enterobacter cloacae*, and *Paenibacillus popilliae.*

In some embodiments the insecticidal polypeptides of the disclosure include amino acid sequences deduced from the full-length nucleic acid sequences disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are novel isolated or recombinant nucleic acid sequences that confer pesticidal activity. Also provided are the amino acid sequences of insecticidal polypeptides of the disclosure. The protein resulting from translation of these insecticidal polypeptide genes allows cells to control or kill pests that ingest it.

Nucleic Acid Molecules, and Variants and Fragments Thereof

One aspect of the disclosure pertains to isolated or recombinant nucleic acid molecules comprising nucleic acid sequences encoding insecticidal polypeptides of the disclosure or biologically active portions thereof, as well as nucleic acid molecules sufficient for use as hybridization probes to identify nucleic acid molecules encoding proteins with regions of sequence homology. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecule encoding an insecticidal polypeptide can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding an insecticidal polypeptide of the disclosure has one or more changes in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an insecticidal polypeptide is a non-genomic sequence.

Polynucleotides encoding IPD078-1, IPD078-2, IPD084, IPD086-1, IPD086-2, IPD087, and IPD089 polypeptides are encompassed by the disclosure. A variety of polynucleotides encoding IPD078-1, IPD078-2, IPD084, IPD086-1, IPD086-2, IPD087, and IPD089 polypeptides are contemplated. A source of a polynucleotide encoding a IPD078-1, IPD078-2, IPD084, IPD086-1, IPD086-2, IPD087, and IPD089 polypeptides or related proteins is a bacterial strain that contains one of the polynucleotides of SEQ ID NOs: 1-42. A source of a polynucleotide encoding a IPD078-1, IPD078-2, IPD084, IPD086-1, IPD086-2, IPD087, or IPD089 polypeptide or related proteins may be from from a *Pseudomonas, Burkholderia, Enterobacter, Desulfovibrio, Pectobacterium, Klebsiella, Salinvibrio, Sinorhizobium, Aquimarina*, or *Nocardia* strain. One source of a polynucleotide encoding a IPD078-1, IPD078-2, IPD084, IPD086-1, IPD086-2, IPD087, or IPD089 polypeptide or related proteins is from a *Pseudomonas* strain selected from but not limited to *Pseudomonas chlororaphis, Pseudomonas entomohila, Pseudomonas aueruginosa, Pseudomonas phage, Pseudomonas syringae, Pseudomonas lini, Aquimarina muelleri, Nocardia gamkensis, Enterobacter cloacae, Desulfovibrio zosterae, Sinorhizobium medicae, Pectobacterium carotovorum, Pectobacterium wasabiae, Klebsiella quasipneumoniae, Burkholderia ambifaria, Burkholderia cenocepacia, Burkholderia pyrrocinia, Burkholderia glumae, Burkholderia anthina, Burkholderia multivorans*, and *Burkholderia cepacia.*

In some embodiments the polynucleotide encodes a IPD078-1, IPD078-2, IPD084, IPD086-1, IPD086-2, IPD087, or IPD089 polypeptide sufficiently homologous to the amino acid sequence of one or more of SEQ ID NOs: 1-42 and which has insecticidal activity. "Sufficiently homologous" is used herein to refer to an amino acid sequence that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins taking into account amino acid similarity and the like. As used herein the term "about" when used with sequence identity means±0.5%. In some embodiments the sequence homology is against the full length sequence of a IPD078-1, IPD078-2, IPD084, IPD086-1, IPD086-2, IPD087, or IPD089 polypeptide.

In some embodiments the polynucleotide encodes a IPD078-1, IPD078-2, IPD084, IPD086-1, IPD086-2, IPD087, or IPD089 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to one or more of SEQ ID NOs: 43-82.

These polynucleotide sequences were isolated from a *Pseudomonas, Burkholderia, Enterobacter, Desulfovibrio, Pectobacterium, Klebsiella, Salinvibrio, Sinorhizobium, Aquimarina*, or *Nocardia* or other bacterial host and are thus suitable for expression of the encoded insecticidal polypeptides in other bacterial hosts that include but are not limited to *Agrobacterium, Bacillus, Escherichia, Salmonella, Pseudomonas* and *Rhizobium* bacterial host cells. The polynucleotides are also useful as probes for isolating homologous or substantially homologous polynucleotides that encode the insecticidal polypeptides of the disclosure or related proteins. Such probes can be used to identify homologous or substantially homologous polynucleotides derived from *Pseudomonas* or other related bacteria.

Polynucleotides that encode an insecticidal polypeptide can also be synthesized de novo from a polypeptide sequence. The sequence of the polynucleotide gene can be deduced from a polypeptide sequence through use of the genetic code. Computer programs such as "BackTranslate" (GCG™ Package, Acclerys, Inc. San Diego, Calif.) can be used to convert a peptide sequence to the corresponding nucleotide sequence encoding the peptide. Furthermore, synthetic polynucleotide sequences of the disclosure can be designed so that they will be expressed in plants using techniques known in the art.

"Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments a nucleic acid molecule encoding the insecticidal polypeptide of the disclosure is a non-genomic nucleic acid sequence. As used herein a "non-genomic nucleic acid sequence" or "non-genomic nucleic acid molecule" refers to a nucleic acid molecule that has one or more changes in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA.

Also provided are nucleic acid molecules that encode transcription and/or translation products that are subsequently spliced to ultimately produce functional insecticidal polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an insecticidal polypeptide encoding sequence of the disclosure. An example of trans splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides. Thus, in some embodiments the polynucleotides do not directly encode a full-length insecticidal polypeptide of the disclosure, but rather encode a fragment or fragments of an insecticidal polypeptide of the disclosure. These polynucleotides can be used to express a functional Insecticidal polypeptide of the disclosure through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding insecticidal polypeptides are also encompassed by the embodiments. “Fragment” as used herein refers to a portion of the nucleic acid sequence encoding an insecticidal polypeptide of the disclosure. A fragment of a nucleic acid sequence may encode a biologically active portion of an insecticidal polypeptide of the disclosure or it may be a fragment that can be used as a hybridization probe or PCR primer using methods disclosed below. Nucleic acid molecules that are fragments of a nucleic acid sequence encoding an insecticidal polypeptide of the disclosure comprise at least about 130, 140, 150, 160, 170, 180, 190, 200, 210, 220, 230, 240, 250 or 260, contiguous nucleotides or up to the number of nucleotides present in a full-length nucleic acid sequence encoding an insecticidal polypeptide of the disclosure disclosed herein, depending upon the intended use. “Contiguous nucleotides” is used herein to refer to nucleotide residues that are immediately adjacent to one another. Fragments of the nucleic acid sequences of the embodiments will encode protein fragments that retain the biological activity of the insecticidal polypeptide of the disclosure and, hence, retain insecticidal activity. “Retains insecticidal activity” is used herein to refer to a polypeptide having at least about 10%, at least about 30%, at least about 50%, at least about 70%, 80%, 90%, 95% or higher of the insecticidal activity of the full-length native polypeptide. In one embodiment, the insecticidal activity is Lepidoptera activity. In one embodiment, the insecticidal activity is against a Coleopteran species. In one embodiment, the insecticidal activity is against a *Diabrotica* species. In one embodiment, the insecticidal activity is against one or more insect pests of the corn rootworm complex: Western corn rootworm, *Diabrotica virgifera virgifera*; northern corn rootworm, *D. barberi*: Southern corn rootworm or spotted cucumber beetle; *Diabrotica undecimpunctata howardi*, and the Mexican corn rootworm, *D. virgifera zeae*. In one embodiment, the insecticidal activity is against Western corn rootworm, *Diabrotica virgifera virgifera.*

In some embodiments a fragment of a nucleic acid sequence encoding an insecticidal polypeptide of the disclosure encoding a biologically active portion of a protein will encode at least about 15, 20, 30, 40, 50, 60, 70, 75, 76, 77, 78, 79, 80, 81, 82, 83, 84 or 85, contiguous amino acids or up to the total number of amino acids present in a full-length insecticidal polypeptide of the embodiments. In some embodiments, the fragment is an N-terminal and/or a C-terminal truncation of at least about 1, 2, 3, 4, 5, 6, 7, 8, 9, 10, 11, 12, 13, 14 or more amino acids from the N-terminus and/or C-terminus by proteolysis, insertion of a start codon, deletion of the codons encoding the deleted amino acids with the concomitant insertion of a stop codon or by insertion of a stop codon in the coding sequence.

The present disclosure provides isolated or recombinant polynucleotides that encode any of the insecticidal polypeptides disclosed herein. In certain embodiments, a recombinant polynucleotide set forth in SEQ ID NOs: 1-42 encodes an insecticidal polypeptide disclosed herein. In a further embodiment, the polynucleotides set forth in Table 2 encode the polypeptides as set forth in Table 2. Those having ordinary skill in the art will readily appreciate that due to the degeneracy of the genetic code, a multitude of nucleotide sequences encoding insecticidal polypeptides of the present disclosure exist.

The skilled artisan will further appreciate that changes can be introduced by mutation of the nucleic acid sequences thereby leading to changes in the amino acid sequence of the encoded insecticidal polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produces by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods disclosed herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene,* 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortie, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA,* 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US Patents, PCT Publications and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 0932670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/US01/06775.

The nucleotide sequences of the embodiments can also be used to isolate corresponding sequences from other organisms, particularly other bacteria, particularly a *Pseudomonas, Burkholderia, Enterobacter, Desulfovibrio, Pectobacterium, Klebsiella, Salinvibrio, Sinorhizobium, Aquimarina*, or *Nocardia* species and more particularly a *Pseudomonas chlororaphis, Pseudomonas entomohila, Pseudomonas aueruginosa, Pseudomonas phage, Pseudomonas syringae, Pseudomonas lini, Aquimarina muelleri, Nocardia gamkensis, Enterobacter cloacae, Desulfovibrio zosterae, Sinorhizobium medicae, Pectobacterium carotovorum, Pectobacterium wasabiae, Klebsiella quasipneumoniae, Burkholderia ambifaria, Burkholderia cenocepacia, Burkholderia pyrrocinia, Burkholderia glumae, Burkholderia anthina, Burkholderia multivorans*, or a *Burkholderia cepacia* strain. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential insecticidal polypeptides from bacterial collections, the bacterial cell lysates can be screened with antibodies generated against an insecticidal polypeptide of the disclosure using Western blotting and/or ELISA methods. This type of assays can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of the insecticidal polypeptides using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands) with sequence information of the insecticidal polypeptides of the disclosure. Any match in peptide sequences indicates the potential of having the homologs in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the insecticidal polypeptide-encoding nucleic acid sequence disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequence encoding an insecticidal polypeptide of the disclosure or a fragment or variant thereof. Methods for the preparation of probes for hybridization are generally known in the art and are disclosed in Sambrook and Russell, (2001), supra.

For example, an entire nucleic acid sequence, encoding an insecticidal polypeptide of the disclosure, disclosed herein or one or more portions thereof may be used as a probe capable of specifically hybridizing to corresponding nucleic acid sequences encoding insecticidal polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. “Stringent conditions” or “stringent hybridization conditions” is used herein to refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the Tm can be approximated from the equation of Meinkoth and Wahl, (1984) *Anal. Biochem.* 138:267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3 or 4° C. lower than the thermal melting point (Tm); moderately stringent conditions can utilize a hybridization and/or wash at 6, 7, 8, 9 or 10° C. lower than the thermal melting point (Tm); low stringency conditions can utilize a hybridization and/or wash at 11, 12, 13, 14, 15 or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, (1993) Laboratory Techniques in Biochemistry and Molecular Biology-Hybridization with Nucleic Acid Probes, Part I, Chapter 2 (Elsevier, N.Y.); and Ausubel, et al., eds. (1995) Current Protocols in Molecular Biology, Chapter 2 (Greene Publishing and Wiley-Interscience, New York). See, Sambrook, et al., (1989) Molecular Cloning: A Laboratory Manual (2d ed., Cold Spring Harbor Laboratory Press, Cold Spring Harbor, N.Y.).

Proteins and Variants and Fragments Thereof

One aspect of the disclosure is isolated insecticidal polypeptides. IPD078-1, IPD078-2, IPD084, IPD086-1, IPD086-2, IPD087, and IPD089 polypeptides are encompassed by the disclosure. One source of a IPD078-1, IPD078-2, IPD084, IPD086-1, IPD086-2, IPD087, or IPD089 polypeptide or related proteins is a bacterial strain that contains the polynucleotide of SEQ ID NOs: 1-42 that encode the IPD078-1, IPD078-2, IPD084, IPD086-1, IPD086-2, IPD087, or IPD089 polypeptides of SEQ ID NOs: 43-82 (See Table 2). In some embodiments a IPD078-1, IPD078-2, IPD084, IPD086-1, IPD086-2, IPD087, or IPD089 polypeptide is sufficiently homologous to one or more amino acid sequences of SEQ ID NOs: 43-82. One of skill in the art will recognize that these values can be appropriately adjusted to determine corresponding homology of proteins taking into account amino acid similarity and the like.

In some embodiments the IPD078-1, IPD078-2, IPD084, IPD086-1, IPD086-2, IPD087, or IPD089 polypeptide has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to one or more of SEQ ID NOs: 43-82.

As used herein, the terms "protein," "peptide molecule," or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process. The terms "amino acid" and "amino acids" refer to all naturally occurring L-amino acids.

In some embodiments a IPD078-1, IPD078-2, IPD084, IPD086-1, IPD086-2, IPD087, and/or IPD089 polypeptide has a calculated molecular weight of between about 20 kDa and about 100 kDa, between about 20 kDa and about 30 kDa, between about 30 kDa and about 40 kDa, between about 50 kDa and about 60 kDa, between about 60 kDa and about 70 kDa, between about 70 kDa and about 80 kDa, and between about 80 kDa, about 90 kDa. As used herein, the term "about" used in the context of molecular weight of an insecticidal polypeptide means±2 kilodaltons.

In some embodiments the insecticidal polypeptides of the disclosure have a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, but are not limited to solubility, folding, stability, and digestibility. In some embodiments the insecticidal polypeptides of the disclosure have increased digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments variants include polypeptides that differ in amino acid sequence due to mutagenesis. Variant proteins encompassed by the disclosure are biologically active, that is they continue to possess the desired biological activity (i.e. pesticidal activity) of the native protein. In some embodiment the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

In another aspect an insecticidal polypeptide of the disclosure may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.,* 271: 22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterfication reaction between the two termini to form a branched ester or thioester intermediate and peptide bond cleavage coupled to cyclization of the intein C-terminal asparagine to free the intein (Evans, et al., (2000) *J. Biol. Chem.,* 275: 9091-9094. The elucidation of the mechanism of protein splicing has led to a number of intein-based applications (Comb, et al., U.S. Pat. No. 5,496,714; Comb, et al., U.S. Pat. No. 5,834,247; Camarero and Muir, (1999) *J. Amer. Chem. Soc.* 121:5597-5598; Chong, et al., (1997) *Gene* 192:271-281, Chong, et al., (1998) *Nucleic Acids Res.* 26:5109-5115; Chong, et al., (1998) *J. Biol. Chem.* 273: 10567-10577; Cotton, et al., (1999) *J. Am. Chem. Soc.* 121:1100-1101; Evans, et al., (1999) *J. Biol. Chem.* 274: 18359-18363; Evans, et al., (1999) *J. Biol. Chem.* 274:3923-3926; Evans, et al., (1998) *Protein Sci.* 7:2256-2264; Evans, et al., (2000) *J. Biol. Chem.* 275:9091-9094; Iwai and Pluckthun, (1999) *FEBS Lett.* 459:166-172; Mathys, et al., (1999) *Gene* 231:1-13; Mills, et al., (1998) *Proc. Natl. Acad. Sci. USA* 95:3543-3548; Muir, et al., (1998) *Proc. Natl. Acad. Sci. USA* 95:6705-6710; Otomo, et al., (1999) *Biochemistry* 38:16040-16044; Otomo, et al., (1999) *J. Biolmol. NMR* 14:105-114; Scott, et al., (1999) *Proc. Natl. Acad. Sci. USA* 96:13638-13643; Severinov and Muir, (1998) *J. Biol. Chem.* 273:16205-16209; Shingledecker, et al., (1998) *Gene* 207:187-195; Southworth, et al., (1998) *EMBO J.* 17:918-926; Southworth, et al., (1999) *Biotechniques* 27:110-120; Wood, et al., (1999) *Nat. Biotechnol.* 17:889-892; Wu, et al., (1998a) *Proc. Natl. Acad. Sci. USA* 95:9226-9231; Wu, et al., (1998b) *Biochim Biophys Acta* 1387:422-432; Xu, et al., (1999) *Proc. Natl. Acad. Sci. USA* 96:388-393; Yamazaki, et al., (1998) *J. Am. Chem. Soc.,* 120:5591-5592). For the application of inteins in plant transgenes, see, Yang, et al., (*Transgene Res* 15:583-593 (2006)) and Evans, et al., (*Annu. Rev. Plant Biol.* 56:375-392 (2005)).

In another aspect an insecticidal polypeptide of the disclosure may be encoded by two separate genes where the intein of the precursor protein comes from the two genes, referred to as a split-intein, and the two portions of the precursor are joined by a peptide bond formation. This peptide bond formation is accomplished by intein-mediated trans-splicing. For this purpose, a first and a second expression cassette comprising the two separate genes further code for inteins capable of mediating protein trans-splicing. By trans-splicing, the proteins and polypeptides encoded by the first and second fragments may be linked by peptide bond formation. Trans-splicing inteins may be selected from the nucleolar and organellar genomes of different organisms including eukaryotes, archaebacteria and eubacteria. The nucleotide sequence coding for an intein may be split into a 5' and a 3' part that code for the 5' and the 3' part of the intein, respectively. Sequence portions not necessary for intein splicing (e.g. homing endonuclease domain) may be deleted. The intein coding sequence is split such that the 5' and the 3' parts are capable of trans-splicing. For selecting a suitable splitting site of the intein coding sequence, the considerations published by Southworth, et al., (1998) *EMBO J.* 17:918-926 may be followed. In constructing the first and the second expression cassette, the 5' intein coding sequence is linked to the 3' end of the first fragment coding for the N-terminal part of an insecticidal polypeptide of the disclosure and the 3' intein coding sequence is linked to the 5' end of the second fragment coding for the C-terminal part of an insecticidal polypeptide of the disclosure.

In general, the trans-splicing partners can be designed using any split intein, including any naturally-occurring or artificially-split split intein. Several naturally-occurring split inteins are known, for example: the split intein of the DnaE gene of *Synechocystis* sp. PCC6803 (see, Wu, et al., (1998) *Proc Natl Acad Sci USA.* 95(16):9226-31 and Evans, et al., (2000) *J. Biol Chem.* 275(13):9091-4 and of the DnaE gene from *Nostoc punctiforme* (see, Iwai, et al., (2006) *FEBS Lett.* 580(7):1853-8). Non-split inteins have been artificially split in the laboratory to create new split inteins, for example: the artificially split Ssp DnaB intein (see, Wu, et al., (1998) *Biochim Biophys Acta.* 1387:422-32) and split Sce VMA intein (see, Brenzel, et al., (2006) *Biochemistry.* 45(6):1571-8) and an artificially split fungal mini-intein (see, Elleuche, et al., (2007) *Biochem Biophys Res Commun.* 355(3):830-4). There are also intein databases available that catalogue known inteins (see for example the online-database available at: bioinformatics.weizmann.ac.il/~pietro/inteins/Inteinstable.html, which can be accessed on the world-wide web using the "www" prefix).

Naturally-occurring non-split inteins may have endonuclease or other enzymatic activities that can typically be removed when designing an artificially-split split intein. Such mini-inteins or minimized split inteins are well known in the art and are typically less than 200 amino acid residues long (see, Wu, et al., (1998) *Biochim Biophys Acta.* 1387:422-32). Suitable split inteins may have other purification enabling polypeptide elements added to their structure, provided that such elements do not inhibit the splicing of the split intein or are added in a manner that allows them to be removed prior to splicing. Protein splicing has been reported using proteins that comprise bacterial intein-like (BIL) domains (see, Amitai, et al., (2003) *Mol Microbiol.* 47:61-73) and hedgehog (Hog) auto-processing domains (the latter is combined with inteins when referred to as the Hog/intein superfamily or HINT family (see, Dassa, et al., (2004) *J. Biol Chem.* 279:32001-7) and domains such as these may also be used to prepare artificially-split inteins. In particular, non-splicing members of such families may be modified by molecular biology methodologies to introduce or restore splicing activity in such related species. Recent studies demonstrate that splicing can be observed when a N-terminal split intein component is allowed to react with a C-terminal split intein component not found in nature to be its "partner"; for example, splicing has been observed utilizing partners that have as little as 30 to 50% homology with the "natural" splicing partner (see, Dassa, et al., (2007) *Biochemistry.* 46(1):322-30). Other such mixtures of disparate split intein partners have been shown to be unreactive one with another (see, Brenzel, et al., (2006) *Biochemistry.* 45(6):1571-8). However, it is within the ability of a person skilled in the relevant art to determine whether a particular pair of polypeptides is able to associate with each other to provide a functional intein, using routine methods and without the exercise of inventive skill.

In another aspect an insecticidal polypeptide of the disclosure is a circular permuted variant. The development of recombinant DNA methods has made it possible to study the effects of sequence transposition on protein folding, structure, and function. The approach used in creating new sequences resembles that of naturally occurring pairs of proteins that are related by linear reorganization of their amino acid sequences (Cunningham, et al., (1979) *Proc. Natl. Acad. Sci. U.S.A.* 76:3218-3222; Teather and Erfle, (1990) *J. Bacteriol.* 172:3837-3841; Schimming, et al., (1992) *Eur. J. Biochem.* 204:13-19; Yamiuchi and Minamikawa, (1991) *FEBS Lett.* 260:127-130; MacGregor, et al., (1996) *FEBS Lett.* 378:263-266). The first in vitro application of this type of rearrangement to proteins was described by Goldenberg and Creighton (*J. Mol. Biol.* 165:407-413, 1983). In creating a circular permuted variant a new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus and the new sequence continues with the same sequence as the original until it reaches a point that is at or near the amino acid that was N-terminal to the breakpoint site of the original sequence, this residue forming the new C-terminus of the chain. The length of the amino acid sequence of the linker can be selected empirically or with guidance from structural information or by using a combination of the two approaches. When no structural information is available, a small series of linkers can be prepared for testing using a design whose length is varied in order to span a range from 0 to 50 Å and whose sequence is chosen in order to be consistent with surface exposure (hydrophilicity, Hopp and Woods, (1983) *Mol. Immunol.* 20:483-489; Kyte and Doolittle, (1982) *J. Mol. Biol.* 157:105-132; solvent exposed surface area, Lee and Richards, (1971) *J. Mol. Biol.* 55:379-400) and the ability to adopt the necessary conformation without deranging the configuration of the pesticidal polypeptide (conformationally flexible; Karplus and Schulz, (1985) *Naturwissenschaften* 72:212-213). Assuming an average of translation of 2.0 to 3.8 Å per residue, this would mean the length to test would be between 0 to 30 residues, with 0 to 15 residues being the preferred range. Those skilled in the art will recognize that there are many such sequences that vary in length or composition that can serve as linkers with the primary consideration being that they be neither excessively long nor short (cf., Sandhu, (1992) *Critical Rev. Biotech.* 12:437-462); if they are too long, entropy effects will likely destabilize the three-dimensional fold, and may also make folding kinetically impractical, and if they are too short, they will likely destabilize the molecule because of torsional or steric strain. Those skilled in the analysis of protein structural information will recognize that using the distance between the chain ends, defined as the distance between the c-alpha carbons, can be used to define the length of the sequence to be used or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers; or optionally a combination of the original sequence and new sequence having the appropriate total length may be used. Sequences of pesticidal polypeptides capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence. Methods are known to those skilled in the art to obtain and interpret three-dimensional structural information using x-ray diffraction of single protein Crystals or nuclear magnetic resonance spectroscopy of protein solutions. Examples of structural information that are relevant to the identification of breakpoint regions include the location and type of protein secondary structure (alpha and 3-10 helices, parallel and anti-parallel beta sheets, chain reversals and turns, and loops; Kabsch and Sander, (1983) *Biopolymers* 22:2577-2637; the degree of solvent exposure of amino acid residues, the extent and type of interactions of residues with one another (Chothia, (1984) *Ann. Rev. Biochem.* 53:537-572) and the static and dynamic distribution of conformations along the polypeptide chain (Alber and Mathews, (1987) *Methods Enzymol.* 154:511-533). In some cases additional information is known about solvent exposure of residues; one example is a site of post-translational attachment of carbohydrate which is necessarily on the surface of the protein. When experimental structural information is not available or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile and Salvatore, (1993) *Eur. J. Biochem.* 218:603-621). Thus using either the experimentally derived structural information or predictive methods (e.g., Srinivisan and Rose, (1995) *Proteins: Struct., Funct. &Genetics* 22:81-99) the parental amino acid sequence is inspected to classify regions according to whether or not they are integral to the maintenance of secondary and tertiary structure. The occurrence of sequences within regions that are known to be involved in periodic secondary structure (alpha and 3-10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region. Polynucleotides encoding circular permuted insecticidal polypeptides of the disclosure with new N-terminus/C-terminus which contain a linker region separating the original C-terminus and N-terminus can be made essentially following the method described in Mullins, et al., (1994) *J. Am. Chem. Soc.* 116:5529-5533. Multiple steps of polymerase chain reaction (PCR) amplifications are used to rearrange the DNA sequence encoding the primary amino acid sequence of the protein. Polynucleotides encoding circular permuted insecticidal polypeptides of the disclosure with new N-terminus/C-terminus which contain a linker region separating the original C-terminus and N-terminus can be made based on the tandem-duplication method described in Horlick, et al., (1992) *Protein Eng.* 5:427-431. Polymerase chain reaction (PCR) amplification of the new N-terminus/C-terminus genes is performed using a tandemly duplicated template DNA.

In another aspect fusion proteins are provided that include within its amino acid sequence an amino acid sequence comprising an insecticidal polypeptide of the disclosure. Methods for design and construction of fusion proteins, and polynucleotides encoding the same, are known to those of skill in the art. Polynucleotides encoding an insecticidal polypeptide of the disclosure may be fused to signal sequences which will direct the localization of the insecticidal polypeptide of the disclosure to insecticidal polypeptide of the embodiments from a prokaryotic or eukaryotic cell. For example, in *E. coli*, one may wish to direct the expression of the protein to the periplasmic space. Examples of signal sequences or proteins (or fragments thereof) to which the insecticidal polypeptide of the disclosure may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs® (240 County Road, Ipswich, Mass. 01938-2723). In a specific embodiment, the insecticidal polypeptide of the disclosure may be fused to the pelB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art (see, U.S. Pat. No. 7,193,133). Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the insecticidal polypeptide of the disclosure to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine codon of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) Gene 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29):15104-9.

In some embodiments fusion proteins provided comprise an insecticidal polypeptide of the disclosure, and an insecticidal polypeptide joined by an amino acid linker.

In some embodiments fusion proteins are provided represented by a formula selected from the group consisting of:

$$R^1\text{-}L\text{-}R^2, R^2\text{-}L\text{-}R^1, R^1\text{-}R^2 \text{ or } R^2\text{-}R^1$$

wherein $R^1$ is an insecticidal polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$ or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker comprises the amino acids EEKKN (SEQ ID NO: 83) from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

In another aspect chimeric insecticidal polypeptides are provided that are created through joining two or more portions of insecticidal polypeptides genes of disclosure, which originally encoded separate insecticidal proteins to create a chimeric gene. The translation of the chimeric gene results in a single chimeric insecticidal polypeptide with regions, motifs or domains derived from each of the original polypeptides.

It is recognized that DNA sequences may be altered by various methods, and that these alterations may result in DNA sequences encoding proteins with amino acid sequences different than that encoded by the wild-type (or native) pesticidal protein. In some embodiments an insecticidal polypeptide of the disclosure may be altered in various ways including amino acid substitutions, deletions, truncations and insertions of one or more amino acids, including up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or more amino acid substitutions, deletions and/or insertions or combinations thereof compared to any one of SEQ ID NOs: 42-82. In some embodiments an insecticidal polypeptide of the disclosure comprises the deletion of 1, 2, 3, 4, 5, 6, 7, 8, 9, 10, 11, 12, 13, 14, 15 or more amino acids from the N-terminus and/or C-terminus of the insecticidal polypeptide of the disclosure.

Methods for such manipulations are generally known in the art. For example, amino acid sequence variants of an insecticidal polypeptide of the disclosure can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of an insecticidal polypeptide of the disclosure to confer pesticidal activity may be improved by the use of such techniques upon the compositions of this disclosure.

For example, conservative amino acid substitutions may be made at one or more, predicted, nonessential amino acid residues. A "nonessential" amino acid residue is a residue that can be altered from the wild-type sequence of an insecticidal polypeptide of the disclosure without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cysteine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologs). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment of the homologs). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, (1982) *J Mol Biol.* 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0);

methionine (−1.3); valine (−1.5); leucine (−1.8); isoleucine (−1.8); tyrosine (−2.3); phenylalanine (−2.5); tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different insecticidal polypeptide of the disclosure coding regions can be used to create a new insecticidal polypeptide of the disclosure possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered insecticidal polypeptides of the disclosure. Domains may be swapped between insecticidal polypeptides of the disclosure, resulting in hybrid or chimeric toxins with improved insecticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-20930; Rang, et al., 91999) *Appl. Environ. Microbiol.* 65:2918-2925).

Figure 1C:

Alignment of homologs of the insectidal polypeptide (FIG. 1) allows for identification of residues that are highly conserved among homologs in these families.

Compositions

Compositions comprising the insecticidal polypeptides of the present disclosure are also envisioned. Compositions comprising a IPD078-1, IPD078-2, IPD084, IPD086-1, IPD086-2, IPD087, and/or IPD089 polypeptide of the disclosure are contemplated. In some embodiments the compositions comprise an insecticidally effective concentration of a IPD078-1, IPD078-2, IPD084, IPD086-1, IPD086-2, IPD087, and/or IPD089 polypeptide of the disclosure. In a further embodiment, the compositions comprise a combination of one or more of the IPD078-1, IPD078-2, IPD084, IPD086-1, IPD086-2, IPD087, and/or IPD089 polypeptides of the disclosure. In one embodiment, the compositions comprise a IPD078-1 and a IPD078-2, or a IPD086-1 and IPD086-2 polypeptide of the disclosure. In some embodiments the composition further comprises an agriculturally acceptable carrier.

Antibodies

Antibodies to an insecticidal polypeptide of the disclosure of the embodiments or to variants or fragments thereof are also encompassed. The antibodies of the disclosure include polyclonal and monoclonal antibodies as well as fragments thereof which retain their ability to bind to insecticidal proteins found in the insect gut. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies to the insecticidal polypeptides of the disclosure or antigen-binding portions thereof can be produced by a variety of techniques, including conventional monoclonal antibody methodology, for example the standard somatic cell hybridization technique of Kohler and Milstein, (1975) Nature 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an insecticidal polypeptide of the disclosure as antigens.

A kit for detecting the presence of an insecticidal polypeptide of the disclosure or detecting the presence of a nucleotide sequence encoding an insecticidal polypeptide of the disclosure, in a sample is provided. In one embodiment, the kit provides antibody-based reagents for detecting the presence of an insecticidal polypeptide of the disclosure in a tissue sample. In another embodiment, the kit provides labeled nucleic acid probes useful for detecting the presence of one or more polynucleotides encoding an insecticidal polypeptide(s) of the disclosure. The kit is provided along with appropriate reagents and controls for carrying out a detection method, as well as instructions for use of the kit.

Receptor Identification and Isolation

Receptors to the insecticidal polypeptide of the embodiments or to variants or fragments thereof, are also encompassed. Methods for identifying receptors are well known in the art (see, Hofmann, et. al., (1988) *Eur. J. Biochem.* 173:85-91; Gill, et al., (1995) *J. Biol. Chem.* 27277-27282) can be employed to identify and isolate the receptor that recognizes the insecticidal polypeptides of the disclosure using the brush-border membrane vesicles from susceptible insects. In addition to the radioactive labeling method listed in the cited literature, insecticidal polypeptide can be labeled with fluorescent dye and other common labels such as streptavidin. Brush-border membrane vesicles (BBMV) of susceptible insects such as soybean looper and stink bugs can be prepared according to the protocols listed in the references and separated on SDS-PAGE gel and blotted on suitable membrane. Labeled insecticidal polypeptides of the disclosure can be incubated with blotted membrane of BBMV and labeled insecticidal polypeptides of the disclosure can be identified with the labeled reporters. Identification of protein band(s) that interact with the insecticidal polypeptides of the disclosure can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the insecticidal polypeptides of the disclosure. Receptor function for insecticidal activity by the insecticidal polypeptides of the disclosure can be verified by accomplished by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the insecticidal polypeptide gene sequence to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (the ubiquitin intron (i.e., the maize ubiquitin intron 1 (see, for example, NCBI sequence S94464; Christensen and Quail (1996) *Transgenic Res.* 5:213-218; Christensen et al. (1992) *Plant Molecular Biology* 18:675-689)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96), the maize AdhI intron (Kyozuka et al. (1991) *Mol. Gen. Genet.* 228:40-48; Kyozuka et al. (1990) *Maydica* 35:353-357) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gown, (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray, et al., supra. Methods are available in the art for synthesizing plant-preferred genes. See, for example, Murray, et al., (1989) *Nucleic Acids Res.* 17:477-498, and Liu H et al. *Mol Bio Rep* 37:677-684, 2010. A *Zea maize* codon usage table can be also found at kazusa.or.jp/codon/cgi-bin/showcodon.cgi?species=4577, which can be accessed using the www prefix, and Liu H et al. *Mol Bio Rep* 37:677-684, 2010). A *Glycine max* codon usage table can also be found at kazusa.orjp/codon/cgi-bin/showcodon.cgi?species=3847&aa=1&style=N, which can be accessed using the www prefix.

In some embodiments the recombinant nucleic acid molecule encoding an insecticidal polypeptide of the disclosure has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector as intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. *Plant Cell* 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research,* 78:249-264, 2003. In particular, Table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present disclosure.

Suitable chloroplast transit peptides (CTP) are well known to one skilled in the art also include chimeric CTPs comprising but not limited to, an N-terminal domain, a central domain or a C-terminal domain from a CTP from *Oryza sativa* 1-deoxy-D xyulose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type (US Patent Application Publication 2012/0304336). Chloroplast transit peptides of US Patent Publications US20130205440A1, US20130205441A1 and US20130210114A1.

The insecticidal polypeptide gene to be targeted to the chloroplast may be optimized for expression in the chloroplast to account for differences in codon usage between the plant nucleus and this organelle. In this manner, the nucleic acids of interest may be synthesized using chloroplast-preferred codons.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611. Suitable constitutive promoters also include promoters that have strong expression in nearly all tissues but have low expression in pollen, including but not limited to: Banana Streak Virus (*Acuminata* Yunnan) promoters (BSV(AY)) disclosed in US patent U.S. Pat. No. 8,338,662; Banana Streak Virus (*Acuminata* Vietnam) promoters (BSV(AV)) disclosed in US patent U.S. Pat. No. 8,350,121; and Banana Streak Virus (Mysore) promoters (BSV(MYS)) disclosed in US patent U.S. Pat. No. 8,395,022.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156).

Tissue-preferred promoters can be utilized to target enhanced insecticidal polypeptide expression within a particular plant tissue. Tissue-preferred promoters include those discussed in Yamamoto, et al., (1997) *Plant J* 12(2)255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US Patent Application US20130117883. Root-preferred sorghum (*Sorghum bicolor*) RCc3 promoters are disclosed in US Patent Application US20120210463.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1093), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed. In dicots, seed specific promoters include but are not limited to seed coat promoter from *Arabidopsis*, pBAN; and the early seed promoters from *Arabidopsis, p*26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA*

86:5400-5404; Fuerst, et al., (1989) *Proc. Natl. Acad. Sci. USA* 86:2549-2553; Deuschle, et al., (1990) *Science* 248: 480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724.

The above list of selectable marker genes is not meant to be limiting. Any selectable marker gene can be used in the embodiments.

DNA Constructs

DNA constructs comprising a polynucleotide encoding an insecticidal polypeptide of the disclosure are encompassed. In some embodiments the DNA construct comprises a polynucleotide encoding a IPD078-1, IPD078-2, IPD084, IPD086-1, IPD086-2, IPD087, or a IPD089 polypeptide operably linked to a heterologous regulatory element. In some embodiments the DNA construct comprises a polynucleotide of one or more of SEQ ID NOs: 1-42 that encodes one or more IPD078-1, IPD078-2, IPD084, IPD086-1, IPD086-2, IPD087, or IPD089 polypeptides of SEQ ID NOs: 43-82 In some embodiments the DNA construct comprises a non-genomic nucleic acid molecule encoding a IPD078-1, IPD078-2, IPD084, IPD086-1, IPD086-2, IPD087, or IPD089 polypeptide. In some embodiments the DNA construct comprises a polynucleotide encoding a IPD078-1, IPD078-2, IPD084, IPD086-1, IPD086-2, IPD087, or IPD089 polypeptide sufficiently homologous to the amino acid sequence of one or more of SEQ ID NOs: 43-82, and which has insecticidal activity.

In some embodiments the DNA construct comprises a polynucleotide encoding a IPD078-1, IPD078-2, IPD084, IPD086-1, IPD086-2, IPD087, or IPD089 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to one or more polypeptide sequences of SEQ ID NOs: 43-82, and which has insecticidal activity. In some embodiments the DNA construct comprises a polynucleotide encoding a IPD078-1, IPD078-2, IPD084, IPD086-1, IPD086-2, IPD087, or IPD089 polypeptide having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to one or more polypeptide sequences of SEQ ID NOs: 43-82, and which has insecticidal activity.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotides or polypeptides into plants are known in the art including, but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Biotechnology* 6:923-926) and Led transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

In specific embodiments, the sequences of the embodiments can be provided to a plant using a variety of transient transformation methods. Such transient transformation methods include, but are not limited to, the introduction of the insecticidal polypeptide of the disclosure or insecticidally active variants and fragments thereof directly into the plant or the introduction of an insecticidal polypeptide of the disclosure into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784. Alternatively, the polynucleotide(s) encoding the insecticidal polypeptide(s) of the disclosure can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853. Briefly, the polynucleotide of the embodiments can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired insecticidal polypeptide. It is also recognized that such a viral polyprotein, comprising at least a portion of the amino acid sequence of an insecticidal polypeptide of the disclosure of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367 and 5,316,931.

Methods for transformation of chloroplasts are known in the art. See, for example, Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), *hydrangea* (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the embodiments include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (Dactyl's *glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canna*); weeping alkaligrass (*Puccinellia distans*); western wheatgrass (*Agropyron smithii*); Bermuda grass (*Cynodon* spp.); St. Augustine grass (*Stenotaphrum secundatum*); *zoysia* grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore *paspalum* (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mungbean, lima bean, fava bean, lentils, chickpea, etc.

Methods to Introduce Genome Editing Technologies into Plants

In an aspect, the disclosed polynucleotides encoding one or more IDP IPD078-1, IPD078-2, IPD084, IPD086-1, IPD086-2, IPD087, and IPD089 polypeptides compositions can be introduced into the genome of a plant using genome editing technologies, or previously introduced polynucleotides encoding one or more IDP IPD078-1, IPD078-2, IPD084, IPD086-1, IPD086-2, IPD087, and/or IPD089 polypeptides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In another aspect, where the disclosed polynucleotides encoding one or more IDP IPD078-1, IPD078-2, IPD084, IPD086-1, IPD086-2, IPD087, and/or IPD089 polypeptides has previously been introduced into a genome, genome editing technologies may be used to alter or modify the introduced polynucleotide sequence. Site specific modifications that can be introduced into the disclosed polynucleotides encoding one or more IDP IPD078-1, IPD078-2, IPD084, IPD086-1, IPD086-2, IPD087, and IPD089 polypeptides include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed polynucleotides encoding one or more IDP IPD078-1, IPD078-2, IPD084, IPD086-1, IPD086-2, IPD087, and/or IPD089 polypeptide compositions disclosed herein within the genome of a plant, in order to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Transgenic Plants

Transgenic plants or plant cells comprising a polynucleotide encoding an insecticidal polypeptide are also encompassed by the disclosure. Transgenic plants or plant cells comprising one or more polynucleotides encoding one or more IPD078-1, IPD078-2, IPD084, IPD086-1, IPD086-2, IPD087, or IPD089 polypeptides are encompassed by the disclosure. In some embodiments the transgenic plant or plant cell comprises one or more polynucleotides of SEQ ID NOs: 1-42 that encodes one or more IPD078-1, IPD078-2, IPD084, IPD086-1, IPD086-2, IPD087, or IPD089 polypeptides of SEQ ID NOs: 43-82 (see Table 2). In some embodiments the transgenic plant or plant cell comprises a non-genomic nucleic acid molecule encoding one or more IPD078-1, IPD078-2, IPD084, IPD086-1, IPD086-2, IPD087, or IPD08 polypeptides. In some embodiments the transgenic plant or plant cell comprises one or more polynucleotides encoding one or more IPD078-1, IPD078-2, IPD084, IPD086-1, IPD086-2, IPD087, or IPD08 polypeptide(s) sufficiently homologous to the amino acid sequence of one or more polypeptides of SEQ ID NOs: 43-82, and which has insecticidal activity. In some embodiments the sequence homology is against the full length sequence of the IPD078-1, IPD078-2, IPD084, IPD086-1, IPD086-2, IPD087, or IPD08 polypeptide.

In some embodiments the transgenic plant or plant cell comprises one or more polynucleotides encoding one or more IPD078-1, IPD078-2, IPD084, IPD086-1, IPD086-2, IPD087, or IPD08 polypeptides having at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to one or more polypeptides of SEQ ID NOs: 43-82, and which has insecticidal activity.

Stacking of Traits in Transgenic Plant

Transgenic plants may comprise a stack of one or more polynucleotides encoding insecticidal polypeptides disclosed herein with one or more additional polynucleotides encoding insecticidal polypeptides and/or polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853.

In some embodiments the polynucleotides encoding the insecticidal polypeptides disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to:

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262: 1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas* protegees strain CHAO and Pf-5 (previously *fluorescens*) (Pechy-Tarr, (2008) *Environmental Microbiology* 10:2368-2386: GenBank Accession No. EU400157); from *Pseudomonas Taiwanensis* (Liu, et al., (2010) 1 *Agric. Food Chem.* 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; a PIP-1 polypeptide of US Patent Publication Number US2014-0007297-A1; an AfIP-1A and/or AfIP-1B polypeptides of US Patent Publication Number US2014-0033361; a PHI-4 polypeptides of U.S. Ser. No. 13/839,702; PIP-47 polypeptides of PCT Serial Number PCT/US14/51063; a PHI-4 polypeptide of US patent Publication US20140274885 or PCT Patent Publication WO2014/150914; a PIP-72 polypeptide of PCT Serial Number PCT/US14/55128; the insecticidal proteins of PCT Serial Number PCT/US14/49923; and β-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51, Cry52, Cry 53, Cry 54, Cry55, Cry56, Cry57, Cry58, Cry59. Cry60, Cry61, Cry62, Cry63, Cry64, Cry65, Cry66, Cry67, Cry68, Cry69, Cry70, Cry71 and Cry72 classes of δ-endotoxin genes and the *B. thuringiensis* cytolytic Cyt1 and Cyt2 genes. Members of these classes of *B. thuringiensis* insecticidal proteins include, but are not limited to Cry1Aa1 (Accession #AAA22353); Cry1Aa2 (Accession #Accession #AAA22552); Cry1Aa3 (Accession #BAA00257); Cry1Aa4 (Accession #CAA31886); Cry1Aa5 (Accession #BAA04468); Cry1Aa6 (Accession #AAA86265); Cry1Aa7 (Accession #AAD46139); Cry1Aa8 (Accession #I26149); Cry1Aa9 (Accession #BAA77213); Cry1Aa10 (Accession #AAD55382); Cry1Aa11 (Accession #CAA70856); Cry1Aa12 (Accession #AAP80146); Cry1Aa13 (Accession #AAM44305); Cry1Aa14 (Accession #AAP40639); Cry1Aa15 (Accession #AAY66993); Cry1Aa16 (Accession #HQ439776); Cry1Aa17 (Accession #HQ439788); Cry1Aa18 (Accession #HQ439790); Cry1Aa19 (Accession #HQ685121); Cry1Aa20 (Accession #JF340156); Cry1Aa21 (Accession #JN651496); Cry1Aa22 (Accession #KC158223); Cry1Ab1 (Accession #AAA22330); Cry1Ab2 (Accession #AAA22613); Cry1Ab3 (Accession #AAA22561); Cry1Ab4 (Accession #BAA00071); Cry1Ab5 (Accession #CAA28405); Cry1Ab6 (Accession #AAA22420); Cry1Ab7 (Accession #CAA31620); Cry1Ab8 (Accession #AAA22551); Cry1Ab9 (Accession #CAA38701); Cry1Ab10 (Accession #A29125); Cry1Ab11 (Accession #112419); Cry1Ab12 (Accession #AAC64003); Cry1Ab13 (Accession #AAN76494); Cry1Ab14 (Accession #AAG16877); Cry1Ab15 (Accession #AAO13302); Cry1Ab16 (Accession #AAK55546); Cry1Ab17 (Accession #AAT46415); Cry1Ab18 (Accession #AAQ88259); Cry1Ab19 (Accession #AAW31761); Cry1Ab20 (Accession #ABB72460); Cry1Ab21 (Accession #ABS18384); Cry1Ab22 (Accession #ABW87320); Cry1Ab23 (Accession #HQ439777); Cry1Ab24 (Accession #HQ439778); Cry1Ab25 (Accession #HQ685122); Cry1Ab26 (Accession #HQ847729); Cry1Ab27 (Accession #JN135249); Cry1Ab28 (Accession #JN135250); Cry1Ab29 (Accession #JN135251); Cry1Ab30 (Accession #JN135252); Cry1Ab31 (Accession #JN135253); Cry1Ab32 (Accession #JN135254); Cry1Ab33 (Accession #AAS93798); Cry1Ab34 (Accession #KC156668); Cry1Ab-like (Accession #AAK14336); Cry1Ab-like (Accession #AAK14337); Cry1Ab-like (Accession #AAK14338); Cry1Ab-like (Accession #ABG88858); Cry1Ac1 (Accession #AAA22331); Cry1Ac2 (Accession #AAA22338); Cry1Ac3 (Accession #CAA38098); Cry1Ac4 (Accession #AAA73077); Cry1Ac5 (Accession #AAA22339); Cry1Ac6 (Accession #AAA86266); Cry1Ac7 (Accession #AAB46989); Cry1Ac8 (Accession #AAC44841); Cry1Ac9 (Accession #AAB49768); Cry1Ac10 (Accession #CAA05505); Cry1Ac11 (Accession #CAA10270); Cry1Ac12 (Accession #I12418); Cry1Ac13 (Accession #AAD38701); Cry1Ac14 (Accession #AAQ06607); Cry1Ac15 (Accession #AAN07788); Cry1Ac16 (Accession #AAU87037); Cry1Ac17 (Accession #AAX18704); Cry1Ac18 (Accession #AAY88347); Cry1Ac19 (Accession #ABD37053); Cry1Ac20 (Accession #ABB89046); Cry1Ac21 (Accession #AAY66992); Cry1Ac22 (Accession #ABZ01836);

Cry1Ac23 (Accession #CAQ30431); Cry1Ac24 (Accession #ABL01535); Cry1Ac25 (Accession #FJ513324); Cry1Ac26 (Accession #FJ617446); Cry1Ac27 (Accession #FJ617447); Cry1Ac28 (Accession #ACM90319); Cry1Ac29 (Accession #DQ438941); Cry1Ac30 (Accession #GQ227507); Cry1Ac31 (Accession #GU446674); Cry1Ac32 (Accession #HM061081); Cry1Ac33 (Accession #GQ866913); Cry1Ac34 (Accession #HQ230364); Cry1Ac35 (Accession #JF340157); Cry1Ac36 (Accession #JN387137); Cry1Ac37 (Accession #JQ317685); Cry1Ad1 (Accession #AAA22340); Cry1Ad2 (Accession #CAA01880); Cry1Ae1 (Accession #AAA22410); Cry1Af1 (Accession #AAB82749); Cry1Ag1 (Accession #AAD46137); Cry1Ah1 (Accession #AAQ14326); Cry1Ah2 (Accession #ABB76664); Cry1Ah3 (Accession #HQ439779); Cry1Ai1 (Accession #AA039719); Cry1Ai2 (Accession #HQ439780); Cry1A-like (Accession #AAK14339); Cry1Ba1 (Accession #CAA29898); Cry1Ba2 (Accession #CAA65003); Cry1Ba3 (Accession #AAK63251); Cry1Ba4 (Accession #AAK51084); Cry1Ba5 (Accession #ABO20894); Cry1Ba6 (Accession #ABL60921); Cry1Ba7 (Accession #HQ439781); Cry1Bb1 (Accession #AAA22344); Cry1Bb2 (Accession #HQ439782); Cry1Bc1 (Accession #CAA86568); Cry1Bd1 (Accession #AAD10292); Cry1Bd2 (Accession #AAM93496); Cry1Be1 (Accession #AAC32850); Cry1Be2 (Accession #AAQ52387); Cry1Be3 (Accession #ACV96720); Cry1Be4 (Accession #HM070026); Cry1Bf1 (Accession #CAC50778); Cry1Bf2 (Accession #AAQ52380); Cry1Bg1 (Accession #AAO39720); Cry1Bh1 (Accession #HQ589331); Cry1Bi1 (Accession #KC156700); Cry1Ca1 (Accession #CAA30396); Cry1Ca2 (Accession #CAA31951); Cry1Ca3 (Accession #AAA22343); Cry1Ca4 (Accession #CAA01886); Cry1Ca5 (Accession #CAA65457); Cry1Ca6 [1] (Accession #AAF37224); Cry1Ca7 (Accession #AAG50438); Cry1Ca8 (Accession #AAM00264); Cry1Ca9 (Accession #AAL79362); Cry1Ca10 (Accession #AAN16462); Cry1Ca11 (Accession #AAX53094); Cry1Ca12 (Accession #HM070027); Cry1Ca13 (Accession #HQ412621); Cry1Ca14 (Accession #JN651493); Cry1Cb1 (Accession #M97880); Cry1Cb2 (Accession #AAG35409); Cry1Cb3 (Accession #ACD50894); Cry1Cb-like (Accession #AAX63901); Cry1Da1 (Accession #CAA38099); Cry1Da2 (Accession #I76415); Cry1Da3 (Accession #HQ439784); Cry1Db1 (Accession #CAA80234); Cry1Db2 (Accession #AAK48937); Cry1Dc1 (Accession #ABK35074); Cry1Ea1 (Accession #CAA37933); Cry1Ea2 (Accession #CAA39609); Cry1Ea3 (Accession #AAA22345); Cry1Ea4 (Accession #AADO4732); Cry1Ea5 (Accession #A15535); Cry1Ea6 (Accession #AAL50330); Cry1Ea7 (Accession #AAW72936); Cry1Ea8 (Accession #ABX11258); Cry1Ea9 (Accession #HQ439785); Cry1Ea10 (Accession #ADR00398); Cry1Ea11 (Accession #JQ652456); Cry1Eb1 (Accession #AAA22346); Cry1Fa1 (Accession #AAA22348); Cry1Fa2 (Accession #AAA22347); Cry1Fa3 (Accession #HM070028); Cry1Fa4 (Accession #HM439638); Cry1Fb1 (Accession #CAA80235); Cry1Fb2 (Accession #BAA25298); Cry1Fb3 (Accession #AAF21767); Cry1Fb4 (Accession #AAC10641); Cry1Fb5 (Accession #AAO13295); Cry1Fb6 (Accession #ACD50892); Cry1Fb7 (Accession #ACD50893); Cry1Gal (Accession #CAA80233); Cry1Ga2 (Accession #CAA70506); Cry1Gb1 (Accession #AAD10291); Cry1Gb2 (Accession #AAO13756); Cry1Gc1 (Accession #AAQ52381); Cry1Hal (Accession #CAA80236); Cry1Hb1 (Accession #AAA79694); Cry1Hb2 (Accession #HQ439786); Cry1H-like (Accession #AAF01213); Cry1Ia1 (Accession #CAA44633); Cry1Ia2 (Accession #AAA22354); Cry1Ia3 (Accession #AAC36999); Cry1Ia4 (Accession #AAB00958); Cry1Ia5 (Accession #CAA70124); Cry1Ia6 (Accession #AAC26910); Cry1Ia7 (Accession #AAM73516); Cry1Ia8 (Accession #AAK66742); Cry1Ia9 (Accession #AAQ08616); Cry1Ia10 (Accession #AAP86782); Cry1Ia11 (Accession #CAC85964); Cry1Ia12 (Accession #AAV53390); Cry1Ia13 (Accession #ABF83202); Cry1Ia14 (Accession #ACG63871); Cry1Ia15 (Accession #FJ617445); Cry1Ia16 (Accession #FJ617448); Cry1Ia17 (Accession #GU989199); Cry1Ia18 (Accession #ADK23801); Cry1Ia19 (Accession #HQ439787); Cry1Ia20 (Accession #JQ228426); Cry1Ia21 (Accession #JQ228424); Cry1Ia22 (Accession #JQ228427); Cry1Ia23 (Accession #JQ228428); Cry1Ia24 (Accession #JQ228429); Cry1Ia25 (Accession #JQ228430); Cry1Ia26 (Accession #JQ228431); Cry1Ia27 (Accession #JQ228432); Cry1Ia28 (Accession #JQ228433); Cry1Ia29 (Accession #JQ228434); Cry1Ia30 (Accession #JQ317686); Cry1Ia31 (Accession #JX944038); Cry1Ia32 (Accession #JX944039); Cry1Ia33 (Accession #JX944040); Cry1Ib1 (Accession #AAA82114); Cry1Ib2 (Accession #ABW88019); Cry1Ib3 (Accession #ACD75515); Cry1Ib4 (Accession #HM051227); Cry1Ib5 (Accession #HM070028); Cry1Ib6 (Accession #ADK38579); Cry1Ib7 (Accession #JN571740); Cry1Ib8 (Accession #JN675714); Cry1Ib9 (Accession #JN675715); Cry1Ib10 (Accession #JN675716); Cry1Ib11 (Accession #JQ228423); Cry1Ic1 (Accession #AAC62933); Cry1Ic2 (Accession #AAE71691); Cry1Id1 (Accession #AAD44366); Cry1Id2 (Accession #JQ228422); Cry1Ie1 (Accession #AAG43526); Cry1Ie2 (Accession #HM439636); Cry1Ie3 (Accession #KC156647); Cry1Ie4 (Accession #KC156681); Cry1If1 (Accession #AAQ52382); Cry1Ig1 (Accession #KC156701); Cry1I-like (Accession #AAC31094); Cry1I-like (Accession #ABG88859); Cry1Ja1 (Accession #AAA22341); Cry1Ja2 (Accession #HM070030); Cry1Ja3 (Accession #JQ228425); Cry1Jb1 (Accession #AAA98959); Cry1Jc1 (Accession #AAC31092); Cry1Jc2 (Accession #AAQ52372); Cry1Jd1 (Accession #CAC50779); Cry1Ka1 (Accession #AAB00376); Cry1Ka2 (Accession #HQ439783); Cry1La1 (Accession #AAS60191); Cry1La2 (Accession #HM070031); Cry1Ma1 (Accession #FJ884067); Cry1Ma2 (Accession #KC156659); Cry1Na1 (Accession #KC156648); Cry1Nb1 (Accession #KC156678); Cry1-like (Accession #AAC31091); Cry2Aa1 (Accession #AAA22335); Cry2Aa2 (Accession #AAA83516); Cry2Aa3 (Accession #D86064); Cry2Aa4 (Accession #AAC04867); Cry2Aa5 (Accession #CAA10671); Cry2Aa6 (Accession #CAA10672); Cry2Aa7 (Accession #CAA10670); Cry2Aa8 (Accession #AAO13734); Cry2Aa9 (Accession #AA013750); Cry2Aa10 (Accession #AAQ04263); Cry2Aa11 (Accession #AAQ52384); Cry2Aa12 (Accession #ABI83671); Cry2Aa13 (Accession #ABL01536); Cry2Aa14 (Accession #ACF04939); Cry2Aa15 (Accession #JN426947); Cry2Ab1 (Accession #AAA22342); Cry2Ab2 (Accession #CAA39075); Cry2Ab3 (Accession #AAG36762); Cry2Ab4 (Accession #AAO13296); Cry2Ab5 (Accession #AAQ04609); Cry2Ab6 (Accession #AAP59457); Cry2Ab7 (Accession #AAZ66347); Cry2Ab8 (Accession #ABC95996); Cry2Ab9 (Accession #ABC74968); Cry2Ab10 (Accession #EF157306); Cry2Ab11 (Accession #CAM84575); Cry2Ab12 (Accession #ABM21764); Cry2Ab13 (Accession #ACG76120);

Cry2Ab14 (Accession #ACG76121); Cry2Ab15 (Accession #HM037126); Cry2Ab16 (Accession #GQ866914); Cry2Ab17 (Accession #HQ439789); Cry2Ab18 (Accession #JN135255); Cry2Ab19 (Accession #JN135256); Cry2Ab20 (Accession #JN135257); Cry2Ab21 (Accession #JN135258); Cry2Ab22 (Accession #JN135259); Cry2Ab23 (Accession #JN135260); Cry2Ab24 (Accession #JN135261); Cry2Ab25 (Accession #JN415485); Cry2Ab26 (Accession #JN426946); Cry2Ab27 (Accession #JN415764); Cry2Ab28 (Accession #JN651494); Cry2Ac1 (Accession #CAA40536); Cry2Ac2 (Accession #AAG35410); Cry2Ac3 (Accession #AAQ52385); Cry2Ac4 (Accession #ABC95997); Cry2Ac5 (Accession #ABC74969); Cry2Ac6 (Accession #ABC74793); Cry2Ac7 (Accession #CAL18690); Cry2Ac8 (Accession #CAM09325); Cry2Ac9 (Accession #CAM09326); Cry2Ac10 (Accession #ABN15104); Cry2Ac11 (Accession #CAM83895); Cry2Ac12 (Accession #CAM83896); Cry2Ad1 (Accession #AAF09583); Cry2Ad2 (Accession #ABC86927); Cry2Ad3 (Accession #CAK29504); Cry2Ad4 (Accession #CAM32331); Cry2Ad5 (Accession #CAO78739); Cry2Ae1 (Accession #AAQ52362); Cry2Af1 (Accession #ABO30519); Cry2Af2 (Accession #GQ866915); Cry2Ag1 (Accession #ACH91610); Cry2Ah1 (Accession #EU939453); Cry2Ah2 (Accession #ACL80665); Cry2Ah3 (Accession #GU073380); Cry2Ah4 (Accession #KC156702); Cry2Ai1 (Accession #FJ788388); Cry2Aj (Accession #); Cry2Ak1 (Accession #KC156660); Cry2Ba1 (Accession #KC156658); Cry3Aa1 (Accession #AAA22336); Cry3Aa2 (Accession #AAA22541); Cry3Aa3 (Accession #CAA68482); Cry3Aa4 (Accession #AAA22542); Cry3Aa5 (Accession #AAA50255); Cry3Aa6 (Accession #AAC43266); Cry3Aa7 (Accession #CAB41411); Cry3Aa8 (Accession #AAS79487); Cry3Aa9 (Accession #AAW05659); Cry3Aa10 (Accession #AAU29411); Cry3Aa11 (Accession #AAW82872); Cry3Aa12 (Accession #ABY49136); Cry3Ba1 (Accession #CAA34983); Cry3Ba2 (Accession #CAA00645); Cry3Ba3 (Accession #JQ397327); Cry3Bb1 (Accession #AAA22334); Cry3Bb2 (Accession #AAA74198); Cry3Bb3 (Accession #I15475); Cry3Ca1 (Accession #CAA42469); Cry4Aa1 (Accession #CAA68485); Cry4Aa2 (Accession #BAA00179); Cry4Aa3 (Accession #CAD30148); Cry4Aa4 (Accession #AFB18317); Cry4A-like (Accession #AAY96321); Cry4Ba1 (Accession #CAA30312); Cry4Ba2 (Accession #CAA30114); Cry4Ba3 (Accession #AAA22337); Cry4Ba4 (Accession #BAA00178); Cry4Ba5 (Accession #CAD30095); Cry4Ba-like (Accession #ABC47686); Cry4Ca1 (Accession #EU646202); Cry4Cb1 (Accession #FJ403208); Cry4Cb2 (Accession #FJ597622); Cry4Cc1 (Accession #FJ403207); Cry5Aa1 (Accession #AAA67694); Cry5Ab1 (Accession #AAA67693); Cry5Ac1 (Accession #I34543); Cry5Ad1 (Accession #ABQ82087); Cry5Ba1 (Accession #AAA68598); Cry5Ba2 (Accession #ABW88931); Cry5Ba3 (Accession #AFJ04417); Cry5Ca1 (Accession #HM461869); Cry5Ca2 (Accession #ZP_04123426); Cry5Da1 (Accession #HM461870); Cry5Da2 (Accession #ZP_04123980); Cry5Ea1 (Accession #HM485580); Cry5Ea2 (Accession #ZP_04124038); Cry6Aa1 (Accession #AAA22357); Cry6Aa2 (Accession #AAM46849); Cry6Aa3 (Accession #ABH03377); Cry6Ba1 (Accession #AAA22358); Cry7Aa1 (Accession #AAA22351); Cry7Ab1 (Accession #AAA21120); Cry7Ab2 (Accession #AAA21121); Cry7Ab3 (Accession #ABX24522); Cry7Ab4 (Accession #EU380678); Cry7Ab5 (Accession #ABX79555); Cry7Ab6 (Accession #ACI44005); Cry7Ab7 (Accession #ADB89216); Cry7Ab8 (Accession #GU145299); Cry7Ab9 (Accession #ADD92572); Cry7Ba1 (Accession #ABB70817); Cry7Bb1 (Accession #KC156653); Cry7Ca1 (Accession #ABR67863); Cry7Cb1 (Accession #KC156698); Cry7Da1 (Accession #ACQ99547); Cry7Da2 (Accession #HM572236); Cry7Da3 (Accession #KC156679); Cry7Ea1 (Accession #HM035086); Cry7Ea2 (Accession #HM132124); Cry7Ea3 (Accession #EEM19403); Cry7Fa1 (Accession #HM035088); Cry7Fa2 (Accession #EEM19090); Cry7Fb1 (Accession #HM572235); Cry7Fb2 (Accession #KC156682); Cry7Ga1 (Accession #HM572237); Cry7Ga2 (Accession #KC156669); Cry7Gb1 (Accession #KC156650); Cry7Gc1 (Accession #KC156654); Cry7Gd1 (Accession #KC156697); Cry7Ha1 (Accession #KC156651); Cry7Ia1 (Accession #KC156665); Cry7Ja1 (Accession #KC156671); Cry7Ka1 (Accession #KC156680); Cry7Kb1 (Accession #BAM99306); Cry7La1 (Accession #BAM99307); Cry8Aa1 (Accession #AAA21117); Cry8Ab1 (Accession #EU044830); Cry8Ac1 (Accession #KC156662); Cry8Ad1 (Accession #KC156684); Cry8Ba1 (Accession #AAA21118); Cry8Bb1 (Accession #CAD57542); Cry8Bc1 (Accession #CAD57543); Cry8Ca1 (Accession #AAA21119); Cry8Ca2 (Accession #AAR98783); Cry8Ca3 (Accession #EU625349); Cry8Ca4 (Accession #ADB54826); Cry8Da1 (Accession #BAC07226); Cry8Da2 (Accession #BD133574); Cry8Da3 (Accession #BD133575); Cry8Db1 (Accession #BAF93483); Cry8Ea1 (Accession #AAQ73470); Cry8Ea2 (Accession #EU047597); Cry8Ea3 (Accession #KC855216); Cry8Fa1 (Accession #AAT48690); Cry8Fa2 (Accession #HQ174208); Cry8Fa3 (Accession #AFH78109); Cry8Ga1 (Accession #AAT46073); Cry8Ga2 (Accession #ABC42043); Cry8Ga3 (Accession #FJ198072); Cry8Ha1 (Accession #AAW81032); Cry8Ia1 (Accession #EU381044); Cry8Ia2 (Accession #GU073381); Cry8Ia3 (Accession #HM044664); Cry8Ia4 (Accession #KC156674); Cry8Ib1 (Accession #GU325772); Cry8Ib2 (Accession #KC156677); Cry8Ja1 (Accession #EU625348); Cry8Ka1 (Accession #FJ422558); Cry8Ka2 (Accession #ACN87262); Cry8Kb1 (Accession #HM123758); Cry8Kb2 (Accession #KC156675); Cry8La1 (Accession #GU325771); Cry8Ma1 (Accession #HM044665); Cry8Ma2 (Accession #EEM86551); Cry8Ma3 (Accession #HM210574); Cry8Na1 (Accession #HM640939); Cry8Pa1 (Accession #HQ388415); Cry8Qa1 (Accession #HQ441166); Cry8Qa2 (Accession #KC152468); Cry8Ra1 (Accession #AFP87548); Cry8Sa1 (Accession #JQ740599); Cry8Ta1 (Accession #KC156673); Cry8-like (Accession #FJ770571); Cry8-like (Accession #ABS53003); Cry9Aa1 (Accession #CAA41122); Cry9Aa2 (Accession #CAA41425); Cry9Aa3 (Accession #GQ249293); Cry9Aa4 (Accession #GQ249294); Cry9Aa5 (Accession #JX174110); Cry9Aa like (Accession #AAQ52376); Cry9Ba1 (Accession #CAA52927); Cry9Ba2 (Accession #GU299522); Cry9Bb1 (Accession #AAV28716); Cry9Ca1 (Accession #CAA85764); Cry9Ca2 (Accession #AAQ52375); Cry9Da1 (Accession #BAA19948); Cry9Da2 (Accession #AAB97923); Cry9Da3 (Accession #GQ249293); Cry9Da4 (Accession #GQ249297); Cry9Db1 (Accession #AAX78439); Cry9Dc1 (Accession #KC156683); Cry9Ea1 (Accession #BAA34908); Cry9Ea2 (Accession #AAO12908); Cry9Ea3 (Accession #ABM21765); Cry9Ea4 (Accession #ACE88267); Cry9Ea5 (Accession #ACF04743); Cry9Ea6 (Accession #ACG63872); Cry9Ea7 (Accession #FJ380927); Cry9Ea8

(Accession #GQ249292); Cry9Ea9 (Accession #JN651495); Cry9Eb1 (Accession #CAC50780); Cry9Eb2 (Accession #GQ249298); Cry9Eb3 (Accession #KC156646); Cry9Ec1 (Accession #AAC63366); Cry9Ed1 (Accession #AAX78440); Cry9Ee1 (Accession #GQ249296); Cry9Ee2 (Accession #KC156664); Cry9Fa1 (Accession #KC156692); Cry9Ga1 (Accession #KC156699); Cry9-like (Accession #AAC63366); Cry10Aa1 (Accession #AAA22614); Cry10Aa2 (Accession #E00614); Cry10Aa3 (Accession #CAD30098); Cry10Aa4 (Accession #AFB18318); Cry10A-like (Accession #DQ167578); Cry11Aa1 (Accession #AAA22352); Cry11Aa2 (Accession #AAA22611); Cry11Aa3 (Accession #CAD30081); Cry11Aa4 (Accession #AFB18319); Cry11Aa-like (Accession #DQ166531); Cry11Ba1 (Accession #CAA60504); Cry11Bb1 (Accession #AAC97162); Cry11Bb2 (Accession #HM068615); Cry12Aa1 (Accession #AAA22355); Cry13Aa1 (Accession #AAA22356); Cry14Aa1 (Accession #AAA21516); Cry14Ab1 (Accession #KC156652); Cry15Aa1 (Accession #AAA22333); Cry16Aa1 (Accession #CAA63860); Cry17Aa1 (Accession #CAA67841); Cry18Aa1 (Accession #CAA67506); Cry18Ba1 (Accession #AAF89667); Cry18Ca1 (Accession #AAF89668); Cry19Aa1 (Accession #CAA68875); Cry19Ba1 (Accession #BAA32397); Cry19Ca1 (Accession #AFM37572); Cry20Aa1 (Accession #AAB93476); Cry20Ba1 (Accession #ACS93601); Cry20Ba2 (Accession #KC156694); Cry20-like (Accession #GQ144333); Cry21Aa1 (Accession #I32932); Cry21Aa2 (Accession #I66477); Cry21Ba1 (Accession #BAC06484); Cry21Ca1 (Accession #JF521577); Cry21Ca2 (Accession #KC156687); Cry21Da1 (Accession #JF521578); Cry22Aa1 (Accession #I34547); Cry22Aa2 (Accession #CAD43579); Cry22Aa3 (Accession #ACD93211); Cry22Ab1 (Accession #AAK50456); Cry22Ab2 (Accession #CAD43577); Cry22Ba1 (Accession #CAD43578); Cry22Bb1 (Accession #KC156672); Cry23Aa1 (Accession #AAF76375); Cry24Aa1 (Accession #AAC61891); Cry24Ba1 (Accession #BAD32657); Cry24Ca1 (Accession #CAJ43600); Cry25Aa1 (Accession #AAC61892); Cry26Aa1 (Accession #AAD25075); Cry27Aa1 (Accession #BAA82796); Cry28Aa1 (Accession #AAD24189); Cry28Aa2 (Accession #AAG00235); Cry29Aa1 (Accession #CAC80985); Cry30Aa1 (Accession #CAC80986); Cry30Ba1 (Accession #BAD00052); Cry30Ca1 (Accession #BAD67157); Cry30Ca2 (Accession #ACU24781); Cry30Da1 (Accession #EF095955); Cry30Db1 (Accession #BAE80088); Cry30Ea1 (Accession #ACC95445); Cry30Ea2 (Accession #FJ499389); Cry30Fa1 (Accession #ACI22625); Cry30Ga1 (Accession #ACG60020); Cry30Ga2 (Accession #HQ638217); Cry31Aa1 (Accession #BAB11757); Cry31Aa2 (Accession #AAL87458); Cry31Aa3 (Accession #BAE79808); Cry31Aa4 (Accession #BAF32571); Cry31Aa5 (Accession #BAF32572); Cry31Aa6 (Accession #BAI44026); Cry31Ab1 (Accession #BAE79809); Cry31Ab2 (Accession #BAF32570); Cry31Ac1 (Accession #BAF34368); Cry31Ac2 (Accession #AB731600); Cry31Ad1 (Accession #BAI44022); Cry32Aa1 (Accession #AAG36711); Cry32Aa2 (Accession #GU063849); Cry32Ab1 (Accession #GU063850); Cry32Ba1 (Accession #BAB78601); Cry32Ca1 (Accession #BAB78602); Cry32Cb1 (Accession #KC156708); Cry32Da1 (Accession #BAB78603); Cry32Ea1 (Accession #GU324274); Cry32Ea2 (Accession #KC156686); Cry32Eb1 (Accession #KC156663); Cry32Fa1 (Accession #KC156656); Cry32Ga1 (Accession #KC156657); Cry32Ha1 (Accession #KC156661); Cry32Hb1 (Accession #KC156666); Cry32Ia1 (Accession #KC156667); Cry32Ja1 (Accession #KC156685); Cry32Ka1 (Accession #KC156688); Cry32La1 (Accession #KC156689); Cry32Ma1 (Accession #KC156690); Cry32Mb1 (Accession #KC156704); Cry32Na1 (Accession #KC156691); Cry32Oa1 (Accession #KC156703); Cry32Pa1 (Accession #KC156705); Cry32Qa1 (Accession #KC156706); Cry32Ra1 (Accession #KC156707); Cry32Sa1 (Accession #KC156709); Cry32Ta1 (Accession #KC156710); Cry32Ua1 (Accession #KC156655); Cry33Aa1 (Accession #AAL26871); Cry34Aa1 (Accession #AAG50341); Cry34Aa2 (Accession #AAK64560); Cry34Aa3 (Accession #AAT29032); Cry34Aa4 (Accession #AAT29030); Cry34Ab1 (Accession #AAG41671); Cry34Ac1 (Accession #AAG50118); Cry34Ac2 (Accession #AAK64562); Cry34Ac3 (Accession #AAT29029); Cry34Ba1 (Accession #AAK64565); Cry34Ba2 (Accession #AAT29033); Cry34Ba3 (Accession #AAT29031); Cry35Aa1 (Accession #AAG50342); Cry35Aa2 (Accession #AAK64561); Cry35Aa3 (Accession #AAT29028); Cry35Aa4 (Accession #AAT29025); Cry35Ab1 (Accession #AAG41672); Cry35Ab2 (Accession #AAK64563); Cry35Ab3 (Accession #AY536891); Cry35Ac1 (Accession #AAG50117); Cry35Ba1 (Accession #AAK64566); Cry35Ba2 (Accession #AAT29027); Cry35Ba3 (Accession #AAT29026); Cry36Aa1 (Accession #AAK64558); Cry37Aa1 (Accession #AAF76376); Cry38Aa1 (Accession #AAK64559); Cry39Aa1 (Accession #BAB72016); Cry40Aa1 (Accession #BAB72018); Cry40Ba1 (Accession #BAC77648); Cry40Ca1 (Accession #EU381045); Cry40Da1 (Accession #ACF15199); Cry41Aa1 (Accession #BAD35157); Cry41Ab1 (Accession #BAD35163); Cry41Ba1 (Accession #HM461871); Cry41Ba2 (Accession #ZP_04099652); Cry42Aa1 (Accession #BAD35166); Cry43Aa1 (Accession #BAD15301); Cry43Aa2 (Accession #BAD95474); Cry43Ba1 (Accession #BAD15303); Cry43Ca1 (Accession #KC156676); Cry43Cb1 (Accession #KC156695); Cry43Cc1 (Accession #KC156696); Cry43-like (Accession #BAD15305); Cry44Aa (Accession #BAD08532); Cry45Aa (Accession #BAD22577); Cry46Aa (Accession #BAC79010); Cry46Aa2 (Accession #BAG68906); Cry46Ab (Accession #BAD35170); Cry47Aa (Accession #AAY24695); Cry48Aa (Accession #CAJ18351); Cry48Aa2 (Accession #CAJ86545); Cry48Aa3 (Accession #CAJ86546); Cry48Ab (Accession #CAJ86548); Cry48Ab2 (Accession #CAJ86549); Cry49Aa (Accession #CAH56541); Cry49Aa2 (Accession #CAJ86541); Cry49Aa3 (Accession #CAJ86543); Cry49Aa4 (Accession #CAJ86544); Cry49Ab1 (Accession #CAJ86542); Cry50Aa1 (Accession #BAE86999); Cry50Ba1 (Accession #GU446675); Cry50Ba2 (Accession #GU446676); Cry51Aa1 (Accession #ABI14444); Cry51Aa2 (Accession #GU570697); Cry52Aa1 (Accession #EF613489); Cry52Ba1 (Accession #FJ361760); Cry53Aa1 (Accession #EF633476); Cry53Ab1 (Accession #FJ361759); Cry54Aa1 (Accession #ACA52194); Cry54Aa2 (Accession #GQ140349); Cry54Ba1 (Accession #GU446677); Cry55Aa1 (Accession #ABW88932); Cry54Ab1 (Accession #JQ916908); Cry55Aa2 (Accession #AAE33526); Cry56Aa1 (Accession #ACU57499); Cry56Aa2 (Accession #GQ483512); Cry56Aa3 (Accession #JX025567); Cry57Aa1 (Accession #ANC87261); Cry58Aa1 (Accession #ANC87260); Cry59Ba1 (Accession #JN790647); Cry59Aa1 (Accession #ACR43758); Cry60Aa1 (Accession #ACU24782); Cry60Aa2 (Accession #EAO57254); Cry60Aa3 (Accession #EEM99278); Cry60Ba1 (Accession #GU810818); Cry60Ba2 (Accession #EAO57253);

Cry60Ba3 (Accession #EEM99279); Cry61Aa1 (Accession #HM035087); Cry61Aa2 (Accession #HM132125); Cry61Aa3 (Accession #EEM19308); Cry62Aa1 (Accession #HM054509); Cry63Aa1 (Accession #BAI44028); Cry64Aa1 (Accession #BAJ05397); Cry65Aa1 (Accession #HM461868); Cry65Aa2 (Accession #ZP_04123838); Cry66Aa1 (Accession #HM485581); Cry66Aa2 (Accession #ZP_04099945); Cry67Aa1 (Accession #HM485582); Cry67Aa2 (Accession #ZP_04148882); Cry68Aa1 (Accession #HQ113114); Cry69Aa1 (Accession #HQ401006); Cry69Aa2 (Accession #JQ821388); Cry69Ab1 (Accession #JN209957); Cry70Aa1 (Accession #JN646781); Cry70Ba1 (Accession #ADO51070); Cry70Bb1 (Accession #EEL67276); Cry71Aa1 (Accession #JX025568); Cry72Aa1 (Accession #JX025569).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. No. 8,304,604 and 8.304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; TIC807 of US2040194351, TIC853 toxins of U.S. Pat. No. 8,513,494, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; AXMI221 of US20140196175; AXMI345 of US 20140373195; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/intro.html which can be accessed on the world-wide web using the "www" prefix). The insecticidal activity of Cry proteins is well known to one skilled in the art (for review, see, van Frannkenhuyzen, (2009) *J Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix).

Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus or Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) J Nat Prod 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity, including but not limited to 7-epizingiberene synthase (US Patent Publication 20140157456).

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC® under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene, and U.S. Pat. Nos. 6,563,020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum.*

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712 and Parijs, et al., (1991) *Planta*

183:258-264 and Bushnell, et al., (1998) *Can. J. of Plant Path.* 20(2):137-149. Also see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) *Planta* 204:472-479, Williamson, (1999) *Curr Opin Plant Bio.* 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035.

(W) Genes that confer resistance to *Colletotrichum*, such as described in US Patent Application Publication US 2009/0035765. This includes the Rcg locus that may be utilized as a single locus conversion.

2. Transgenes that Confer Resistance to a Herbicide, for Example:

(A) A polynucleotide encoding resistance to a herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 5,094,945, 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1 and 5,879,903. Exemplary genes conferring resistance to phenoxy proprionic acids and cyclohexones, such as sethoxydim and haloxyfop, are the Acct-S1, Acc1-S2 and Acc1-S3 genes described by Marshall, et al., (1992) *Theor. Appl. Genet.* 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) *Plant Cell* 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) *Biochem J.* 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687) and genes for various phosphotransferases (Datta, et al., (1992) *Plant Mol Biol* 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. No. 6,288,306 B1; 6,282,837 B1 and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop)

herbicides. The aad-1 gene, itself, for herbicide tolerance in plants was first disclosed in WO 2005/107437 (see also, US 2009/0093366). The aad-12 gene, derived from Delftia *acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding a herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtl) described in Misawa, et al., (1993) *Plant J.* 4:833-840 and in Misawa, et al., (1994) *Plant J.* 6:481-489 for norflurazon tolerance.

3. Transgenes that Confer or Contribute to an Altered Grain Characteristic

Such as:

(A) Altered fatty acids, for example, by (1) Down-regulation of stearoyl-ACP to increase stearic acid content of the plant. See, Knultzon, et al., (1992) *Proc. Natl. Acad. Sci. USA* 89:2624 and WO 1999/64579 (Genes to Alter Lipid Profiles in Corn).

(2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).

(3) Altering conjugated linolenic or linoleic acid content, such as in WO 2001/12800.

(4) Altering LEC1, AGP, Dek1, Superal1, mi1 ps, various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), Primula Δ6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794).

(8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).

(9) Nucleic acid molecules encoding wrinkled1-like polypeptides for modulating sugar metabolism (U.S. Pat. No. 8,217,223).

(B) Altered phosphorus content, for example, by the (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197,561, 6,291,224, 6,391,348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) *J. Bacteriol.* 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that confers male fertility to be transcribed.

(A) Introduction of a deacetylase gene under the control of a tapetum-specific promoter and with the application of the chemical N—Ac-PPT (WO 2001/29237).

(B) Introduction of various stamen-specific promoters (WO 1992/13956, WO 1992/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859,341; 6,297,426; 5,478,369; 5,824,524; 5,850,014 and 6,265,640.

5. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) *Plant Cell Rep* 21:925-932 and WO 1999/25821. Other systems that may be used include the Gin recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

6. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance and salt resistance or tolerance and increased yield under stress.

(A) For example, see: WO 2000/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521.

(B) WO 199938977 describing genes, including CBF genes and transcription factors effective in mitigating the negative effects of freezing, high salinity and drought on plants, as well as conferring other positive effects on plant phenotype.

(C) US Patent Application Publication Number 2004/0148654 and WO 2001/36596 where abscisic acid is altered in plants resulting in improved plant phenotype such as increased yield and/or increased tolerance to abiotic stress.

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/64898, U.S. Pat. Nos. 6,177,275 and 6,107,547 (enhancement of nitrogen utilization and altered nitrogen responsiveness).

(E) For ethylene alteration, see, US Patent Application Publication Number 2004/0128719, US Patent Application Publication Number 2003/0166197 and WO 2000/32761.

(F) For plant transcription factors or transcriptional regulators of abiotic stress, see, e.g., US Patent Application Publication Number 2004/0098764 or US Patent Application Publication Number 2004/0078852.

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420).

(H) Down regulation of polynucleotides encoding poly (ADP-ribose) polymerase (PARP) proteins to modulate programmed cell death (U.S. Pat. No. 8,058,510) for increased vigor.

(I) Polynucleotide encoding DTP21 polypeptides for conferring drought resistance (US Patent Application Publication Number US 2011/0277181).

(J) Nucleotide sequences encoding ACC Synthase 3 (ACS3) proteins for modulating development, modulating response to stress, and modulating stress tolerance (US Patent Application Publication Number US 2010/0287669).

(K) Polynucleotides that encode proteins that confer a drought tolerance phenotype (DTP) for conferring drought resistance (WO 2012/058528).

(L) Tocopherol cyclase (TC) genes for conferring drought and salt tolerance (US Patent Application Publication Number 2012/0272352).

(M) CAAX amino terminal family proteins for stress tolerance (U.S. Pat. No. 8,338,661).

(N) Mutations in the SAL1 encoding gene have increased stress tolerance, including increased drought resistant (US Patent Application Publication Number 2010/0257633).

(O) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133).

(P) Modulating expression in a plant of a nucleic acid encoding a Class III Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FR1), WO 1997/29123, U.S. Pat. Nos. 6,794,560, 6,307,126 (GAI), WO 1999/09174 (D8 and Rht) and WO 2004/076638 and WO 2004/031349 (transcription factors).

7. Genes that Confer Increased Yield (A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).

(B) Over-expression of maize zinc finger protein gene (Zm-ZFP1) using a seed preferred promoter has been shown to enhance plant growth, increase kernel number and total kernel weight per plant (US Patent Application Publication Number 2012/0079623).

(C) Constitutive over-expression of maize lateral organ boundaries (LOB) domain protein (Zm-LOBDP1) has been shown to increase kernel number and total kernel weight per plant (US Patent Application Publication Number 2012/0079622).

(D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893).

(E) Modulating expression in a plant of a nucleic acid encoding a Ste20-like polypeptide or a homologue thereof gives plants having increased yield relative to control plants (EP 2431472).

(F) Genes encoding nucleoside diphosphatase kinase (NDK) polypeptides and homologs thereof for modifying the plant's root architecture (US Patent Application Publication Number 2009/0064373).

8. Genes that Confer Plant Digestibility.

(A) Altering the level of xylan present in the cell wall of a plant by modulating expression of xylan synthase (U.S. Pat. No. 8,173,866).

In some embodiments the stacked trait may be a trait or event that has received regulatory approval. Other events with regulatory approval are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications (isaaa.org/gmapprovaldatabase/default.asp, which can be accessed using the www prefix).

Gene Silencing

In some embodiments the stacked trait may be in the form of silencing of one or more polynucleotides of interest resulting in suppression of one or more target pest polypeptides. In some embodiments the silencing is achieved through the use of a suppression DNA construct.

In some embodiments one or more polynucleotides encoding one or more polypeptides of the insecticidal polypeptides of the disclosure or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Suppression DNA construct" is a recombinant DNA construct which when transformed or stably integrated into the genome of the plant expresses a silencing element, and results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 51% and 100% identical) to all or part of the sense strand (or antisense strand) of the gene of interest.

Silencing elements are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

In some embodiments, a silencing element may comprise hairpin structures that incorporate all or part, of an mRNA encoding sequence in a complementary orientation that results in a potential "stem-loop" structure for the expressed RNA (PCT Publication WO 1999/53050). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression, see, Wesley, et al., (2003) Methods in Molecular Biology, Plant Functional Genomics: Methods and Protocols 236:273-286.

Nucleic acid molecules including silencing elements for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describe polynucleotide silencing elements targeting RyanR and PAT3. PCT publications WO 2016/060911, WO 2016/060912, WO 2016/060913, and WO 2016/060914 describe polynucleotide silencing elements targeting COPI coatomer subunit nucleic acid molecules that confer resistance to Coleopteran and Hemipteran pests. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art. See, for example U.S. Pat. No. 5,039,523 and EP 0480762A2.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the insecticidal polypeptide of the disclosure, and desirably, provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Pseudomonas chlororaphis, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium* pollulans. Of particular interest are the pigmented microorganisms. Host organisms of particular interest include yeast, such as *Rhodotorula* spp., *Aureobasidium* spp., *Saccharomyces* spp. (such as *S. cerevisiae*), *Sporobolomyces* spp., phylloplane organisms such as *Pseudomonas* spp. (such as *P. aeruginosa, P. fluorescens, P. chlororaphis*), *Erwinia* spp., and *Flavobacterium* spp., and other such organisms, including *Agrobacterium tumefaciens, E. coli, Bacillus subtilis, Bacillus cereus* and the like.

Genes encoding the insecticidal polypeptides of the embodiments can be introduced into microorganisms that multiply on plants (epiphytes) to deliver insecticidal polypeptides to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the insecticidal polypeptides of the embodiments can be introduced into a root-colonizing *Bacillus cereus* by standard methods known in the art.

Genes encoding insecticdial polypeptides of the disclosure can be introduced, for example, into the root-colonizing *Bacillus* by means of electro transformation. Specifically, genes encoding the insecticidal polypeptides of the disclosure can be cloned into a shuttle vector, for example, pHT3101 (Lerecius, et al., (1989) *FEMS Microbiol. Letts.* 60:211-218. The shuttle vector pHT3101 containing the coding sequence for the particular insecticidal polypeptide gene of the disclosure can, for example, be transformed into the root-colonizing *Bacillus* by means of electroporation (Lerecius, et al., (1989) *FEMS Microbiol. Letts.* 60:211-218).

Expression systems can be designed so that insecticidal polypeptides of the disclosure are secreted outside the cytoplasm of gram-negative bacteria, such as *E. coli*, for example. Advantages of having insecticidal polypeptides of the disclosure secreted are: (1) avoidance of potential cytotoxic effects of the insecticidal polypeptide of the disclosure expressed; and (2) improvement in the efficiency of purification of the insecticidal polypeptide of the disclosure, including, but not limited to, increased efficiency in the recovery and purification of the protein per volume cell broth and decreased time and/or costs of recovery and purification per unit protein.

Insecticidal polypeptides of the disclosure can be made to be secreted in *E. coli*, for example, by fusing an appropriate *E. coli* signal peptide to the amino-terminal end of the insecticidal polypeptide of the disclosure. Signal peptides recognized by *E. coli* can be found in proteins already known to be secreted in *E. coli*, for example the OmpA protein (Ghrayeb, et al., (1984) *EMBO J,* 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud, et al., (1987) *Meth. Enzymol.* 153:492).

Insecticidal polypeptides of the embodiments can be fermented in a bacterial host and the resulting bacteria processed and used as a microbial spray in the same manner that Bt strains have been used as insecticidal sprays. In the case of an insecticidal polypeptide of the disclosure(s) that is secreted from *Bacillus*, the secretion signal is removed or mutated using procedures known in the art. Such mutations and/or deletions prevent secretion of the insecticidal polypeptide(s) into the growth medium during the fermentation process. The insecticidal polypeptides of the disclosure are retained within the cell, and the cells are then processed to yield the encapsulated insecticidal polypeptides. Any suitable microorganism can be used for this purpose. *Pseudomonas* has been used to express Bt toxins as encapsulated proteins and the resulting cells processed and sprayed as an insecticide (Gaertner, et al., (1993), in: *Advanced Engineered Pesticides*, ed. Kim).

Alternatively, the insecticidal polypeptides of the disclosure are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated insecticidal polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient or an agrochemical composition that contains at least one of the insecticidal polypeptides of the disclosure produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-)Dimethenamid, Glufosinate, Glyphosate, Isoxaflutole, (S-Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau- Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Athetis lepigone; Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (*Xylomyges*) *curialis* Grote (citrus cutworm); borers, casebearers, webworms, coneworms; *Sesamia inferens* (Asiatic pink stem borer), and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenee (celery leather); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit tortrix moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Conogethes punctiferalis* (Yellow Peach Moth); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus serous, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are well known in the art. See, for example, Czapla and Lang, (1990) *J Econ. Entomol.* 83:2480-2485; Andrews, et al., (1988) *Biochem J.* 252:199-206; Marrone, et al., (1985) *J. of Economic Entomology* 78:290-293 and U.S. Pat. No. 5,743,477. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest with an insecticidally-effective amount of an insecticidal polypeptide of the disclosure. In some embodiments methods are provided for killing an insect pest, comprising contacting the insect pest with an insecticidally-effective amount of one or more IPD078-1, IPD078-2, IPD084, IPD086-1, IPD086-2, IPD087, and/or IPD089 polypeptides of the embodiments.

In some embodiments methods are provided for controlling an insect pest population, comprising contacting the insect pest population with an insecticidally-effective amount of a recombinant insecticidal polypeptide of the embodiments. In some embodiments methods are provided for controlling an insect pest population, comprising contacting the insect pest population with an insecticidally-effective amount of one or more IPD078-1, IPD078-2, IPD084, IPD086-1, IPD086-2, IPD087, and/or IPD089 polypeptides of the embodiments. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population with an insecticidally-effective amount of a recombinant insecticidal polypeptide of the disclosure. In some embodiments methods are provided for controlling an insect pest population resistant to a pesticidal protein, comprising contacting the insect pest population with an insecticidally-effective amount of one or more IPD078-1, IPD078-2, IPD084, IPD086-1, IPD086-2, IPD087, and/or IPD089 polypeptides of the embodiments.

In some embodiments methods are provided for protecting a plant from an insect pest, comprising expressing in the plant or cell thereof a recombinant polynucleotide encoding an insecticidal polypeptide of the disclosure. In some embodiments methods are provided for protecting a plant from an insect pest, comprising expressing in the plant or cell thereof a recombinant polynucleotide encoding pesticidal protein of one or more IPD078-1, IPD078-2, IPD084, IPD086-1, IPD086-2, IPD087, and/or IPD089 polypeptides of the embodiments.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the insecticidal polypeptides of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management the at least one of the insecticidal proteins comprise an insecticidal polypeptide of the disclosure insecticidal to insects in the order Lepidoptera and/or Coleoptera.

In some embodiments the methods of controlling Lepidoptera and/or Coleoptera insect infestation in a transgenic plant and promoting insect resistance management comprise expressing in the transgenic plant an insecticidal polypeptide of the disclosure and a Cry protein insecticidal to insects in the order Lepidoptera and/or Coleoptera having different modes of action.

In some embodiments the methods of controlling Lepidoptera and/or Coleoptera insect infestation in a transgenic plant and promoting insect resistance management comprise in the transgenic plant one or more IPD078-1, IPD078-2, IPD084, IPD086-1, IPD086-2, IPD087, and/or IPD089 polypeptides of the embodiments and a Cry protein insecticidal to insects in the order Lepidoptera and/or Coleoptera having different modes of action.

Also provided are methods of reducing likelihood of emergence of Lepidoptera and/or Coleoptera insect resistance to transgenic plants expressing in the plants insecticidal proteins to control the insect species, comprising expression of one or more insecticidal polypeptides of the disclosure insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an insecticidal polypeptide of the disclosure and a Cry protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the insecticidal polypeptide of the disclosure does not compete with binding sites for Cry proteins in such insects.

All publications and patent applications are herein incorporated by reference to the same extent as if each individual publication or patent application was specifically and individually indicated to be incorporated by reference.

Although the foregoing embodiments have been described in some detail by way of illustration and example for purposes of clarity of understanding, certain changes and modifications may be practiced within the scope of the appended claims.

The following examples are offered by way of illustration and not by way of limitation.

EXPERIMENTAL

Example 1. Insect Feeding Assays

Insecticidal activity bioassay screens were conducted on the cleared lysate to evaluate the effects of the insecticidal proteins on a variety of Lepidoptera species (European corn borer (*Ostrinia nubilalis*), corn earworm (*Helicoverpa zea*), black cutworm (*Agrotis ipsilon*), fall armyworm (*Spodoptera frupperda*), Soybean looper (*Pseudoplusia includens*) and Velvet bean caterpillar (*Anticarsia gemmatalis*)), a Coleoptera species (Western corn rootworm (*Diabrotica virgifera*)), and two Hemiptera species (*Lygus* (*Lygus hesperus*) and Southern Green Stinkbug (*Nezara viridula*)).

Lepidopteran Assays

Lepidoptera feeding assays were conducted on an artificial diet containing the cleared lysates of bacterial strains in a 96 well plate set up. The cleared lysate was incorporated with the Lepidopteran-specific artificial diet in a ratio of 25 ul cleared lysate and 35 ul of diet mixture. Two to five neonate larvae were placed in each well to feed for 5 days. Results were expressed as positive for larvae reactions such as stunting and/or mortality. Results were expressed as negative if the larvae were similar to the negative control that is fed diet to which the above buffer only has been applied. Each cleared lysate was assayed on European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*). A series of concentrations of the purified protein sample was assayed against those insects and concentrations for 50% mortality (LC50) or inhibition of development of 50% of the individuals (IC50) were calculated.

Coleopteran Assays

Coleoptera feeding assays were conducted on an artificial diet containing the cleared lysates of bacterial strains in a 96 well plate set up. The cleared lysate was incorporated with the coleopteran-specific artificial diet in a ratio of 10 ul cleared lysate and 50 ul of diet mixture. Two to five Western corn rootworm (*Diabrotica virgifera*) neonate larvae were placed in each well to feed for 5 days. Results were expressed as positive for larvae reactions such as stunting and/or mortality. Results were expressed as negative if the larvae were similar to the negative control that is fed diet to which the above buffer only has been applied. A series of concentrations of the purified protein sample was assayed against those insects and concentrations for 50% mortality (LC50) or inhibition of 50% of the individuals (IC50) were calculated.

*Lygus* (*Lygus hesperus*) Bioassay 20 ul of the cleared lysate samples were mixed with 75 ul *Lygus* diet (Bio-Serv F9644B) in each well of a 96 well bioassay plate (BD Falcon 353910) and covered with a sheet of Parafilm. A variable numbers of *Lygus hesperus* second instar nymphs (2 to 7) were placed into each well of a 96 well filter plate. The sample plate was then flipped on to the filter plate and held together with rubber bands. The assay was run four days at 25° C. and then was scored for insect mortality and/or stunting of insect growth. A series of concentrations of the purified protein sample was assayed against those insects and concentrations for 50% mortality (LC50) or inhibition of 50% of the individuals (IC50) were calculated.

Southern Green Stinkbug (*Nezara viridula*) Bioassay 40 ul of the cleared lysate samples were mixed with 360 ul of *Lygus* diet (Bio-Serv F9644B) in Parafilm® packets. 10 to 15 newly molted second instar nymphs were placed in polystyrene Petri dishes (100 mm×20 mm) lined with moist Whatman® filter paper (100 mm diameter). Included in the dish was a water source. The bioassay was incubated at 25° C. in the dark for three days and the then the diet/sample packet was replaced. The bioassay was scored for mortality and stunting. To generate ILC50 or LC50 data, a series of concentrations of purified proteins were assayed against insects and the concentration at which 50% of the nymphs experienced severe stunting was calculated as the ILC50 and the concentration at which 50% of insects were dead was calculated as the LC50.

Example 2. Identification of Insecticidal Active Strains

Insecticidal activities against SBL, CEW, BCW, VBC, ECB, *Lygus*, SGSB, and WCRW were observed from a clear cell lysate of bacterial strains grown in either LB medium (10 g/L tryptone, 5 g/L yeast extract, and 10 g/L NaCl) or TSB (Tryptic Soy Broth) medium (17 g/L tryptone, 3 g/L soytone, 2.5 g/L dextrose, 2.5 g/L $K_2HPO_4$ and 5 g/L NaCl) and cultured overnight at 26° C. with shaking at 250 rpm. This insecticidal activity exhibited heat and proteinase sensitivity indicating proteinaceous nature. Active strains and their insecticidal activities were listed in Table 1.

TABLE 1

Insecticidal Activity for Active Strains.

| Strain | Species | Insect Activity | Gene | Polypeptide Seq. No. |
|---|---|---|---|---|
| SSP344E5 | *Pseudomonas chlororaphis* | SBL, VBC, CEW, ECB | IPD078Aa-1/2 | SEQ ID NO: 43/ SEQ ID NO: 44 |
| JH23996-2 | *Enterobacter cloacae* | WCRW | IPD084Aa | SEQ ID NO: 45 |
| JH23959-1 | *Pseudomonas entomophila* | WCRW, SBL, FAW, CEW, SGSB | IPD085Aa | SEQ ID NO: 51 |
| SSP283F7-1 | *Burkholderia ambifaria* | WCRW | IPD086Aa-1/2 | SEQ ID NO: 56/ SEQ ID NO: 57 |
| JH34636-1 | *Burkholderia* sp. | SBL, VBC | IPD087Aa | SEQ ID NO: 69 |
| JH33490-1 | *Burkholderia ambifaria* | WCRW | IPD089Aa | SEQ ID NO: 70 |

Example 3. Species Identification and Genome Sequencing of Active Strains

Genomic DNA from active strains was extracted with a Sigma® Bacterial Genomic DNA Extraction Kit (Cat #NA2110-KT, Sigma-Aldrich, PO Box 14508, St. Louis, Mo. 63178) according to the manufacturer's instructions. The DNA concentration was determined using a NanoDrop™ Spectrophotometer (Thermo Scientific, 3411 Silverside Road, Bancroft Building, Suite 100, Wilmington, Del. 19810) and the genomic DNA was diluted to 40 ng/ul with sterile water. A 25 ul PCR reaction was set up by combining 80 ng genomic DNA, 2 ul (5 uM) 16S ribosomal DNA primers TACCTTGTTACGACTT (SEQ ID NO: 84) and AGAGTTTGATCMTGGCTCAG (SEQ ID NO: 85), 1 ul 10 cmM dNTP, 1× Phusion® HF buffer, and 1 unit of Phusion® High-Fidelity DNA Polymerase (New England Biolabs, Cat #M0530L, 240 County Road, Ipswich, Mass. 01938-2723). The PCR reaction was run in MJ Research PTC-200 Thermo Cycler (Bio-Rad Laboratories, Inc., 1000 Alfred Nobel Drive, Hercules, Calif., 94547, USA) with the following program: 96° C. 1 min; 30 cycles of 96° C. 15 seconds, 52° C. 2 minutes and 72° C. 2 minutes; 72° C. 10 minutes; and hold on 4° C. The PCR products were purified with Qiaquick® DNA purification Kit (Cat #28104, QIAGEN Inc., 27220 Turnberry Lane, Valencia, Calif. 91355). The purified PCR sample was DNA sequenced and the resulting 16S ribosomal DNA sequence was BLAST searched against the NCBI database. The top hits indicated the species of the strain (see Table 1).

Genomic DNA of active strains was also prepared according to a library construction protocol developed by Illumina (5200 Illumina Way, San Diego, Calif. 92122 USA) and sequenced using the Illumina MiSeg™. The nucleic acid contig sequences were assembled and open reading frames were generated.

Example 4. Identification of Insecticidal Proteins by LC-MS/MS

All insecticidal proteins were fractionated and enriched as described. For identification candidate protein bands were excised, digested with trypsin and analyzed by nano-liquid chromatography/electrospray tandem mass spectrometry (nano-LC/ESI-MS/MS) on a Thermo Q Exactive™ Orbitrap™ mass spectrometer (Thermo Fisher Scientific) interfaced with an Eksigent® NanoLC Ultra 1D Plus™ nanoLC system (AB Sciex). Alternatively, the proteins in the chromatography fractions were directly digested with trypsin and then analyzed by nano-LC/ESI-MS/MS. The MS data was collected in data-dependent acquisition (DDA) mode.

Protein identification was done by database searches using Mascot (Matrix Science). The searches were done against an in-house database which contains annotated protein sequences of bacterial genomes and the public database Swiss-Prot as well as other in-house protein sequence databases simultaneously.

Example 5. Isolation and Identification of Insecticidal Proteins

Isolation and Identification of IPD078Aa-1/2

Insecticidal activity against WCRW (*Diabrotica virgifera*) was observed from a clear cell lysate from *Pseudomonas chlororaphis* strain SSP344E5 grown in Trypticase Soy (Tryptone—11 g/L, Phytone—3 g/L, Sodium chloride—5 g/L, dipotassium phosphate—2.5 g/L, glucose—2.5 g/L) and cultured overnight at 26° C. with shaking at 250 rpm. This insecticidal activity exhibited heat and protease sensitivity indicating proteinaceous nature.

Cell pellets of SSP344E5 were homogenized at 30,000 psi after re-suspension in Tris buffer, pH 9.0. The crude lysate was cleared by centrifugation and loaded onto a column packed with Poros® 50 HQ strong anion exchange media (Life Technologies). Unbound protein containing insecticidal activity was collected and adjusted to pH 6.0 by adding MES to a final concentration of 20 mM. This material was loaded onto a HiTrap® SP Sepharose HP column (GE Healthcare) equilibrated in 20 mM MES pH 6 (Buffer A). Unbound protein was collected and bound protein was eluted with a linear sodium chloride gradient and fractionated. WCRW activity was lost during this step, but restored after fractions containing bound protein were combined with unbound protein at a ratio of 1:1. SDS-PAGE analysis of fractions with restored WCRW activity showed a dominant band after staining with Coomassie® Blue dye. LC-MS/MS was used to identify two novel genes encoded by strain SSP344E5. These genes form an operon and both gene products were required under test conditions for insecticidal activity as confirmed with recombinant protein. These proteins were designated as IPD078Aa-1 (SEQ ID NO: 43) and IPD078Aa-2 (SEQ ID NO: 44).

Isolation and Identification of IPD084Aa

Insecticidal activity against WCRW (*Diabrotica virgifera virgifera*) was observed from crude cell lysates of Strain JH23996-2 (*Enterobacter* sp.). It was grown in 2×YT culture medium at 28° C., 200 rpm, for 1 day in flasks. The growth was pelleted at 25,000×g for 20 min and the supernatant was discarded. The pellet was washed once with ¼ strength PBS before repeating the centrifugation and freezing the pellets at 80 C. The pellets from ≈1 L growth were thawed and resuspended in 20 mM Tris, pH 8 with "Complete, EDTA-free" protease inhibitor cocktail (Roche) at an 5× volume/1× pellet mass before extraction was performed at 25,000 psi. The crude lysate was spun down at 25,000×g for 20 minutes and the resulting supernatant filtered and diluted 1:1 with 20 mM Tris, pH 8 before loading onto two tandemly linked 5 mL HiTrap Q-FF anion exchange columns (GE Healthcare Life Sciences) that had been pre-equilibrated with 20 mM Tris, pH 8. WCRW-active protein was eluted with 20 mM Tris, 0.8 M NaCl, pH 8. The Q-FF eluate was concentrated and loaded onto two S200 10×300 size exclusion columns (GE Healthcare Life Sciences) that were linked in tandem and equilibrated in 100 mM ammonium bicarbonate buffer. Eluted WCRW-active fractions were pooled and desalted into 25 mM MOPS, pH 7 and loaded onto a 4 mL Mono P chromatofocusing column (GE Healthcare Life Sciences) and eluted with Polybuffer 74, pH 5. Two regions of WCRW activity were noted amongst fractions eluted from the Mono P column. The two active fraction pools were desalted into 20 mM MOPS, pH 7.4 buffer and loaded separately onto a 1 mL Mono Q column and eluted with a linear gradient to 20 mM MOPS, 0.5 M NaCl, pH 7.4. Active fractions from the Mono P Region 1 pool eluted at a conductivity range of 4.6-7.7 mS/cm. Active fractions from the Mono P Region 2 pool eluted at conductivity range of 7.7-9.6 mS/cm. SDS-PAGE analysis of fractions with WCRW activity showed a prominent band that was present in both Mono P Region 1 and Region 2 pools that had been purified using Mono Q (GE Healthcare Life Sciences). Protein bands of interest were excised after staining GelCode Blue Stain Reagent (Thermo) and identified through LC-MS/MS. A database search revealed a novel gene candidate encoded by strain JH23996-2 that was associated with WCRW activity of the Mono Q purified Mono P Regions 1 and 2. Cloning and recombinant expression confirmed the insecticidal activity of the candidate against WCRW. The protein was designated IPD084-Aa (SEQ ID NO: 45).

Isolation and Identification of IPD085Aa

Insecticidal activity against WCRW (*Diabrotica virgifera virgifera*) and *lygus* bug (*Lygus hesperus*) was observed from a clear cell lysate of *Pseudomonas entomophila* Strain JH23959-1 grown in Tryptic Soy broth (peptone from casein 15 g/L; peptone from soymeal 5 g/L; NaCl 5.0 g/L) and cultured 1 day at 28° C. with shaking at 200 rpm. This insecticidal activity exhibited heat and protease sensitivity indicating a proteinaceous nature.

Cell pellets of Strain JH23959-1 were lysed at 30,000 psi after re-suspension in 20 mM Tris buffer, pH 8 with "Complete, EDTA-free" protease inhibitor cocktail (Roche). The crude lysate was cleared by centrifugation and brought to 20% saturation using 100% saturated ammonium sulfate. This solution was clarified and the supernatant was brought to 50% saturation with the addition of 100% saturated ammonium sulfate. The 50% saturated ammonium sulfated solution was centrifuged, and the supernatant was discarded. The pellet portion was suspended in 20 mM Tris pH 8.0 and then brought to 1.5M ammonium sulfate with the addition of a 2 M ammonium sulfate in 20 mM Tris pH 8.0 buffer. This solution was clarified and loaded onto a TSKgel Phenyl-5PW column (Tosoh Bioscience) equilibrated in 20 mM Tris pH 8.0, 1.5 M ammonium sulfate and insecticidal activity eluted with a gradient to 20 mM Tris, pH 8. Active fractions were pooled, concentrated on 10 kDa MWCO centrifugal concentrators and desalted into 20 mM Tris. The desalted pool was loaded onto a Toyopearl GigaCap Q-650S column (Tosoh Biosciences) equilibrated in 20 mM Tris pH 8.0 and eluted with a gradient to 0.4 M NaCl in Tris buffer. Active fractions were pooled, buffer exchanged into 20 mM MES, pH 6.0 and then loaded onto a Toyopearl GigaCap S-650S column (Tosoh Biosciences) and active fractions eluted with a gradient to 0.4 m NaCl on MES buffer. SDS-PAGE analysis of fractions with WCRW activity showed a prominent band after staining with GelCode Blue Stain Reagent (Thermo). The protein band was excised and identified through LC-MS/MS. A database search revealed a novel gene candidate encoded by strain JH23959-1. Cloning and recombinant expression confirmed the insecticidal activity of the candidate against WCRW, soybean looper (*Chrysodeixis includes*), *lygus* and Southern green stinkbug (*Nezara viridula*). Cloning and recombinant expression confirmed the insecticidal activity of the candidate against WCRW, *lygus* and SGSB. This protein was designated as IPD085Aa (SEQ ID NO: 51).

Isolation and Identification of IPD086Aa

Insecticidal activity against WCRW (*Diabrotica virgifera*) was observed from a clear cell lysate from *Burkholderia ambifaria* strain SSP283F7 grown in 2×YT (Yeast Extract—10 g/L, Tryptone—16 g/L, Sodium chloride—5 g/L) and cultured for 2 days at 26° C. with shaking at 250 rpm. This insecticidal activity exhibited heat and protease sensitivity indicating proteinaceous nature.

Cell pellets of SSP283F7 were homogenized at 30,000 psi after re-suspension in Tris buffer, pH 9.0. The crude lysate was cleared by centrifugation and loaded onto a column packed with Q Sepharose HP media (GE Healthcare). Bound protein was eluted with a linear sodium chloride gradient and fractionated. Fractions containing protein of interest were pooled and adjusted to 1 M ammonium sulfate concentration in 20 mM Tris (buffer A). This material was loaded onto a column packed with Butyl Sepharose FF media (GE Healthcare) equilibrated in buffer A. Protein was eluted with a linear gradient from 1 M to 0 M ammonium sulfate. Insecticidal activity was detected in a 1:1 mixture of two pools containing protein eluted from 0.7 M to 0.5 M ammonium sulfate and from 0.2 M to 0 M ammonium sulfate. SDS-PAGE analysis of fractions with WCRW activity showed a dominant band after staining with Coomassie® Blue dye. LC-MS/MS was used to identify two novel genes encoded by strain SSP283F7. These genes form an operon and both gene products were required under test conditions for insecticidal activity as confirmed with recombinant protein. These proteins were designated as IPD086Aa-1 (SEQ ID NO: 56) and IPD086Aa-2 (SEQ ID NO: 57).

Isolation and Identification of IPD087Aa

Insecticidal activity against SBL and VBC was observed with crude cell lysates of Strain JH34636-1 (*Burkholderia* sp.). Strain JH34636-1 was grown in 2XYT, 32° C., 1 day, at 200 rpm in flasks. The growth was then pelleted and the pellet washed in 1/4×PBS before repelleting and freezing in the −80° C. The pellets were thawed and lysed in 20 mM Tris, pH 8 with "Complete, EDTA-free" protease inhibitor cocktail (Roche) (≈5× volume-pellet mass) at 25,000 psi. To the crude extract 20 mM Tris, 35% ammonium sulfate, pH 8 added 1:1 to give a final concentration of 17.5% ammonium sulfate. This was rocked for 1 hr before centrifugation and collecting supernatant. 15 mL Phenyl resin (GE Healthcare Life Sciences) was used for a batch separation where the bound was washed and then eluted with 20 mM Tris, pH 8 and collected in a clean bottle. To the eluate solid ammonium sulfate added to a final concentration of ~40%. This was gently stirred overnight before being centrifuged (30,000×g, 20 min) and the supernatant discarded. The pellet was resuspended in 20 mM Tris, pH 8 for 45 min before adding 0.5 M sodium formate, pH 4 to a final concentration of 50 mM and adding 1% formic acid to bring it to ~pH 4. This was rocked for an additional 30 min before centrifugation (30,000×g, 20 min). The supernatant was filtered and desalted into 50 mM sodium formate, pH 4 and loaded on a 1 mL Mono S (GE Healthcare) column equilibrated in the same buffer. Fractions with activity against SBL eluted at three regions at 24.9-30.8 mS/cm, 30.8-40.2 mS/cm and 40.2-51.4 mS/cm with a linear gradient to 50 mM sodium formate, 0.5 M NaCl, pH 4. These were concentrated and loaded separately on two S200 10×300 mm size exclusion columns (GE Healthcare Life Sciences) that were linked in tandem and equilibrated in 100 mM ammonium bicarbonate. All size exclusion runs showed a peak of activity near 28.5 ml (which corresponds to 74 kDa. SDS-PAGE analysis of fractions with SBL and VBC activity showed a prominent band after staining with GelCode Blue Stain Reagent (Thermo). The protein band was excised and identified through LC-MS/MS. A database search revealed a novel gene candidate encoded by Strain JH34636-1. Cloning and recombinant expression confirmed the insecticidal activity of the candidate against SBL and VBC. This protein was designated as IPD087Aa (SEQ ID NO: 69).

Isolation and Identification of IPD089Aa

Activity against western corn rootworm (WCRW, *Diabrotica virgifera virgifera*) was observed from a clear cell lysate of Strain JH33490-1 (*Burkholderia ambifaria*) that was grown in Tryptic Soy Broth at 28° C., 200 rpm for 1 day. The cell pellet was frozen and then thawed before lysis at 30,000 psi after re-suspension in 20 mM MOPS, pH 7.2 with "Complete, EDTA-free" protease inhibitor cocktail (Roche). The lysate was clarified by centrifugation and passed through a 0.45 μm filter.

The filtered extract was diluted 1:1 with 20 mM MOPS, pH 7, and loaded onto a 1 mL Capto Q (GE Healthcare) column and eluted with 20 mM MOPS, 0.5 mM NaCl, pH 7 step gradient. The Capto Q eluate was concentrated with a 10,000 Da MWCO unit and loaded onto two S200 10×300 mm size exclusion columns (GE Healthcare Life Sciences) that were linked in tandem and equilibrated in 100 mM ammonium bicarbonate. Fractions with WCRW activity were pooled and desalted into 25 mM MOPS, pH 6.6 and loaded on a 4 mL Mono P chromatofocusing column (GE Healthcare Life Sciences) and eluted with Polybuffer 74, pH 4). Fractions with WCRW activity were desalted into 20 mM Tris, pH 8 and loaded onto a 1 ml Mono Q column (GE Healthcare Life Sciences). Active fractions eluted with a linear gradient to 20 mM Tris+0.7 M NaCl, pH 8. SDS-PAGE analysis of fractions with WCRW activity showed a prominent band after staining with GelCode Blue Stain Reagent (Thermo). The protein band was excised and identified through LC-MS/MS. A database search revealed a novel gene candidate encoded by strain JH33490-1. Cloning and recombinant expression confirmed the insecticidal activity of the candidate against WCRW. This protein was designated as IPD089Aa (SEQ ID NO: 70).

Example 6 Identification of Homologs

Genomic DNA was extracted from various internal strains, the species was identified and the genome was sequenced as described in Example 3. Gene identities may be determined by conducting BLAST (Basic Local Alignment 20 Search Tool; Altschul, et al., (1993) *J. Mol. Biol.* 215:403-410; see also ncbi.nlm.nih.gov/BLAST/, which can be accessed using the www prefix) searches under default parameters for similarity to sequences contained in the internal genomes and in the publically available BLAST "nr" database (comprising all non-redundant GenBank CDS translations, sequences derived from the 3-dimensional structure Brookhaven Protein Data Bank, the last major release of the 25 SWISS-PROT protein sequence database, EMBL, and DDBJ databases). The polynucleotide sequences of SEQ ID NO: 43-45, 51, 56, 57, and 69-70 were analyzed. Table 2 shows the IPD polypeptides and homologs identified, sequence identification numbers for each polynucleotide and the corresponding polypeptide encoded by the polynucleotide, the bacterial species and/or strains they were identified from, and results from insecticidal activity testing.

TABLE 2

List of orthologs identified by homologous sequence search

| Gene | Source Strain | Poly-nucleo-tide SEQ ID NO: | Polyeptide SEQ ID NO: | Activity |
|---|---|---|---|---|
| IPD078Aa-1 | *Pseudomonas chlororaphis* | 1 | 43 | Yes |
| IPD078Aa-2 | *Pseudomonas chlororaphis* | 2 | 44 | Yes |
| IPD084Aa | *Enterobacter cloacae* | 5 | 45 | Yes |
| IPD084Ea | *Desulfovibrio zosterae* | 6 | 46 | n.d.* |
| IPD084Eb | *Ralstonia* sp. A12 | 7 | 47 | n.d. |
| IPD084Ec | *Pectobacterium carotovorum* | 8 | 48 | n.d. |
| IPD084Ed | *Salinivibrio* sp. | 9 | 49 | n.d. |
| IPD084Ga | *Klebsiella quasipneumoniae* | 10 | 50 | n.d. |
| IPD085Aa | *Pseudomonas entomophila* | 11 | 51 | Yes |
| IPD085Ba | *Pseudomonas aeruginosa* | 12 | 52 | n.d. |
| IPD085Ca | *Pseudomonas phage* | 13 | 53 | n.d. |
| IPD085Cb | *Pseudomonas* aeruginosa_cytotoxin | 14 | 54 | n.d. |
| IPD085Da | *Pectobacterium wasabiae* | 15 | 55 | n.d. |
| IPD086Aa-1 | *Burkholderia ambifaria* | 16 | 56 | Yes |
| IPD086Aa-2 | | 17 | 57 | |
| IPD086Ab-1 | *Burkholderia cenocepacia* | 18 | 58 | Yes |
| IPD086Ab-2 | | 19 | 59 | |
| IPD086Ac-2 | *Burkholderia cepacia* | 20 | 60 | n.d. |
| IPD086Ad-1 | *Burkholderia cepacia* | 21 | 61 | n.d. |
| IPD086Ad-2 | *Burkholderia cepacia* | 22 | 62 | n.d. |
| IPD086Ae-2 | *Burkholderia cepacia* | 23 | 63 | n.d. |
| IPD086Af-1 | *Burkholderia cepacia* | 24 | 64 | n.d. |
| IPD086Af-2 | *Burkholderia cepacia* | 25 | 65 | n.d. |
| IPD086Ag-1 | *Burkholderia cepacia* | 26 | 66 | n.d. |
| IPD086Ag-2 | *Burkholderia cepacia* | 27 | 67 | n.d. |
| IPD086Ah-2 | *Burkholderia cepacia* | 28 | 68 | n.d. |
| IPD087Aa | *Burkholderia* sp. | 29 | 69 | Yes |
| IPD089Aa | *Burkholderia ambifaria* | 30 | 70 | Yes |
| IPD089Ab | *Burkholderia pyrrocinia* | 31 | 71 | n.d. |
| IPD089Ba | *Burkholderia glumae* | 32 | 72 | n.d. |
| IPD089Ca | *Burkholderia anthina* | 33 | 73 | n.d. |
| IPD089Cb | *Burkholderia anthina* | 34 | 74 | n.d. |
| IPD089Ea | *Burkholderia multivorans* | 35 | 75 | n.d. |

TABLE 2-continued

| List of orthologs identified by homologous sequence search | | | | |
|---|---|---|---|---|
| Gene | Source Strain | Poly-nucleo-tide SEQ ID NO: | Polyeptide SEQ ID NO: | Activity |
| IPD089Eb | *Sinorhizobium medicae* | 36 | 76 | n.d. |
| IPD089Fa | *Burkholderia ambifaria* | 37 | 77 | n.d. |
| IPD089Fb | *Burkholderia cenocepacia* | 38 | 78 | n.d. |
| IPD089Fc | *Pseudomonas syringae* | 39 | 79 | n.d. |
| IPD089Ga | *Pseudomonas lini* | 40 | 80 | n.d. |
| IPD089Gb | *Aquimarina muelleri* | 41 | 81 | n.d. |
| IPD089Gc | *Nocardia gamkensis* | 42 | 82 | n.d. |

n.d. signifies activity not determined

Example 7. Gene Subcloning and *E. coli* Expression

The target genes encoding the insecticidal proteins were first amplified by PCR using their genomic DNA as templates. The PCR primers were designed based on the 5' end and 3' end sequences of the gene either with appropriate restriction sites incorporated or with added sequences overlapping with the 5' and 3' ends of the linearized *E. coli* expression vector. With restriction enzyme digestion and ligation or homolog recombination based cloning, the PCR products were cloned into selected *E. coli* expression vectors, i.e. pCOLD™ 1, 3, pET16, 24, 28 for N-, C-His tag and no tag expression. In some cases pMAL™ vector was used for MBP fusion expression. In case of co-expression of two proteins for a binary toxins (IPD078 and IPD086), their native operon sequences were also cloned into one of the above *E. coli* vectors. The proteins were expressed in BL21(DE3), C41 or SHuffle® *E. coli* hosts cells with 1 mM IPTG overnight induction at 16° C.

The recombinant protein was extracted from *E. coli* culture after induction. Cell clear lysates or purified proteins were assayed on insect targets as described in Example 1.

The purified recombinant proteins were tested on each insect target with series dilutions and the minimal inhibitory concentrations were calculated under these test conditions (Table 3).

TABLE 3

| IPD proteins and their minimal inhibitory concentrations on insect targets | | | | | | | |
|---|---|---|---|---|---|---|---|
| | SEQ ID | minimal inhibitory concentration (ppm) | | | | | |
| Protein | NO: | WCRW | *Lygus* | SGSB | CEW | SBL | VBC |
| IPD078Aa-1/ IPD078Aa-2 | 43/44 | n.t. * | n.t. | n.t. | ~20 | ~5 | ~10 |
| IPD084Aa | 45 | 35 | >400 | n.t. | n.t. | n.t. | n.t. |
| IPD085Aa | 51 | 17 | 31 | 12.5 | n.t. | 68 | n.t. |
| IPD086Aa-1/ IPD086Aa-2 | 56/57 | ~100 | n.t. | n.t. | n.t. | n.t. | n.t. |
| IPD087Aa | 69 | n.t. | n.t. | n.t. | n.t. | ~2 | ~10 |
| IPD089Aa | 70 | ~10 | n.t. | n.t. | n.t. | n.t. | n.t. |

* not tested

Example 8. Transient Expression and Insect Bioassay on Transient Leaf Tissues To confirm activity of IPD078Aa-1 (SEQ ID NO: 43) and IPD078Aa-2 (SEQ ID NO: 44) in planta, both were cloned into an *Agrobacterium* transient expression system. Variant IPD078Aa-1 MOD B (SEQ ID NO: 3) was expressed under the control of the At-UBQ10 promotor (Norris S R et al (1993) *Plant Mol Biol.* 21(5):895-906) and targeted for secretion using the Barley alpha amylase signal (Rahmatullah R J, et al., (1989) *Plant Mol. Biol.* 12:119). Variant IPD078Aa-2 MOD A (SEQ ID NO: 4) was placed under control of the At-UBQ10 or the GMUBQ promoter, respectively (Norris S R et al. (1993) *Plant Mol Biol.* 21(5):895-906, Xia et al., *Plant Physiol.* (1994) 104: 805-806). IPD078 Aa-1 MOD B (SEQ ID NO: 3) and IPD078Aa-2 MOD A (SEQ ID NO: 4) were co-infiltrated at a 1:1 ratio.

The infiltration method of introducing an *Agrobacterium* cell suspension to plant cells of intact tissues so that reproducible infection and subsequent plant derived transgene expression may be measured or studied is well known in the art (Kapila J, et al., (1997) *Plant Science* 122:101-108). Briefly, the unifoliate stage of bush bean (California Small White, *Phaseolus vulgaris*) was agro-infiltrated with normalized bacterial cell cultures. Leaf disks were excised from each plantlet and infested with 2 neonates of Soy Bean Looper (SBL) (*Pseudoplusia includens*), Corn Earworm, (CEW) (*Helicoverpa zea*) or 2 neonates of Velvetbean Caterpillar (VBC) (*Anticarsia Gemmatalis*). Leaf disks from non-infiltrated plants were run as a control. The consumption of green leaf tissue was evaluated two (CEW) or three (VBC, SBL) days after infestation and given scores of 0 to 9, The highest leaf injury score of 9 is used for untouched leaves, a score of 8 is used for disks with small but notable pinholes, a score of 7 is used when less than 10% of tissue is consumed, a score of 6 is used when less than 30% of tissue is consumed, a score of 5 indicates 40-50% consumption, a score of 4 indicates 50-60% consumption, a score of 3 indicates 60-70% consumption, a score of 2 indicates 70-80% consumption and a score of 1 indicates that more than 90% of leaf tissue is consumed.

Figure 2:
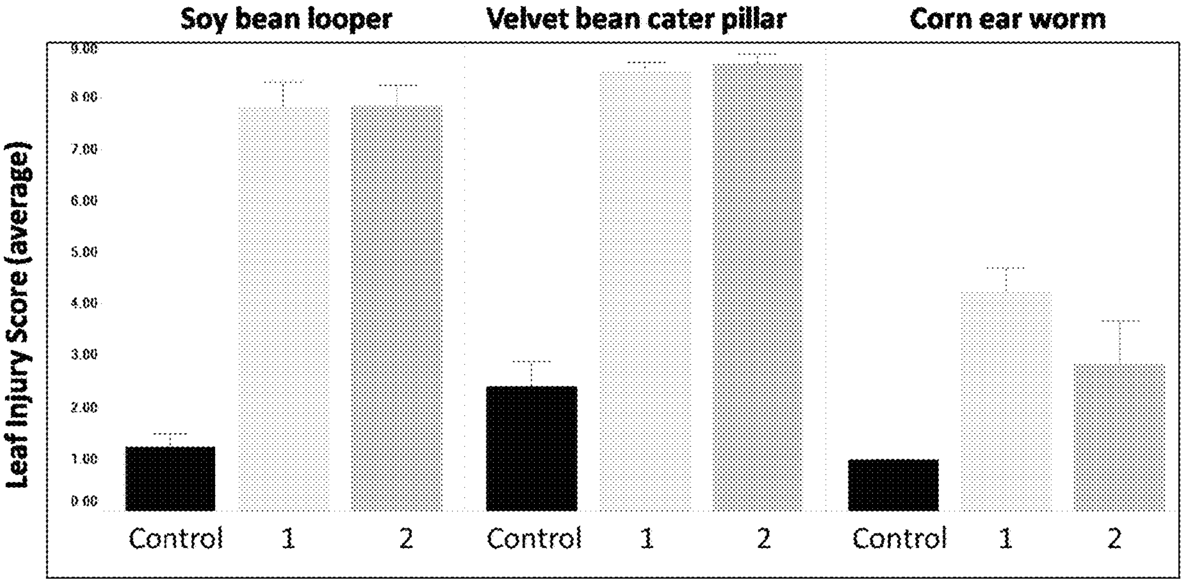
FIG. 2. Feeding inhibition in California small white leaf discs transiently co-transformed with two construct combinations of polynucleotides encoding IPD078-1 (SEQ ID NO: 43) and IPD078-2 (SEQ ID NO: 44). 1-At-UBQ10: BAA:IPD078-1(ModB) (SEQ ID NO: 3)+At-UBQ10: IPD078-2 (SEQ ID NO: 4); 2-At-UBQ10:BAA:IPD078-1 (ModB) (SEQ ID NO: 3)+GMUBQ:IPD078-2 (SEQ ID NO: 4); Control—non-infiltrated leaf discs.

Results are summarized in FIG. 2. Co-expression of IPD078Aa-1 and IPD078Aa-protected leaf disks from consumption by the infested insects tested, independent of vector combinations. In contrast, high level green tissue consumption was observed for the negative control leaf disks.

Example 9—*Agrobacterium*-Mediated Stable Transformation of Maize

For *Agrobacterium*-mediated maize transformation of insecticidal polypeptides, the method of Zhao is employed (US Patent Number 5,981). Briefly, immature embryos are isolated from maize and the embryos contacted with an *Agrobacterium* Suspension, where the bacteria were capable of transferring a polynucleotide encoding an insecticidal polypeptide of the disclosure to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium with antibiotic, but without a selecting agent, for *Agrobacterium* elimination and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

For detection of the insecticidal polypeptide in leaf tissue 4 lyophilized leaf punches/sample are pulverized and resuspended in 100 μL PBS containing 0.1% TWEEN™ 20 (PBST), 1% beta-mercaoptoethanol containing 1 tablet/7 mL complete Mini proteinase inhibitor (Roche 1183615301). The suspension is sonicated for 2 min and then centrifuged at 4° C., 20,000 g for 15 min. To a supernatant aliquot ⅓ volume of 3× NuPAGE® LDS Sample Buffer (Invitrogen™ (CA, USA), 1% B-ME containing 1 tablet/7 mL complete Mini proteinase inhibitor was added. The reaction is heated at 80° C. for 10 min and then centrifuged. A supernatant sample is loaded on 4-12% Bis-Tris Midi gels with MES running buffer as per manufacturer's (Invitrogen™) instructions and transferred onto a nitrocellulose membrane using an iBlot® apparatus (Invitrogen™). The nitrocellulose membrane is incubated in PBST containing 5% skim milk powder for 2 hours before overnight incubation in affinity-purified rabbit anti-insecticidal polypeptide in PBST overnight. The membrane is rinsed three times with PBST and then incubated in PBST for 15 min and then two times 5 min before incubating for 2 hours in PBST with goat anti-rabbit-HRP for 3 hours. The detected proteins are visualized using ECL Western Blotting Reagents (GE Healthcare cat #RPN2106) and Kodak® Biomax® MR film. For detection of the insecticidal protein in roots the roots are lyophilized and 2 mg powder per sample is suspended in LDS, 1% beta-mercaptoethanol containing 1 tablet/7 mL Complete Mini proteinase inhibitor is added. The reaction is heated at 80° C. for 10 min and then centrifuged at 4° C., 20,000 g for 15 min. A supernatant sample is loaded on 4-12% Bis-Tris Midi gels with MES running buffer as per manufacturer's (Invitrogen™) instructions and transferred onto a nitrocellulose membrane using an iBlot® apparatus (Invitrogen™). The nitrocellulose membrane is incubated in PBST containing 5% skim milk powder for 2 hours before overnight incubation in affinity-purified polyclonal rabbit anti-insecticidal antibody in PBST overnight. The membrane is rinsed three times with PBST and then incubated in PBST for 15 min and then two times 5 min before incubating for 2 hours in PBST with goat anti-rabbit-HRP for 3 hrs. The antibody bound insecticidal proteins are detected using ECL™ Western Blotting Reagents (GE Healthcare cat #RPN2106) and Kodak® Biomax® MR film.

Transgenic maize plants positive for expression of the insecticidal proteins are tested for pesticidal activity using standard bioassays known in the art. Such methods include, for example, root excision bioassays and whole plant bioassays. See, e.g., US Patent Application Publication Number US 2003/0120054.

Example 10—Expression Vector Constructs for Expression of Insecticidal Polypeptides in Plants The plant expression vectors, can be constructed to include a transgene cassette containing the coding sequence pf the insecticidal polypeptide, under control of the Mirabilis Mosaic Virus (MMV) promoter [Dey N and Maiti I B, 1999, *Plant Mol. Biol.* 40(5):771-82] in combination with an enhancer element. These constructs can be used to generate transgenic maize events to test for efficacy against corn rootworm provided by expression of the insecticidal polypeptide of the disclosure.

T0 greenhouse efficacy of the events can be measured by root protection from Western corn rootworm. Root protection is measured according to the number of nodes of roots injured (CRWNIS=corn rootworm node injury score) using the method developed by Oleson, et al. (2005) [J. Econ Entomol. 98(1):1-8]. The root injury score is measured from "0" to "3" with "0" indicating no visible root injury, "1" indicating 1 node of root damage, "2" indicating 2 nodes or root damage, and "3" indicating a maximum score of 3 nodes of root damage. Intermediate scores (e.g. 1.5) indicate additional fractions of nodes of damage (e.g. one and a half nodes injured).

That which is claimed:

1. A DNA construct comprising a polynucleotide encoding an insecticidal polypeptide, wherein the insecticidal polypeptide comprises an amino acid sequence having greater than 95% sequence identity compared to the amino acid sequence of SEQ ID NO: 43, and wherein the polynucleotide is operably linked to a heterologous regulatory element.

2. The DNA construct of claim 1, wherein the recombinant polynucleotide comprises the polynucleotide of SEQ ID NO: 1.

3. A transgenic plant or plant cell comprising the DNA construct of claim 1.

4. A method of controlling a Lepidoptera and/or Coleoptera insect infestation in a transgenic plant and providing insect resistance management, said method comprising transforming the DNA construct of claim 1 into a plant.

* * * * *

SEQUENCE LISTING

```
<160> NUMBER OF SEQ ID NOS: 85

<210> SEQ ID NO 1
<211> LENGTH: 759
<212> TYPE: DNA
<213> ORGANISM: Pseudomonas chlororaphis

<400> SEQUENCE: 1

atggctgtga taaagggatt tgttggagtt tgcgttgggg cgctcttcat atttgctggg     60

tctgcatatg ctggcgtaac ggtacagcag gctattcgag aggggtgtta cacttccgct    120

caggctaagg aaataatcgc tcaaggggag aggagtactc ctatggggac tgtaacccta    180

gaaaaggcca agctgtattt agagagggtg aatgacagaa gtgtcacgcg gacaaaggta    240

acagcccctg agacttgggt ataccgtggc tatgacgatg caagcaactg gcataccgaa    300

gagttgttgg atggggttat atattctaaa ggtcaaaatg ctcgagataa ggccatacgg    360

agaggtatct cagaaaagtc tttttggggg aaaaatggtc ctcagcttag gcatgaagct    420

tcgtctgtcg gtagttttcc gggtgagccg acttatttta tgatgcgcct cctagccata    480

cagacgagcg atactcctcc gagtcagttt gtgtcttttg cattgaatta taaacttgcg    540

tccgagtttg gagaggtcgt ctacgcactt caagtaaacc ccgattcgcc tgtgttaggg    600
```

```
cttcagaact gcaatctgaa aggagagtat caggttcaaa ttctcggcgg aacaactttt    660

ggtgtgctgt ataagaaaaa acgaggccag aactgggaac gctacgatcg gagtaaccga    720

gtttgggggc ctgtggctag tggaaccgtg ccggagtga                           759


<210> SEQ ID NO 2
<211> LENGTH: 810
<212> TYPE: DNA
<213> ORGANISM: Pseudomonas chlororaphis

<400> SEQUENCE: 2

atgaaagcaa tacttctaag tagaaagcca gtcggtgtca atgaagatgt atcttatttt     60

tccgaaaagc atgtgatgtt ttatggtgct caaaacaaaa cttctggttt gcctgttcgt    120

ctagttgatg atacgccacc tgttgtcagc gaaagagatc atccttcgct tccaggtatt    180

attcagtcga aaataaaacg tggcacagat tgtgttgttc gtcaaataaa tccagttttt    240

tatctgcggg aaggtgagct tttagtaagc gactcattta gctatctttc taaagcctat    300

ctggagtatg ccgaagatac agtggttctt acccgtaaga caaatatggg cgagttttat    360

tttgtttttc cagatataaa agctaagcgc ttgtatgatg acgcaacggg tgtgactcta    420

gttgatattg ttgatggggg tcgttcattg tatccaatac caccgaaggc gtctttatct    480

acgtctgaga gtgtggtttt agattcttcg ttatatatgt tgacagaggt taagcctaca    540

tcaggtacaa ccatctatct tggctggtct gttccagatg ctaccaaaag tgatgtgtgg    600

tgggggcttt atcgaggggt tatgccagac tggagcggtc tcgatagtta tactaattgg    660

gactggttgt ttcccaaagg tacaacaaat acagcgatag gaagtgagac tataacagtt    720

tcaagaatgt ccagtggggc aatctacacg ttggcactgt tttcgagtgg atggaacctt    780

actgactacc agacctttaa tgcaccgtga                                     810


<210> SEQ ID NO 3
<211> LENGTH: 690
<212> TYPE: DNA
<213> ORGANISM: Unknown
<220> FEATURE:
<223> OTHER INFORMATION: Synthetic

<400> SEQUENCE: 3

atgggcgtca cagtccagca ggccatcagg gagggctgtt acacctccgc gcaggcgaag     60

gagatcatcg cgcaaggcga gcgctccaca ccgatgggca ccgtcaccct ggagaaggcg    120

aagctgtacc tcgagcgggt gaacgaccgg tccgtcacgc ggacgaaggt cactgcgccc    180

gaaacctggg tctatcgcgg gtacgacgac gcctcgaatt ggcacacgga ggagctcctg    240

gacggtgtca tctactcgaa gggccagaac gcgcgggaca aggccatcag gcgcggcatc    300

tcggagaagt cgttctgggg caagaacggt ccccagcttc ggcacgaagc gagctctgtc    360

ggcagcttcc cgggagagcc cacgtacttc atgatgcggc tgctggccat ccagaccagc    420

gacacgccgc ccagccagtt cgtcagcttc gccctgaact acaagctcgc gtccgagttc    480

ggtgaggtcg tctacgcact ccaggtcaac cccgacagcc cggtccttgg cctccagaac    540

tgcaacctga agggcgagta ccaggtccag atcctcggtg gcacgacctt cggcgtcctg    600

tacaagaaga agcgcgggca gaactgggag cggtacgacc ggtcgaaccg cgtttggggt    660

ccagtggcat ccggtacagt cccagagtga                                     690


<210> SEQ ID NO 4
```

<211> LENGTH: 813
<212> TYPE: DNA
<213> ORGANISM: Unknown
<220> FEATURE:
<223> OTHER INFORMATION: Synthetic

<400> SEQUENCE: 4

```
atggcgaagg cgatcctgct ctcgaggaag ccggtcggcg tcaacgagga tgtctcctat     60

ttctccgaga agcacgtcat gttctacggc gcgcagaaca agacctccgg gctgccagtg    120

aggctggtcg acgacacgcc acctgtggtc tctgagaggg accacccatc tctccccggc    180

atcatccagt cgaagatcaa gcgcggcacg gactgcgtgg tgcgccagat caacccggtg    240

ttctacctcc gcgagggcga gctcctcgtc tccgacagct tctcgtacct gtcgaaggcc    300

tacctcgagt acgcggagga caccgtggtg ctgacgcgca agacgaacat gggcgagttc    360

tacttcgtgt tcccggacat caaggcgaag cggctgtacg acgacgccac aggcgtgacc    420

ctcgtggaca tcgtggatgg cggacgcagc ctttacccga tcccaccgaa agcgtcactg    480

tctacgtcgg agagcgtcgt cctcgacagc agcctgtaca tgctcaccga ggtcaagccg    540

acctcaggca ccaccatcta cctgggctgg tcggttcccg acgcgacgaa gtcggacgtc    600

tggtggggcc tctatcgcgg cgtgatgcct gactggtcgg gcctggacag ctacaccaac    660

tgggactggc tcttcccgaa gggcacgacg aacaccgcga tcgggtccga gacgatcacg    720

gtgtcgcgga tgtcctccgg cgccatctac acgctggcgc tgttctcctc agggtggaac    780

ctgaccgact accagacctt caacgcaccc tga                                 813
```

<210> SEQ ID NO 5
<211> LENGTH: 888
<212> TYPE: DNA
<213> ORGANISM: Enterobacter cloacae

<400> SEQUENCE: 5

```
atggctacta ctcagaatca agacctgctt tcaaaattcc atgattgggt tgataacaaa     60

agtgccgcac ctcttcatgg tcctctgtta aaggcccacg cactgttcaa agtggaaaaa    120

tctggagaca gcagtgtttc cggtcagaac acaatcgcaa ctggggatca ggctccccat    180

cagtcagacg ttggtaagat cctggatctg gcgattaaaa accaggaaaa ggataaaatt    240

atcgacattc ttgcaagcaa tccgggcaat gcggtgacca gcattcttgg gctggcaaag    300

acgcgtacaa catggaatcc gctggatccg gataacaata aaaacgcaca agggtttatg    360

gattttgttg agcaaatctt gcgcgttcca tattttcgca ttacgcagtc tgaacatcca    420

accgttaatt acgaagagga gaattatgat tctcttatca acaaggtggc agatctttac    480

gccggtataa ccgaagcaag caaagaaaaa gtgaaaaata gtattgtcaa tctggcgatg    540

gcatgtacca gccgagtcaa cactaaaaat actgatactc tatttgtaca gaactccatt    600

cagtcagcaa atgatgatat tgtcgttcag cttgagcaaa cctatatgct gatggagcgc    660

agccacagta gcggtaaagg tgcacctaaa gataaataca aaacccaggt cgatgttaaa    720

gtcctggaat tgactttttc gtcatcttta tggactcgtg atgcggcagt taaattagcc    780

gcaaaatttg tcaaaagctg ggatgactgg ctggatgaaa atactacgcc agatacatct    840

aaacatgtga aattctgctt tggtaaagaa ggtgctgcgg tcgagtaa                 888
```

<210> SEQ ID NO 6
<211> LENGTH: 852
<212> TYPE: DNA
<213> ORGANISM: Desulfovibrio zosterae

<400> SEQUENCE: 6
atgactgtgc aagctaagtt cgaccaatgg ctggaaaacc ctcaacttat aacaatggaa 60
aagggactga ctgacgctgc tttcatgttt tatattccgg agtcagggga cagcaacgtt 120
tcaggacaaa actcaacagc aacagggtca aatgctcaaa aagagtcagc tcaaggaaaa 180
gagctagatg aggctatagg taaaggcgat gaggaagcaa tagtaagatt gcttactaat 240
tcaactggta atgcagtctc cagcatattg ggtctggccc aaagcaggac agactggaat 300
cctctagacc cgaataatga taaaaatgct gaaggatttc aaaattttat caaaagcatc 360
ttaaaggttc cttttttaa tgtgactcag tcagaaagaa ccactgttca ctatgaagag 420
actaactata acgacctcat tgataaagtg gtagatcttt atgacggtat tactaaatcc 480
gacataccgc tcatcaaaaa tagtattgtg aatctggcta aagcctgcac cagccgtgta 540
aataccaaaa ataccaaaac tctattcgtc caaaatacga tgaatgcaac cggtactgat 600
attgtagttg gaatacagca gacattcatg atgatggaac gcagccatga gagccacaaa 660
ggagcaccta aggatcaata caaaactgag ataactgtta atgttatgga gttgaccttt 720
aagggctcaa tctggaacaa agatgcagca aagaaactcg ctgcaaaatt tgttaagagc 780
tgggatgact ggttagatgg aacaacaaca cctccagaaa aaaaggctgc tgcaatcaaa 840
tattgtttat aa 852

<210> SEQ ID NO 7
<211> LENGTH: 660
<212> TYPE: DNA
<213> ORGANISM: Ralstonia sp. A12

<400> SEQUENCE: 7
gtggacctgc tcacccaatc gaccgccaat gcggtatcga gcatcttggg cttgtcacaa 60
acgcgttcgg ggtggaaccc tcttgacccg accgaaaaag agaatgccca aggcttccag 120
cggttcgtcg agcaaatctt gaaagtgccg tatttcaaca cgacccaggc ggagacgaag 180
accgtccatt accaagagtc gaactacaat tcgctcattg ataaggtggt cgatctgtac 240
gatggcgtga cccagcaaga taaggaaaaa atcaagcgga gcattgtcaa cctggccaag 300
gcatgcacca gccgcgtgaa ccaaaagaat acgcagacgc tgtttgtgca gaacacgatg 360
cacgcgccgg gcaacagtcg caacattgtt gttcaactcg cccagacctt catgatgatg 420
gagcttgatc accgaaccgg caagggcgcg ccgcaggatc agttcaagac cgaaatctcg 480
gttcgggttc tggaactgac attccaaggc gacatctggg accgtagcgc tgcggaaaag 540
cttgccgcca aattcgtaca gagctgggat gactggctga atgactcgac gaccccgccg 600
tcgcctcaac agcggaagat cgcattctgc ttcagcccgc gagagatcgc ctcagtctga 660

<210> SEQ ID NO 8
<211> LENGTH: 873
<212> TYPE: DNA
<213> ORGANISM: Pectobacterium carotovorum

<400> SEQUENCE: 8
atgtctgata ttaaacatga taacgcatta gctacattta gctcatggct tgatgatgat 60
aaaaatatta aattaagtga atcatcaata aacacacacc aactcttcgc attatcagcc 120
gaaggggata gcagtgtatc aggtcaaaat tccatatcaa cgggtacact ggcatctcaa 180
gaatctgcac aaggaaagat tcttgataat gcgatagctc gcggagataa agatgagatt 240

-continued

```
acaaaagttt tgacaagctc gacgggtaat gccgtatcca gtattttggg cttgtcacag    300
agtcgttccg gctggaaccc cttagaccca gataatgata gcaatagtaa aggttttact    360
cgatttgtcg aaagtttatt aaaagtgcct tattttaata caactcaatc agaaagaaca    420
accgttaact atgaagaaga aaactatgat tctctaatta gtaaagttgt tgatttatac    480
agcggtatag aagaaaaaga taaatctaaa ataaaaacaa gcattgtaaa tttagcaaaa    540
gcatgtacga gtcgagtcaa cactaaaaat acaaaaacac ttttcgttca aaatacattg    600
aacgcctcta acaaaaatat cgttgttcaa ttacagcaaa catttatgat gatggagcgt    660
agccatactt caggaaaagg ggcacctaaa gataaatata agacagaaat cattgttcag    720
gtattagaat taacatttca aggagatatt tggacaaaaa gcgctgctga gaaattggct    780
gagaaatttg caaaaagttg ggatgactgg ttaaacgaca cgactacgcc agaatcagat    840
gatgcaaaaa atatcaaatt ctgctttaag taa                                 873
```

<210> SEQ ID NO 9
<211> LENGTH: 918
<212> TYPE: DNA
<213> ORGANISM: Salinivibrio sp.

<400> SEQUENCE: 9

```
atgaacgctt cagatgcaca aaacctgaca tctcaatttg atacttggtt gaatagccac     60
caaagtttgg tctctaacca acagcaactg cagcacagcg cgctctttgc ggtaccacgc    120
gatggcgaca gctcagtatc tggtcagaat accatcggtg ccggtaaaaa tgcgcaaacg    180
gaatcagcgc aaggtaagaa attggatgat gccattagcg ctggcaatca cagtgaaatt    240
gttcgcttgc tcaccgagtc taccggtaat gcggtatcga gcattttagg cttagctcaa    300
agccgcaccg gctggaatcc gctggaccca gataatgaca agaatgccga agggtttcag    360
gagtttgtga gctccattct taaagtgcct ttttttaatg tcacccaatc agagcgcacc    420
acggtgcatt acgaagaaga gaactacaac tctctgattg ataaagtcgt tggcctctat    480
gacgggatca ctgagcaaga tgttccgctg attaaaaaca gtattgtgaa ccttgccaag    540
gcgtgtacta gccgagtgaa tacccaaaac accaaaacct tgtttgtcca aaacaccatg    600
aacgcgactg ggacggacat tgtcgtcggt attcagcaaa cctttatgat gatggagcgc    660
agtcacagct caggtaaagg tgcgcctaaa gatcagtaca aaactgagat cactgtgaat    720
gtgatggaac tgacctttaa aggtgggctg tggaatgaaa gtgcggcgga gaagctcgcc    780
gataaatttg tgaaaagctg ggatgactgg ctggatggca ccacaacacc cgcttcaccg    840
agcgcggatc aaattcagtt ctgctttggt ccggcacatc gcgcacgtca aaaacaagaa    900
gcggacgcga ttaagtaa                                                  918
```

<210> SEQ ID NO 10
<211> LENGTH: 831
<212> TYPE: DNA
<213> ORGANISM: Klebsiella quasipneumoniae

<400> SEQUENCE: 10

```
atggaaagca atgaaattat gtgtaatgta gaacgctggt tggataatca ggctgttaat     60
tcaattggta tatgcttaga tggtctaaat accaccggca acacgcatat ttcgggtggt    120
tcttccgtgc ttactggttc tgccgcaacg caggagcgtg aaattggtaa ggaattaagc    180
cttattactg atattgatga gcttgcggaa aaactggttt ccagccctgc aaattttgtc    240
accacagtca tggggatagc gcaaagtcgc tccgggtgga aaccgcttga acctgaaagt    300
```

gcagacaatg ctgagaattt caaaaaatat attgatcaga taatgaaatt ccctttaatg 360
attgtaacca aaactgacac gaccacagtg acctattccg aaggaaatta tgattcttta 420
attgataata tagccgacat ttactccggc atgagcgatg gagataaaaa ctccgttaag 480
gcagggctta catcactggc gaaaagttgt atgagtcggg taaatgaaaa gcaaaagaaa 540
gtgttattta ctcaaagcac aatgtgtgta aatgatgaag tgactacatc cttttattca 600
tctaatgttg caatggagaa gaaacacagt agcggcaaga atgctccggc agatgaattt 660
agttcagaag tacaggtcag cagagtagag gttaaattta accgtatggc gctgaataag 720
aatattgcta aaaaactatg ttcacttctg ttcaagtcaa ttgatgactg gctcgaagag 780
acaaatacta agcaaaccga taagaaaatc gaattttgtt ttggtgacta a 831

<210> SEQ ID NO 11
<211> LENGTH: 885
<212> TYPE: DNA
<213> ORGANISM: Pseudomonas entomophila

<400> SEQUENCE: 11
atgatcgata tcgatacgat caccaatacc tggggccgct ggaaaacggc gcaatacggc 60
accacttgct ggttcaccga aagcacccag tacgccagga acaaggacac ccgcggctac 120
atgcaatacc agaccaatgt gtccgcgccc aaggacctgg tgtattccag ctacgcccaa 180
agtgacggtg gcagcgcgct gctgggcaag tacgacacga tcaacgatgg cggccaggtc 240
atcgaacaca ccgtcagcct gcaacaaggg ctgagcgaca ccttcacctg gagcgtcacc 300
gagcaactga agattggtgt ctcggtcaag gcgaacgcgg gcattccgct gatcggtggg 360
gccgaaacca cctccacggt ggaaatggac ctgtcctcga cccagggcgc cagcaccacc 420
aagagctcga actacggggc cagcaccacg gtgcccattt ccccccacac ccatggctgg 480
ggcgaagtgg acctgagctt caccgagctc aggacccagt gggtgggtaa tgcctcaatg 540
gtgggttgcg tggcgatctg gttcaacaac aaagtggccc tgaacaataa cggtgactac 600
cactacctct ggttcattcc aatacagcag gtattttccg agatcatcca gcacaacatc 660
atcagcacct cgggctatgt ggtgcagggt ggtggcgtgt tggcgcaggc caccggtacg 720
ttccacagca gcatgggcct gagtctcaag accatcagcc atgaacaacc ctatccgggc 780
gacaacaagg ctgtgcgcac cagctttggc tacaggcgcc tggacaaacc actggagtct 840
gtcgtgttcc cggccgagca tgatttgaac ggccgctcgc gctga 885

<210> SEQ ID NO 12
<211> LENGTH: 861
<212> TYPE: DNA
<213> ORGANISM: Pseudomonas aeruginosa

<400> SEQUENCE: 12
atgaacgata tcgacacgat caccaatgcg tgggggcgtt ggaaaaccgc tcaatacgga 60
accacctgct ggttcactga aagtacccag tacgggcgga acaaggacac tcgcggctat 120
atgcaatatc agaccaacgt ttccgcgccg aaggacttgg tttattccaa ctttgtgcag 180
caggacggcg gtagcgccct gttggggcag tacgacacga tcaacgatgg cagccaggtg 240
attgaacatg tcgtcaactt gcaacaaggg ttagtggaca cctttacctg gagcgtcact 300
gagcagttga aggtcggtgt ggaagtcaag gtgaaggcgg gcattcccct agtgggtggc 360
gctgagacca ccagtacggt ggaagtgtca ctgtcctcta ctcaaggggc gagtaccagc 420
aagtcttcca actatggcgc ctctaccaag gtgcctattt ccccacatag ccacggctgg 480
ggagaggttg acttgagctt tactgagctg cgcactcagt gggtcggtaa tgtcgggctt 540
caaggatgtg tggccatttg gttcaacaac aaagtcgcat tgaacaacga tggcgattac 600
cactacctat ggttcattcc cgtggagcag gtattttggg agtgcatcca gcacaacata 660
gtcaatacct cgggctatgt cgtacaaggc aatggagtgt tggcgcaagc cacaggcacc 720
ttccatagca gcatgggctt gaacttgaag accatcgcgc acgagcggcc ttatccggaa 780
acctcggagg cggtcagaac attctataat tatgccagtc tggttccgga cctagaaacc 840
cgagtccgct cggcagagta g 861

<210> SEQ ID NO 13
<211> LENGTH: 861
<212> TYPE: DNA
<213> ORGANISM: Pseudomonas phage

<400> SEQUENCE: 13
atgaacgata tcgacacgat caccaatgcg tggggacgtt ggaaaacggc tcaatacgga 60
accacctgct ggttcactga aagtacccag tacgggcgga acaaggacac tcgcagctat 120
atgcaacatc agaccaacgt ttccgcgccg aaggacttgg tttactccaa ctttgtgcag 180
caggacggcg gtagcaccct gttggggcag tacgacatga tcaacgaagg cagccaagtg 240
attgaacttg ccgtcaactt gcaacaaggg ttagtggaca ccttcacctg gagcgtcact 300
gagcagttga aggtcggtgt ggaagtcaag gtgaaggcga acattcccct agtgggcggc 360
gctgagatca ccagtacggt ggaattgtca ctgtcctcta cccaaggggc gagtaccagc 420
aagtcttcca actatggcgc ctctaccaag gtgcttattt ccccacatag ccacggctgg 480
ggagaggttg ccttgagctt tactgagctg cgcactcagt gggtcggtaa tgtcgggctt 540
caaggatatg tggcaatttg gttcaacaac aaagtcgcat tgaacaacga tggcgattac 600
cactacctgt ggttcattcc cgtggagcag gtattttggg agtgcgtcca gcacaacata 660
gtcaatacct cgggctatgt cgtacaaggc aatggagtgt tggcgcaagc cacaggcacc 720
ttccatagca gcgtgggctt gaacttgaag accatcgcgc acgagcggcc ctatccggaa 780
acctcggagg cggtcagaac attctataat tatgccagtc tggttccgga cctagaaacc 840
cgagtccgct cggcagagta g 861

<210> SEQ ID NO 14
<211> LENGTH: 861
<212> TYPE: DNA
<213> ORGANISM: Pseudomonas aeruginosa

<400> SEQUENCE: 14
atgaacgata tcgacacgat caccaatgcg tggggacgtt ggaaaacggc tcaatacgga 60
accacctgct ggttcactga aagtacccag tacgggcgga acaaggacac tcgcagctat 120
atgcaacatc agaccaacgt ttccgcgccg aaggacttgg tttactccaa ctttgtgcag 180
caggacggcg gtagcaccct gttggggcag tacgacatga tcaacgaagg cagccaagtg 240
attgaacttg ccgtcaactt gcaacaaggg ttagtggaca ccttcacctg gagcgtcact 300
gagcagttga aggtcggtgt ggaagtcaag gtgaaggcga acattcccct agtgggcggc 360
gctgagatca ccagtacggt ggaattgtca ctgtcctcta cccaaggggc gagtaccagc 420
aagtcttcca actatggcgc ctctaccaag gtgcttattt ccccacatag ccacggctgg 480
ggagaggttg ccttgagctt tactgagctg cgcactcagt gggtcggtaa tgtcgggctt 540

```
caaggatatg tggcaatttg gttcaacaac aaagtcgcat tgaacaacga tggcgattac    600

cactacctgt ggttcattcc cgtggagcag gtattttggg agtgcatcca gcacaacata    660

gtcaatacct cgggctatgt cgtacaaggc aatggagtgt tggcgcaagc cacaggcacc    720

ttccatagca gcgtgggctt gaacttgaag accatcgcgc acgagcggcc ctatccggaa    780

acctcggagg cggtcagaac attctataat tatgccagtc tggttccgga cctagaaacc    840

cgagtccgct cggcagagta g                                              861
```

<210> SEQ ID NO 15
<211> LENGTH: 858
<212> TYPE: DNA
<213> ORGANISM: Pectobacterium wasabiae

<400> SEQUENCE: 15

```
atgaatgata ttgataatat aacgaatgct tggggtaagt ggataaccgc acagtatggt     60

accacttgtt ggtttacaga aagtactcaa tatagtcgta ataaagatac aaaagactat    120

atgcaacacc aaacaaatgt gacgccacca aaagacttgg tgtattcgag tgcggtgcaa    180

agtgatggcg gggcggctat cttaggtaag tatgatattg aaaatggtgg tagccaaata    240

attgaacacg aagttaattt acaacaaggt atagaagatt cgttcacgtg gaatgttacg    300

gagaacgtaa aattaggtgt ttcagttaag cttaaggctg gtgttccatt tgtgggcgct    360

gagacaactt taagtactga actttcgttg tcttctatgc aggggagtac tattactaaa    420

acttctaatt atggggcatc agtaaaagta cctatcactc ctcacaccca tagttgggga    480

cagatcaact tatcttttac tgacatagct acttcttggg ttggtaatgt gaaaatggaa    540

ggatgcgtag ctgtttggtt taataaaaaa gtagctctaa ataatgatgg agattaccac    600

tggttatggt ttgttccgat ccaaagcgtt tttaatgatt gtattcggaa taatattatt    660

gatacccgag gttatattgt gcaatgggat ggagtaattg cgcaagcaag tggaaaattc    720

cacagtagta gagggttaga tatgaaggta atagcttatg agcaaccttt aggcacaaaa    780

cggcaggagg aagctatcca agtaattgtt catgaatttg aaagcaaata tcgtcctatt    840

cctgctaaag tagagtaa                                                  858
```

<210> SEQ ID NO 16
<211> LENGTH: 2478
<212> TYPE: DNA
<213> ORGANISM: Burkholderia ambifaria

<400> SEQUENCE: 16

```
atgtttctca cgagagtcga gcattcgtta agtgactgca agtgcgccca tcagaatatc     60

tacgaaaccg agatctacga cggcacgtca tgggtcgcgc atgggcagat ggttgttctg    120

gaagacgcgg tgacccacaa cggtgtgcat gcgcacaata tcgggtacaa cggttccaac    180

cattcattgg tattgcaggg cggcaccggt cggcaacgct ataacgctcg cttgaatctg    240

acggaatgcg gctcggcctt cgtgggaacg ctggcggttg cgggtgacgc acctcaggca    300

atccggggcg ttgcgctcgc gaatgtcttc gacacgaaac ggtatctcag acccaaaccg    360

aaaaccaaag acgatccggc tgtcaaatgc gatccgaatg caccgtctgt tgcctgggat    420

caattcagca tcaaggcgca gtggattgac aatgttctga ccgttaccta tttactgggc    480

cacgtcgatg tcagcaaccg ggttcgcgtc acagccgtcg atcgccaaaa aggcgagacc    540

acgctggaga tggttcctca acttgatcca ccaggaccgc aagacagctt cgttatcacg    600
```

-continued

```
ctttactccg gaaaccgaac ctttggcggc gaatacacgt ctgacgacga agaagcgtat    660
tgctggttcg gcagttccac gccatcgata tccgagcagc ggtccagggt tttcgcggaa    720
gtgcgcgagg gtgctgcggc gctggcaacg actgcgcaca tctcgacgcc tctcgaaggc    780
gatgccgcca cgcgcacgct gcaggatctc gataacatat cgtcactgac tgtcgtcacc    840
gacaaggacg gcaaccggat gaccatcgat cacgcgcaga cgacctgcgg cggatacttc    900
aacaaatgcc tggtcaacgc gctggacagc aagtggattg aagggatata cgggcatgcc    960
tatttgcttc cgggcggcgt ccagaaagta ttcaacgaca agaagagctt tttccagaag   1020
aaggcggtcc tcggcaccgg gcaaatgctg tacgacaacc tgggcaccag tccgacttac   1080
gccgacctga taaagcgcat caagggcgat gcgatgaagc agagctggaa atcgctgggc   1140
gataccaagg gcggcgacaa agacgagagc ctcgcgtacc aggaggcgag caacgcgctc   1200
tacatcgagg gctatcgcga cggcgttccg gaaatgcaac cgtacttgca ggacaacccc   1260
aagaagtggg cagcggacta cttcgcatgg ctctcggacg aggccaacct gttgacctgg   1320
tcgatccagg tcgccagcaa gatgttcgat aacgtccgcc agcgcatgta cgagtggtac   1380
gtgaaattgc aggttctgga tccggacagc aattacggcc agcgtttcat gaccatcgct   1440
tatgcggcgc tgctcggtgt caattactcg aagtcacgtt ggtccgacga tctgaaacca   1500
ttcctcacga gcctcatcga gcaagcgatc gccggcaagg tcgatccgac actcatggat   1560
cagatccagc aacaagcggc gttggaaaat caggaactgc tcaagacgct gatcacgaca   1620
acggattcga ttcacaatct ggtggacggc atcgccgccg cgattaccga gtaccaattg   1680
aagaagggaa accagcccct atcacggatc gcgcaggatc ccgagctgca gggaatgatc   1740
ggtcaaaggc tggacggcca gcaatacaag gcatggggcg agctctcgag gaaaggcaaa   1800
gtcggcggcg tgttgacagt cgtgttttac ggcgcctcgg ctggatacct tatttactcg   1860
cttgccgaca accccggcag gccacttaca ccgaaggaaa tcatcgagaa aatcaatctc   1920
ggcttgcttg cgctcgcgac attggtcaag ggcgtgcaga agatgatgtc catcggcgtt   1980
ggaagatttc tcgagaattt ttccaaggca gcggaaggcg gggcgtttcg cgctttcgcc   2040
ggagacattg ccacatggtt caaggcgggc gggaagatcg ttcccgaggg caaactcggg   2100
aaagcattcg tgaccatttt cggagagagc agcgccgaat tcatggcacg gcgaatcggg   2160
ccggcgttgg ccgtcgtcgg tatgatcctg tcgtccttca tgctttacga cgcaatcaaa   2220
tcgggcgcgg tgagggagat tgtctttgaa gcgttgaata cgtttttgc gctggcggac   2280
gtcgtgttca tcggactcga gttgttcagc gtcggctggg cagggccggt gggtctcgcc   2340
attgcagtgg tcggcgtcat tgtcatcctc gtgcagttca tctggaacct gatcgaaccg   2400
cctaccccgg caccggatcc gatcaccgag ttcgtcaatg gcccgatggt caaccaaggg   2460
ttcgcggttt ccgcgtaa                                                 2478
```

<210> SEQ ID NO 17
<211> LENGTH: 2409
<212> TYPE: DNA
<213> ORGANISM: Burkholderia ambifaria

<400> SEQUENCE: 17

```
atggcccgat ggtcaaccaa gggttcgcgg tttccgcgta acggcaagtg tcgagccccc     60
gcacggcggc tcgaccccca ctctctttca atcgcacgtt gccaggagat tgccttgctg    120
cttaccgttc aacgatccgc gattcggctg agcgggtctt ccgactcggc tcccgactcc    180
gttatcgagc aattggtcaa cttactgcct gactacagcg gtggccgccg tctgcatgcg    240
```

-continued

```
ctcctggtca atcggctgaa gggagcgttg cccggcaatt attcacagat attcggaacg    300
gggccgtcgt ttcgcagcat tttctttgcc gattaccaac cggatccact gctgccgctc    360
atgtccgaca tgggtctcga tgacggctgg tgggcgaatt tctctgtcgc ggtactgtgc    420
cagtcgattc aggatcttgg cagtcggatt cgagggcaaa tgagagcgga caaaatcaat    480
catgacgtcg cctcgttcaa cgcgacggtg cgcggccgct gcgcgcggcc ctacgcacgc    540
gtcctcgcag ccagttttcc gccgttgatc aatctgttga atcaggtcga ccatgcaacg    600
gccaggcagc agtttcacga cgcgttgctc ggcaacgtca tcaatcggca gctgtggtac    660
caggcgggta tgtggacaag cccggattgg gagatgttca accaatatgc gaaatacatc    720
gcattaggcg cggatgacgc ccaagtggat gcattgatcg atgaactgac tgcagcgggc    780
ctgccgatcc cgccacaggt caatcgcagc aactggcgag gctatgccga agcactgcgc    840
gacaaacccg atatcgacct cgacgatgtc ggcggcgata cggcgaaacc cattcaggaa    900
accacttatc ttcccagcta tggtcgaggc atgcccgcac ggatgccgaa tggcaactgc    960
tatgagttca ccgccggtgg tcagccggga agtccctttc gggctccgcc aagcagttgc   1020
tgctttaccg gcgacacgga agtcctctcg ggggctgggg ttccggtgcc gctgaatcag   1080
gtaaaaccgg gcgataccgt gatgacgcgc gacggtgcgg ctgtcgtggc ttttgtcgcg   1140
cgacctcaac tcggcgaacg gaaactctat cggatcaacg gcggtggccc cgtgtttacc   1200
gatacgcatc ctttcctgaa tgcgtccgca tccgattccc gtgcaatggc ccccgcgatt   1260
cttgccgccg atcccgcaca tctggcctgg atggtaccga cactgagcga agacggcata   1320
ggaaaactga ccacgggatg tgtgctgacc ggccgtcgtc ccgagtcaag cgagtcgttt   1380
ccggtggacg tgaccacggt agagccggtg cctcggggaa ctggcgacga ctacttgtac   1440
gacctgaatc ttcttgtcac gacaggcgcc agacaagaat tctgggccgg caaggacggc   1500
cggttctatc tcgtgtcgcc ggaattcccc gtgctggctc aggcgggcgc ggctgccgtc   1560
gcggtggttg ccgcgctaga ggggctgatt gctgcgggcg gcccgacgct ctccggttgg   1620
ccggtgacaa cgcgggaact cgtgcatcga tttggcgcgg cgattttcga tgccgggctc   1680
gacgcagcac ttcgcacggt gccctcgttt ggctcgccga cgcccgtgcg gccactattc   1740
gagcggatcg acaagctgta tcgggatctc ggttcggtcg acgtcgtcgg cgccagtgcg   1800
atcgcggcat tcttcgacgg attcatgtcc accattgtca cgtggctgac ggcatcggtg   1860
gcattgggct ggagaaaacc ggccgagccc tccggcgaga tcgtcgtggt cacgatattt   1920
gatatggcgc tggcgcccgg cacgcctgtc cagaccgcca gccaaatccg gatggaagtt   1980
cgcgcgcaag gacagagcga atccgcatcc gcgatgatgt ggaaccgcag cggcagggcg   2040
aacacccgtt ttcatcacta tttcgatcag ttgattcacc tcgacagagc caaactgggc   2100
gcgacgggcg gcctgacttt cgcggtcgtg atggatggcg cctccgttcc ggcgttgtca   2160
ggtgcggctc ccctcgtcat cggcgatcga gcccattgct tccagtcggc acagcttttc   2220
gacgcggccg gggcggccgt cggcacgatc cgattcgata ctcgcttgct gacgcggcgg   2280
acggccgagg acgaattggc acacagcggt ctttggacag aggaggcagc cctggcatat   2340
tccaacgcgc tcgggacagc tatgatcgcg ccgatactca cgacgctcga aggcttggcc   2400
ggcagatga                                                           2409
```

<210> SEQ ID NO 18
<211> LENGTH: 2478
<212> TYPE: DNA

<213> ORGANISM: Burkholderia cenocepacia

<400> SEQUENCE: 18
atgtttctca cgagagtcga gcattcgtta agtgactgca agtgcgccca tcagaatatc 60
tacgaaaccg agatctacga cggcacgtca tgggtcgcgc atgggcagat ggttgttctg 120
gaagacgcgg tgacccacaa cggtgtgcat gcgcacaata tcgggtacaa cggttccaac 180
cattcattgg tattgcaggg cggcaccggt cggcaacgct ataacgctcg cttgaatctg 240
acggaatgcg gctcggcctt cgtgggaacg ctggcggttg cgggtgacgc acctcaggca 300
atccggggcg ttgcgctcgc gaatgtcttc gacacgaaac ggtatctcag acccaaaccg 360
aaaaccaaag acgatccggc tgtcaaatgc gatccgaatg caccgtctgt tgcctgggat 420
caattcagca tcaaggcgca gtggattgac aatgttctga ccgttaccta tttactgggc 480
cacgtcgatg tcagcaaccg ggttcgcgtc acagccgtcg atcgcaaaaa aggcgaaacc 540
acgctggaga tggttcctca acttgatcca ccaggaccgc aagacagctt cgttatcacg 600
ctttactccg gaaaccgaac ctttggcggc gaatacacgt ctgacgacga agaagcgtat 660
tgctggttcg gcagttccac gccatcgata tccgagcagc ggtccagggt tttcgcggaa 720
gtgcgcgagg gtgctgcggc gctggcaacg actgcgcgca tctcgacgcc tctcgaaggc 780
gatgccgcca cgcgcacgct gcaggatctc gacaacatat cgtcactgac tgtcgtcacc 840
gacaaggacg gcaaccggat gaccatcgat cacgcgcaga cgacctgcgg cggatacttc 900
aacaaatgcc tggtcaacgc gctggacagc aagtggattg aagggatata cgggcatgcc 960
tattcgcttc cgggcggcgt ccagaaagta ttcaacgaca agaagagctt tttccagaag 1020
aaggcggtcc tcggcaccgg gcaaatgctg tatgacaacc tgggcaccag tccgacttac 1080
gccgacctga taaagcgcat caagggcgat gcgatgaagc agagctggaa atcgctgggc 1140
gataccaagg gcggcgacaa agacgagagc ctcgcgtatc aggaggcgag caacgcgctc 1200
tacatcgagg gctatcgcga cggcgttccg gaaatgcaac cgtacttgca ggacaacccc 1260
aagaagtggg cagcggacta cttcgcgtgg ctctcggacg aggccaacct gttgacctgg 1320
tcgatccagg tcgccagcaa gatgttcgat aacgtccgcc agcgcatgta cgagtggtac 1380
gtgaaattgc aggttctgga tccggacggc aattacggcc agcgtttcat gaccatcgct 1440
tatgcggcgc tgctcggtgt caattactcg aagtcacgtt ggtccgacga tctgaaacca 1500
ttcctcacca gcctcatcga gcaagcgatc gccggcaagg tcgatccgac actcatggat 1560
cagattcagc aacaagcggc gttggaaaat caggaactgc tcaagacgct gatcacgaca 1620
acggattcga ttcacaatct ggtggacggc atcgccgccg cgattaccga gtaccaattg 1680
aagaagggaa accagcccct atcacggatc gcgcaggatc ccgagcttca gggaatgatt 1740
ggtcaaaggc tggacggcca gcaatacaag gcatggggcg agctctcgag gaaaggcaaa 1800
gtcggcggcg tgttgacagt cgtgttttac ggcgcctcgg ctggatacct tatttactcg 1860
cttgccgaca accccggcag gccacttaca ccgaaggaaa tcatcgagaa aatcaatctc 1920
ggcttgcttg cgctcgcgac attggtcaag ggcgtgcaga agatgatgtc cattggcgtt 1980
ggaagatttc tcgagaattt ttccaaggca gcggaaggcg gggcgtttcg cgctttcgcc 2040
ggagacattg ccacatggtt caaggcgggc gggaagatcg ttcccgaggg caaactcggg 2100
aaagcattcg tgaccatttt cggagagagc agcgccgaat tcatggcacg gcgaatcggg 2160
ccggcgttgg ccgtcgtcgg tatgatcctg tcgtccttca tgctttacga cgcaatcaaa 2220
tcgggcgcgg tgagagagat tgtctttgaa gcgttgaata cgtttttgc gctggcggac 2280 gtcgtgttca tcggactcga gttgttcagc gtcggctggg cagggccggt gggtctcgcc 2340
attgcagtgg tcggcgtcat tgtcatcctc gtgcagttca tctggaacct gatcgaaccg 2400
cctaccccgg caccggatcc gatcaccgag ttcgtcaacg gcccgatggt caaccaaggg 2460
ttcgctgttt ccgcgtaa 2478

<210> SEQ ID NO 19
<211> LENGTH: 2049
<212> TYPE: DNA
<213> ORGANISM: Burkholderia cenocepacia

<400> SEQUENCE: 19
atgtccgaca tgggtctcga tgacggctgg tgggcgaatt tctctgtcgc ggtactgtgc 60
cagtcgattc aggatcttgg cagtcggatt cgagggcaaa tgagagcgga caaaatcaat 120
catgacgttg cttcgttcaa cgcgacggtg cgcggccgct gcgcgcggcc ctacgcacgc 180
gtcctcgcag ccagtttttcc gccgttgatc aatctgttga atcaggtcga ccatgcaacg 240
gccagacagc agtttcacga cgcgttgctc ggcaacgtca tcaatcggca gctgtggtac 300
caggcgggta tgtggacaag cccggattgg gagatgttca accaatatgc gaaatacatc 360
gcattaggcg cggatgacgc ccaagtggat gcattgatcg atgaactgac tgcagcgggc 420
ctgccgattc cgccacaggt caatcgcagc aactggcgag gctatgccga agcactgcgc 480
gacaaacccg atatcgacct cgacgatgtc ggcggcgata cggcgaaacc cattcaggaa 540
accacttatc ttcccagcta tggtcgaggc atgcccgcac ggatgccgaa tggcaactgc 600
tatgagttca ccgccggtgg tcagccggga agtccctttc gggctccgcc aagcagttgc 660
tgcttgaccg gcgacacgga agtcctctcg gggcagggg ttccggtgcc gctgaatcag 720
gtaaaaccgg gcgataccgt gatgacgcgt gacggtgcgg ctgtcgtggc ttttgtcgct 780
cgacctcaac tcggcgaacg gaaactctat cggatcaacg gcggtggccc cgtgtttacc 840
gatacgcatc ctttcctgaa tgcgtccgcg tccgattccc gtgcaacggc ccccgcgatt 900
cttgccgccg atccgtcaca tctggcctgg atggtaccga cactgagcga agacggcata 960
ggaaaactga ccacgggatg tgtgctgacc ggccgtcgcc ccgagtcaag cgagtcgttt 1020
ccggtggacg tgaccacggt agagccggtg cctcggggaa ctggcgacga ctacttgtac 1080
gacctgaatc ttcttgtcac gacaggcgcc agacaggaat tctgggccgg caaggacggc 1140
cggttctatc tcgtgtcgcc ggaattcccc gtgctggctc aggcgggcgc ggctgccgtc 1200
gcggtggttg ccgcgctaga ggggctgatt gctgcgggcg gcccgacgct ctccggttgg 1260
ccggtgacaa cgcgggaact cgtgcatcga tttggcgcgg cgattttcga tgccgggctc 1320
gacgcagcac ttcgcacggt gccctcgttt ggctcgccga cgcccgtgcg gccactattc 1380
gagcggatcg acaagctgta tcgggatctc ggttcggtcg acgtcgtcgg cgccagtgcg 1440
atcgcggcat tcttcgacgg attcatgtcc accatcgtca cgtggctgac ggcatcggtg 1500
gcattgggct ggagaaaacc ggccgagccc tccggcgaga tcgtcgtggt cacgatattc 1560
gatatggcgc tggcgcccgg cacgcctgtc cagaccgcca gccaaatccg gatggaagtt 1620
cgcgcgcaag gacagagcga atccgcatcc acgacgatgt ggaaccgcag cggcagggcg 1680
aacacccgtt ttcatcacta tttcgatcag ttgattcacc tcgacagagc caaactgggc 1740
gcgacgggcg gcctgacttt cgcggtcgtg atggatggcg cctccgttcc ggcgttgtcg 1800
ggtgcggctc ccctcgtcat cggcgatcga gcccattgct tccagtcggc acagcttttc 1860
gacgcggccg gaacggccgt cggcacgatc cgattcgata ctcgcttgct tacgcggcgg 1920
acggccgagg acgaattggc acacagcggt ctttggacag aggaggcagc cctggcatat 1980
tccaacgcgc tcgggacagc tatggtcgcg ccgatactca cgacgctcga aggcttggcc 2040
ggcagatga 2049

<210> SEQ ID NO 20
<211> LENGTH: 2295
<212> TYPE: DNA
<213> ORGANISM: Burkholderia cepacia

<400> SEQUENCE: 20
ttgctgctta ccgttcaacg atccgcgatt cggctgcgcg ggacttccga ctcggctccc 60
gactccgtta tcgagcaatt ggtcaactta ctgcctgact acagcggtgg ccgccgtctg 120
catgcgctcc tggtaaatcg gctgaaggga gcgttgcccg gcaattattc acagatattc 180
ggaacggggc cgtcgtttcg cagcattttc tttgccgatt accaaccgga tccactgctg 240
ccgctcatgt ccgacatggg tctcgatgac ggctggtggg cgaatttctc tgtcgcggta 300
ctgtgccagt cgattcagga tcttggcagt cggattcgag ggcaaatgag agcggacaaa 360
atcaatcatg acgtcgcctc gttcaacgcg acggtgcgcg gccgctgcgc gcggccctac 420
gcacgcgtcc tcgcagccag ttttccgccg ttgatcaatc tgttgaatca ggtcgaccat 480
gcaacggcca gacagcagtt tcacgacgcg ttgctcggca acgtcatcaa tcggcagctg 540
tggtaccagg cgggtatgtg gacaagcccg gattgggaga tgttcaacca atatgcgaaa 600
tacatcgcat taggcgcgga tgacgcccaa gtggatgcat tgatcgatga actgactgca 660
gcgggcctgc cgatcccgcc acaggtcaat cgcagcaact ggcgaggcta tgccgaagca 720
ctgcgcgaca aacccgatat cgacctcgac gatgtcggcg gcgatacggc gaaacccatt 780
caggaaacca cttatcttcc cagctatggt cgaggcatgc ccgcacggat gccgaatggc 840
aactgctatg agttcaccgc cggtggtcag ccgggaagtc cctttcgggc tccgccaagc 900
agttgctgct ttaccggcga cacggaagtc ctctcggggg ctggggttcc ggtgccgctg 960
aatcaggtaa aaccgggcga taccgtgatg acgcgcgacg gtgcggctgt cgtggctttt 1020
gtcgcgcgac ctcaactcgg cgaacggaaa ctctatcgga tcaacggcgg tggccccgtg 1080
tttaccgata cgcatccttt cctgaatgcg tccgcatccg attcccgtgc aatggccccc 1140
gcgattcttg ccgccgatcc cgcacatctg gcctggatgg taccgacact gagcgaagac 1200
ggcattggaa aactgaccac gggatgtgtg ctgaccggcc gtcgtcccga gtcaagcgag 1260
tcgtttccgg tggacgtgac cacggtagag ccggtgcctc ggggaactgg cgacgactac 1320
ttgtacgacc tgaatcttct tgtcacgaca ggtgccagac aagaattctg ggccggcaag 1380
gacggccggt tctatctcgt gtcgccggaa ttccccgtgc tggctcaggc gggcgcggct 1440
gccgtcgcgg tggttgccgc gctagagggg ctgattgctg cgggcggccc gacgctctcc 1500
ggttggccgg tgacaacgcg ggaactcgtg catcgatttg gcgcggcgat tttcgatgcc 1560
gggctcgacg cagcacttcg cacggtgccc tcgtttggct cgccgacgcc cgtgcggcca 1620
ctattcgagc ggatcgacaa gctgtatcgg gatctcggtt cagtcgacgt cgtcggcgcc 1680
agtgcgatcg cggcattctt cgacggattc atgtccacca ttgtcacgtg gctgacggca 1740
tcggtggcat tgggctggag aaaaccggcc gagccctccg gcgagatcgt cgtggtcacg 1800
atatttgata tggcgctggc gcccggcacg cctgtccaga ccgccagcca aatccggatg 1860
gaagttcgcg cgcaaggaca gagcgaatcc gcatccgcga tgatgtggaa ccgcagcggc 1920

-continued agggcgaaca cccgttttca tcactatttc gatcagttga ttcacctcga cagagccaaa 1980
ctgggcgcga cgggcggcct gactttcgcg gtcgtgatgg atggcgcctc cgttccggcg 2040
ttgtcgggtg cggctcccct cgtcatcggc gatcgagccc attgcttcca gtcggcacag 2100
cttttcgacg cggccggggc ggccgtcggc acgatccgat tcgatactcg cttgctgacg 2160
cggcggacgg ccgaggacga attggcacac agcggtcttt ggacagagga ggcagccctg 2220
gcatattcca acgcgctcgg gacagctatg atcgcgccga tactcacgac gctcgaaggc 2280
ttggccggca gatga 2295

<210> SEQ ID NO 21
<211> LENGTH: 2478
<212> TYPE: DNA
<213> ORGANISM: Burkholderia cepacia

<400> SEQUENCE: 21
atgtttctca cgagagtcga gcattcgtta agtgactgca agtgcgccca tcagaatatc 60
tacgaaaccg agatctacga cggcacgtca tgggtcgcgc acgggcagat ggttgttctg 120
gaagacgcgg tgacccacaa cggtgtgcat gcgcacaata tcgggtacaa cggttccaac 180
cattcactgg tattgcaggg cggcaccggt cggcaacgct ataacgctcg tctgaacctg 240
acggaatgcg gctcggcctt cgtgggaacg ctggctgttg cgggtgacgc acctcaggca 300
atccggggcg ttgcgctcgc gaatgtcttc gacacgaaac ggtatctcag acccaaaccg 360
aaaaccaaag acgatccggc tgtcaaatgc gatccgaatg caccgtctgt tgcctgggat 420
caattcagca tcaaggcgca gtggattgac aatgttctga ccgttaccta tttactgggc 480
ctcgtcgatg tcagcaaccg ggttcgcgtc acagccgtcg atcgcaaaaa aggcgagacc 540
acgctggaga tggttcctca acttgatcca ccaggaccgc aagacagctt cgttatcacg 600
ctttactccg gaaaccgaac ctttggcggc gaatacacgt ctgacgacga agaagcgtat 660
tgctggttcg gcagttccac gccatcgata tccgagcagc ggtccagggt tttcgcggaa 720
gtgcgcgagg gtgctgcggc gctggcaacg actgcgcgca tctcgacgcc tctcgaaggc 780
gatgccgcca cgcgcacgct gcaggatctc gataacatat cgtcactgac tgtcgtcacc 840
gacaaggacg gcaaccggat gaccatcgat cacgcgcaga cgacctgcgg cggatatttc 900
aacaaatgcc tggtcaacgc gctggacagc aagtggattg aagggatata cgggcatgcc 960
tattcgcttc cgggcggcgt ccagaaagta ttcaacgaca agaagagctt tttccagaag 1020
aaggcggtcc tcggcaccgg gcaaatgctg tacgacaacc tgggcaccag tccgacttac 1080
gccgacctga taaagcgcat caagggcgat gcgatgaagc agagctggaa atcgctgggc 1140
gataccaagg gcggcgacaa agacgagagc ctcgcgtacc aggaggcgag caacgcgctc 1200
tacatcgagg gctatcgcga cggcgttccg gaaatgcaac cgtacttgca ggacaacccc 1260
aagaagtggg cagcggacta cttcgcatgg ctctcggacg aggccaacct gttgacctgg 1320
tcgatccagg tcgccagcaa gatgtttgat aacgtccgcc agcgcatgta cgagtggtac 1380
gtgaaattgc aggttctgga tccggacggc aattacggcc agcgtttcat gaccatcgct 1440
tatgcggcgc tgctcggtgt caattactcg aagtcacgtt ggtccgacga tctgaaacca 1500
ttcctcacga gtctcatcga gcaagcgatc gccggcaagg tcgatccgac actcatggat 1560
cagatccagc aacaagcggc gttggaaaat caggaactgc tcaagacgct gatcacgaca 1620
acggattcga ttcacaatct ggtggacggc atcgccgccg cgattaccga gtaccaattg 1680
aagaagggaa accagccctt atcacggatc gcgcaggatc ccgagcttca gggaatgatt 1740
ggtcaaaggc tggacggcca gcaatacaag gcatggggcg agctctcgag gaaaggcaaa 1800
gtcggcggcg tgttgacagt cgtgttttac ggcgcctcgg ctggatacct tatttactcg 1860
cttgccgaca accccggcag gccacttaca ccgaaggaaa tcatcgagaa aatcaatctc 1920
ggcttgcttg cgctcgcgac attggtcaag ggcgtgcaga agatgatgtc cattggcgtt 1980
ggaagatttc tcgagaattt ttccaaggca gcggaaggcg gggcgtttcg cgctttcgcc 2040
ggagacattg ccacatggtt caaggcgggc gggaagatcg ttcccgaggg caaactcggg 2100
aaagcattcg tgaccatttt cggagagagc agcgccgaat tcatggcacg gcgaatcggg 2160
ccggcgttgg ccgtcgtcgg tatgatcctg tcgtccttca tgctttacga cgcaatcaaa 2220
tcgggcgcgg tgagagagat tgtctttgaa gcgttgaata cgtttttttgc gctggcggac 2280 gtcgtgttca tcggactcga gttgttcagc gtcggctggg cagggccggt gggtctcgcc 2340
attgcagtgg tcggcgtcat tgtcatcctc gtgcagttca tctggaacct gatcgaaccg 2400
cctaccccgg cgccggatcc gatcaccgag ttcgtcaatg gcccgatggt caaccaaggg 2460
ttcgctgttt ccgcgtaa 2478

<210> SEQ ID NO 22
<211> LENGTH: 2295
<212> TYPE: DNA
<213> ORGANISM: Burkholderia cepacia

<400> SEQUENCE: 22
ttgctgctta ccgttcaacg atccgcgatt cggctgcgcg ggacttccga ctcggctccc 60
gactccgtta tcgagcaatt ggtcaactta ctgcctgact acagcggtgg ccgccgtctg 120
catgcgctcc tggtaaatcg gctgaaggga gcgttgcccg gcaattattc acagatattc 180
ggaacggggc cgtcgtttcg cagcattttc tttgccgatt accaaccgga tccactgctg 240
ccgctcatgt ccgacatggg tctcgatgac ggctggtggg cgaatttctc tgtcgcggta 300
ctgtgccagt cgattcagga tcttggcagt cggattcgag ggcaaatgag agcggacaaa 360
atcaatcatg acgtcgcctc gttcaacgcg acggtgcgcg gccgctgcgc gcggccctac 420
gcacgcgtcc tcgcagccag ttttccgccg ttgatcaatc tgttgaatca ggtcgaccat 480
gcaacggcca gacagcagtt tcacgacgcg ttgctcggca acgtcatcaa tcggcagctg 540
tggtaccagg cgggtatgtg gacaagcccg gattgggaga tgttcaacca atatgcgaaa 600
tacatcgcat taggcgcgga tgacgcccaa gtggatgcat tgatcgatga actgactgca 660
gcgggcctgc cgatcccgcc acaggtcaat cgcagcaact ggcgaggcta tgccgaagca 720
ctgcgcgaca aacccgatat cgacctcgac gatgtcggcg gcgatacggc gaaacccatt 780
caggaaacca cttatcttcc cagctatggt cgaggcatgc ccgcacggat gccgaatggc 840
aactgctatg agttcaccgc cggtggtcag ccgggaagtc cctttcgggc tccgccaagc 900
agttgctgct ttaccggcga cacggaagtc ctctcggggg ctggggttcc ggtgccgctg 960
aatcaggtaa aaccgggcga taccgtgatg acgcgcgacg gtgcggctgt cgtggctttt 1020
gtcgcgcgac ctcaactcgg cgaacggaaa ctctatcgga tcaacggcgg tggccccgtg 1080
tttaccgata cgcatccttt cctgaatgcg tccgcatccg attcccgtgc aatggccccc 1140
gcgattcttg ccgccgatcc cgcacatctg gcctggatgg taccgacact gagcgaagac 1200
ggcattggaa aactgaccac gggatgtgtg ctgaccggcc gtcgtcccga gtcaagcgag 1260
tcgtttccgg tggacgtgac cacggtagag ccggtgcctc ggggaactgg cgacgactac 1320
ttgtacgacc tgaatcttct tgtcacgaca ggtgccagac aagaattctg ggccggcaag 1380
gacggccggt tctatctcgt gtcgccggaa ttccccgtgc tggctcaggc gggcgcggct 1440
gccgtcgcgg tggttgccgc gctagagggg ctgattgctg cgggcggccc gacgctctcc 1500
ggttggccgg tgacaacgcg ggaactcgtg catcgatttg gcgcggcgat tttcgatgcc 1560
gggctcgacg cagcacttcg cacggtgccc tcgtttggct cgccgacgcc cgtgcggcca 1620
ctattcgagc ggatcgacaa gctgtatcgg gatctcggtt cagtcgacgt cgtcggcgcc 1680
agtgcgatcg cggcattctt cgacggattc atgtccacca ttgtcacgtg gctgacggca 1740
tcggtggcat tgggctggag aaaaccggcc gagccctccg gcgagatcgt cgtggtcacg 1800
atatttgata tggcgctggc gcccggcacg cctgtccaga ccgccagcca aatccggatg 1860
gaagttcgcg cgcaaggaca gagcgaatcc gcatccgcga tgatgtggaa ccgcagcggc 1920
agggcgaaca cccgttttca tcactatttc gatcagttga ttcacctcga cagagccaaa 1980
ctgggcgcga cgggcggcct gactttcgcg gtcgtgatgg atggcgcctc cgttccggcg 2040
ttgtcgggtg cggctcccct cgtcatcggc gatcgagccc attgcttcca gtcggcacag 2100
cttttcgacg cggccggggc ggccgtcggc acgatccgat tcgatactcg cttgctgacg 2160
cggcggacgg ccgaggacga attggcacac agcggtcttt ggacagagga ggcagccctg 2220
gcatattcca acgcgctcgg gacagctatg atcgcgccga tactcacgac gctcgaaggc 2280
ttggccggca gatga 2295

<210> SEQ ID NO 23
<211> LENGTH: 2049
<212> TYPE: DNA
<213> ORGANISM: Burkholderia cepacia

<400> SEQUENCE: 23
atgtccgaca tgggtctcga tgacggctgg tgggcgaatt tctctgtcgc ggtactgtgc 60
cagtcgattc aggatcttgg cagtcggatt cgagggcaaa tgagagcgga caaaatcaat 120
catgacgtcg cctcgttcaa cgcgacggtg cgcggccgct gcgcgcggcc ctacgcacgc 180
gtcctcgcag ccagttttcc gccgttgatc aatctgttga atcaggtcga ccatgcaacg 240
gccagacaac agtttcacga cgcgttgctc ggcaacgtca tcaatcggca gctgtggtac 300
caggcgggta tgtggacaag cccggattgg gagatgttca accaatatgc gaaatacatc 360
gcattaggcg cggatgacgc ccaagtggat gcattgatcg atgaactgac tgcagcgggc 420
ctgccgatcc cgccacaggt caatcgcagc aactggcgag gctatgccga agcactgcgc 480
gacaaacccg atatcgacct cgacgatgtc ggcggcgata cggcgaaacc cattcaggaa 540
accacttatc ttcccagcta tggtcgaggc atgcccgcac ggatgccgaa tggcaactgc 600
tatgagttca ccgccggtgg tcagccggga agtccctttc gggctccgcc aagcagttgc 660
tgcttgaccg gcgacacgga agtcctctcg ggggctgggg ttccggtgcc gctgaatcag 720
gtaaaaccgg gcgataccgt gatgacgcgc gacggtgcgg ctgtggtggc ttttgtcgcg 780
cgacctcaac tcggcgaacg gaaactctat cggatcaacg gcggtggccc cgtgtttacc 840
gatacgcatc ctttcctgaa tgcgtccgcg tccgattccc gtgcaacggc ccccgcgatt 900
cttgccgccg atcccgcaca tctggcctgg atggtaccga cactgagcga ggacggcata 960
ggaaaactga ccacgggatg tgtgctgacc ggccgtcgtc ccgagtcaag cgagtcgttt 1020
ccggtggacg tgaccacggt agagccggtg cctcggggaa ctggcgacga ctacttgtac 1080

-continued

```
gacctgaatc ttcttgtcac gacaggcgcc agacaggaat tctgggccgg caaggacggc   1140

cggttctatc tcgtgtcgcc ggaattcccc gtgctggctc aggcgggcgc ggctgccgtc   1200

gcggtggttg ccgcgctaga ggggctgatt gctgcgggcg gcccgacgct ctccggttgg   1260

ccggtgacaa cgcaggaact cgtgcatcga tttggcgcgg cgattttcga tgccgggctc   1320

gacgcagcac ttcgcacggt gccctcgttt ggctcgccga cgcccgtgcg gccactattc   1380

gagcggatcg acaagctgta tcgggatctc ggttcggtcg acgtcgtcgg cgccagtgcg   1440

atcgcggcat tcttcgacgg attcatgtcc accatcgtca cgtggctgac ggcatcggtg   1500

gcattgggct ggagaaaacc ggccgagccc tccggcgaga tcgtcgtggt cacgatattc   1560

gatatggcgc tggcgcccgg cacgcctgtc cagaccgcca gccaaatccg gatggaagtt   1620

cgcgcgcaag gacagagcga atccgcatcc acgatgatgt ggaaccgcag cggcagggcg   1680

aacacccgtt ttcatcacta tttcgatcag ttgattcacc tcgacagagc caaactgggc   1740

gcgacgggcg gcctgacttt cgcggtcgtg atggatggcg cctccgttcc ggcgttgtcg   1800

ggtgcggctc ccctcgtcat cggcgatcga gcccattgct tccagtcggc acagcttttc   1860

gacgcggccg gaacggccgt cggcacgatc cgattcgata ctcgcttgct tacgcggcgg   1920

acggccgagg acgaattggc acacagcggt ctttggacag aggaggcagc cctggcatat   1980

tccaacgcgc tcgggacagc aatggtcgcg ccgatactca cgacgctcga aggcttggcc   2040

ggcagatga                                                           2049
```

<210> SEQ ID NO 24
<211> LENGTH: 2478
<212> TYPE: DNA
<213> ORGANISM: Burkholderia cepacia

<400> SEQUENCE: 24

```
atgtttctca cgagagtcga gcattcgtta agtgactgca agtgcgccca tcagaatatc     60

tacgaaaccg agatctacga cggcacgtca tgggtcgcgc atgggcagat ggttgttctg    120

gaagacgcgg tgacccacaa cggtgtgcat gcgcacaata tcgggtacaa cggttccaac    180

cattcattgg tattgcaggg cggcaccggt cggcaacgct ataacgctcg cttgaatctg    240

acggaatgcg gctcggcctt cgtgggaacg ctggaagttg cgggtgacgc acctcaggca    300

atccggggcg ttgcgctcgc gaatgtcttc gacacgaaac ggtatctcag acccaaaccg    360

aaaaccaaag acgatccggc tgtcaaatgc gatccgaatg caccgtctgt tgcctgggac    420

caattcagca tcaaggcgca gtggattgac aatgttctga ccgttaccta tttactgggc    480

cacgtcgatg tcagcaaccg ggttcgcgtc acagccgtcg atcgccaaaa aggcgagacc    540

acgctggaga tggttcctca acttgatcca ccaggaccgc aagacagctt cgttatcacg    600

ctttactccg gaaaccgaac ctttggcggc gaatacacgt ctgacgacga agaagcgtat    660

tgctggttcg gcagttccac gccatcgata tccgagcagc ggtccagggt tttcgcggaa    720

gtgcgcgagg gtgctgcggc gctggcaacg actgcgcgca tctcgacgcc tctcgaaggc    780

gatgccgcca cgcgcacgct gcaggatctc gataacatat cgtcactgac tgtcgtcacc    840

gacaaggacg gcaaccggat gaccatcgat cacgcgcaga cgacctgcgg cggatacttc    900

aacaaatgcc tggtcaacgc gctggacagc aagtggattg aagggatata cgggcatgcc    960

tatttgcttc cgggcggcgt ccagaaagta ttcaacgaca agaagagctt tttccagaag   1020

aaggcggtcc tcggcaccgg gcaaatgctg tacgacaacc tgggcaccag tccgacttac   1080

gccgacctga taaagcgcat caagggcgat gcgatgaagc agagctggaa atcgctgggc   1140
```

```
gataccaagg gcggcgacaa agacgagagc ctcgcgtacc aggaggcgag caacgcgctc   1200

tacatcgagg gctatcgcga cggcgttccg gaaatgcaac cgtacttgca ggacaacccc   1260

aagaagtggg cagcggacta cttcgcatgg ctctcggacg aggccaacct gttgacctgg   1320

tcgatccagg tcgccagcaa gatgttcgat aacgtccgcc agcgcatgta cgagtggtac   1380

gtgaaattgc aggttctgga tccggacagc aattacggcc agcgtttcat gaccatcgct   1440

tatgcggcgc tgctcggtgt caattactcg aagtcacgtt ggtccgacga tctgaaacca   1500

ttcctcacga gcctcatcga gcaagcgatc gccggcaagg tcgatccgac actcatggat   1560

cagatccagc aacaagcggc gttggaaaat caggaactgc tcaagacgct gatcacgaca   1620

acggattcga ttcacaatct ggtggacggc atcgccgccg cgattaccga gtaccaattg   1680

aagaagggaa accagcccct atcacggatc gcgcaggatc ccgagctgca gggaatgatt   1740

ggtcaaaggc tggacggcca gcaatacaag gcatggggcg agctctcgag gaaaggcaaa   1800

gtcggcggcg tgttgacagt cgtgttttac ggcgcctcgg ctggatacct tatttactcg   1860

cttgccgaca accccggcag gccacttaca ccgaaggaaa tcatcgagaa aatcaatctc   1920

ggcttgcttg cgctcgcgac attggtcaag ggcgtgcaga agatgatgtc cattggcgtt   1980

ggaagatttc tcgagaattt ttccaaggca gcggaaggcg gggcgtttcg cgctttcgcc   2040

ggagacattg ccacatggtt caaggcgggc gggaagatcg ttcccgaggg caaactcggg   2100

aaagcattcg tgaccatttt cggagagagc agcgccgaat tcatggcacg gcgaatcggg   2160

ccggcgttgg ccgtcgtcgg tatgatcctg tcgtccttca tgctttacga cgcaatcaaa   2220

tcgggcgcgg tgagggagat tgtctttgaa gcgttgaata cgttttttgc gctggcggac   2280

gtcgtgttca tcggactcga gttgttcagc gtcggctggg cagggccggt gggtctcgcc   2340

attgcagtgg tcggcgtcat tgtcatcctc gtgcagttca tctggaacct gatcgaaccg   2400

cctaccccgg caccggatcc gatcaccgag ttcgtcaatg gcccgatggt caaccaaggg   2460

ttcgctgttt ccgcgtaa                                                 2478
```

<210> SEQ ID NO 25
<211> LENGTH: 2295
<212> TYPE: DNA
<213> ORGANISM: Burkholderia cepacia

<400> SEQUENCE: 25

```
ttgctgctta ccgttcaacg atccgcgatt cggctgagcg ggtcttccga ctcggctccc     60

gactccgtta tcgagcaatt ggtcaactta ctgcctgact acagcggtgg ccgccgtctg    120

catgcgctcc tggtcaatcg gctgaaggga gcgctgcccg gcaattattc acagatattc    180

ggaacggggc cgtcgtttcg cagcattttc tttgccgatt accaaccgga tccactgctg    240

ccgctcatgt ccgacatggg tctcgatgac ggctggtggg cgaatttctc tgtcgcggta    300

ctgtgccagt cgattcagga tcttggcagt cggattcgag ggcaaatgag agcggacaaa    360

atcaatcatg acgtcgcctc gttcaacgcg acggtgcgcg gccgctgcgc gcggccctac    420

gcacgcgtcc tcgcagccag ttttccgccg ttgatcaatc tgttgaatca ggtcgaccat    480

gcaacggcca gacagcagtt tcacgacgcg ttgctcggca acgtcatcaa tcggcagctg    540

tggtaccagg cgggtatgtg gacaagcccg gattgggaga tgttcaacca atatgcgaaa    600

tacatcgcat taggcgcgga tgacgcccaa gtggatgcat tgatcgatga actgactgca    660

gcgggcctgc cgatcccgcc acaggtcaat cgcagcaact ggcgaggcta tgccgaagca    720
```

ctgcgcgaca aacccgatat cgacctcgac gatgtcggcg gcgatacggc gaaacccatt 780
caggaaacca cttatcttcc cagctatggt cgaggcatgc ccgcacggat gccgaatggc 840
aactgctatg agttcaccgc cggtggtcag ccgggaagtc cctttcgggc tccgccaagc 900
agttgctgct ttaccggcga cacggaagtc ctctcggggg ctggggttcc ggtgccgctg 960
aatcaggtaa aaccgggtga taccgtgatg acgcgcgacg gtgcggctgt cgtggctttt 1020
gtcgcgcgac ctcaactcgg cgaacggaaa ctctatcgga tcaacggcgg tggccccgtg 1080
tttaccgata cgcatccttt cctgaatgcg tccgcatccg attcccgtgc aatggccccc 1140
gcgattcttg ccgccgatcc cgcacatctg gcctggatgg taccgacact gagcgaagac 1200
ggcataggaa aactgaccac gggatgtgtg ctgaccggcc gtcgtcccga gtcaagcgag 1260
tcgtttccgg tggacgtgac cacggtagag ccggtgcctc ggggaactgg cgacgactac 1320
ttgtacgacc tgaatcttct tgtcacgaca ggcgccagac aagaattctg ggccggcaag 1380
gacggccggt tctatctcgt gtcgccggaa ttccccgtgc tggctcaggc gggcgcggct 1440
gccgtcgcgg tggttgccgc gctagagggg ctgattgctg cgggcggccc gacgctctcc 1500
ggttggccgg tgacaacgcg ggaactcgtg catcgatttg gcgcggcgat tttcgatgcc 1560
gggctcgacg cagcacttcg cacggtgccc tcgtttggct cgccgacgcc cgtgcggcca 1620
ctattcgagc ggatcgacaa gctgtatcgg gatctcggtt cggtcgacgt cgtcggcgcc 1680
agtgcgatcg cggcattctt cgacggattc atgtccacca ttgtcacgtg gctgacggca 1740
tcggtggcat tgggctggag aaaaccggcc gagccctccg gcgagatcgt cgtggtcacg 1800
atatttgata tggcgctggc gcccggcacg cctgtccaga ccgccagcca aatccggatg 1860
gaagttcgcg cgcaaggaca gagcgaatcc gcatccgcga tgatgtggaa ccgcagcggc 1920
agggcgaaca cccgttttca tcactatttc gatcagttga ttcacctcga cagagccaaa 1980
ctgggcgcga cgggcggcct gactttcgcg gtcgtgatgg atggcgcctc cgttccggcg 2040
ttgtcaggtg cggctcccct cgtcatcggc gatcgagccc attgcttcca gtcggcacag 2100
cttttcgacg cggccggggc ggccgtcggc acgatccgat tcgatactcg cttgcttacg 2160
cggcggacgg ccgaggacga attggcacac agcggtcttt ggacagagga ggcagccctg 2220
gcatattcca acgcgctcgg gacagctatg atcgcgccga tactcacgac gctcgaaggc 2280
ttggccggca gatga 2295

<210> SEQ ID NO 26
<211> LENGTH: 2478
<212> TYPE: DNA
<213> ORGANISM: Burkholderia cepacia

<400> SEQUENCE: 26
atgtttctca cgagagtcga gcattcgtta agtgactgca agtgcgccca tcagaatatc 60
tacgaaaccg agatctacga cggcacgtca tgggtcgcgc atgggcagat ggttgttctg 120
gaagacgcgg tgacccacaa cggagtgcac gcgcacaata ttgggtacaa cggttccaac 180
cattcattgg tattgcaggg cggcaccggt cggcaacgct ataacgctcg cttgaatctg 240
acggaatgcg gctcggcctt cgtgggaacg ctggaagttg cgggtgacgc acctcgggca 300
atccggggcg ttgcgctcgc gaatgtcttc gacacgaaac ggtatctcag acccaaaccg 360
aaaaccaaag acgatccggc tgtcaaatgc gatccgaatg caccgtctgt tgcctgggat 420
caattcagca tcaaggcgca gtggattgac aatgttctga ccgttaccta tttactgggc 480
cacgtcgatg tcagcaaccg ggttcgcgtc acagccgtcg atcgccaaaa aggcgagacc 540

-continued acgctggaga tggttcctca acttgatcca ccaggaccgc aagacagctt cgttatcacg 600
ctttactccg gaaaccgaac ctttggcggc gaatacacgt ctgacgacga agaagcgtat 660
tgctggttcg gcagttccac gccatcgata tccgagcagc ggtccagggt tttcgcggaa 720
gtgcgcgagg gtgctgcggc gctggcaacg actgcgcgca tctcgacgcc tctcgaaggc 780
gatgccgcca cgcgcacgct gcaggatctc gataacatat cgtcactgac tgtcgtcacc 840
gacaaggacg gcaaccggat gaccatcgat cacgcgcaga cgacctgcgg cggatacttc 900
aacaaatgcc tggtcaacgc gctggacagc aagtggattg aagggatata cgggcatgcc 960
tatttgcttc cgggcggcgt ccagaaagta ttcaacgaca agaagagctt tttccagaag 1020
aaggcggtcc tcggcaccgg gcaaatgctg tacgacaacc tgggcaccag tccgacttac 1080
gccgacctga taaagcgcat caagggcgat gcgatgaagc agagctggaa atcgctgggc 1140
gataccaagg gcggcgacaa agacgagagc ctcgcgtacc aggaggcgag caacgcgctc 1200
tacatcgagg gctatcgcga cggcgttccg gaaatgcaac cgtacttgca ggacaacccc 1260
aagaagtggg cagcggacta cttcgcatgg ctctcggacg aggccaacct gttgacctgg 1320
tcgatccagg tcgccagcaa gatgttcgat aacgttcgcc agcgcatgta cgagtggtac 1380
gtgaaattgc aggttctgga tccggacagc aattacggcc agcgtttcat gaccatcgct 1440
tatgcggcgc tgctcggtgt caattactcg aagtcacgtt ggtccgacga tctgaaacca 1500
ttcctcacga gcctcatcga gcaagcgatc gccggcaagg tcgatccgac actcatggat 1560
cagatccagc aacaagcggc gttggaaaat caggaactgc tcaagacgct gatcacgaca 1620
acggattcga ttcacaatct ggtggacggc atcgccgccg cgattaccga gtaccaattg 1680
aagaagggaa accagcccct atcacggatc gcgcaggatc ccgagctgca gggaatgatt 1740
ggtcaaaggc tggacggtca gcaatacaag gcatggggcg agctctcgag gaaaggcaaa 1800
gtcggcggcg tgttgacagt cgtgttttac ggcgcctcgg ctggatacct tatttactcg 1860
cttgccgaca accccggcag gccacttaca ccgaaggaaa tcatcgagaa aatcaatctc 1920
ggcttgcttg cgctcgcgac attggtcaag ggcgtgcaga agatgatgtc catcggcgtt 1980
ggaagatttc tcgagaattt ttccaaggca gcggaaggcg gggcgtttcg cgctttcgcc 2040
ggagacattg ccacatggtt caaggcgggc gggaagatcg ttcccgaggg caaactcggg 2100
aaagcattcg tgaccatttt cggagagagc agcgccgaat tcatggcacg gcgaatcggg 2160
ccggcgttgg ccgtcgtcgg tatgatcctg tcgtccttca tgctttacga cgcaatcaaa 2220
tcgggggcgg tgagggagat tgtctttgaa gcgttgaata cgtttttgc gctggcggac 2280 gtcgtgttca tcggactcga gttgttcagc gtcggctggg cagggccggt gggtctcgcc 2340
attgcagtgg tcggcgtcat tgtcatcctc gtgcagttca tctggaacct gatcgaaccg 2400
cctaccccgg caccggatcc gatcaccgag ttcgtcaatg gcccgatggt caaccaaggg 2460
ttcgctgttt ccgcgtaa 2478

<210> SEQ ID NO 27
<211> LENGTH: 1164
<212> TYPE: DNA
<213> ORGANISM: Burkholderia cepacia

<400> SEQUENCE: 27
atggcccccg cgattcttgc cgccgatccc gcacatctgg cctggatggt accgacactg 60
agcgaagacg gcattggaaa actgaccacg ggatgtgtgc tgaccggccg tcgtcccgag 120

```
tcaagcgagt cgtttccggt ggacgtgacc acggtagagc cggtgcctcg gggaactggc    180

gacgactact tgtacgacct gaatcttctt gtcacgacag gtgccagaca agaattctgg    240

gccggcaagg acggccggtt ctatctcgtg tcgccggaat tccccgtgct ggctcaggcg    300

ggcgcggctg ccgtcgcggt ggttgccgcg ctagaggggc tgattgctgc gggcggcccg    360

acgctctccg gttggccggt gacaacgcgg gaactcgtgc atcgatttgg cgcggcgatt    420

ttcgatgccg ggctcgacgc agcacttcgc acggtgccct cgtttggctc gccgacgccc    480

gtgcggccac tattcgagcg gatcgacaag ctgtatcggg atctcggttc agtcgacgtc    540

gtcggcgcca gtgcgatcgc ggcattcttc gacggattca tgtccaccat tgtcacgtgg    600

ctgacggcat cggtggcatt gggctggaga aaaccggccg agccctccgg cgagatcgtc    660

gtggtcacga tatttgatat ggcgctggcg cccggcacgc ctgtccagac cgccagccaa    720

atccggatgg aagttcgcgc gcaaggacag agcgaatccg catccgcgat gatgtggaac    780

cgcagcggca gggcgaacac ccgttttcat cactatttcg atcagttgat tcacctcgac    840

agagccaaac tgggcgcgac gggcggcctg actttcgcgg tcgtgatgga tggcgcctcc    900

gttccggcgt tgtcgggtgc ggctcccctc gtcatcggcg atcgagccca ttgcttccag    960

tcggcacagc ttttcgacgc ggccggggcg gccgtcggca cgatccgatt cgatactcgc   1020

ttgctgacgc ggcggacggc cgaggacgaa ttggcacaca gcggtctttg gacagaggag   1080

gcagccctgg catattccaa cgcgctcggg acagctatga tcgcgccgat actcacgacg   1140

ctcgaaggct tggccggcag atga                                          1164
```

<210> SEQ ID NO 28
<211> LENGTH: 2295
<212> TYPE: DNA
<213> ORGANISM: Burkholderia cepacia

<400> SEQUENCE: 28

```
ttgctgctta ccgttcaacg aaccgcgatt cggctgagcg ggtcttccga ctcggctccc     60

gactccgtta tcgagcaatt ggtcaactta ctgcctgact acagcggtgg ccgccgtctg    120

catgcgctac tggtcaatcg gctgaaggga gcgctgcccg gcaattattc acagatattc    180

ggaacggggc cgtcgtttcg cagcattttc ttcgccgatt accaaccgga tccactgctg    240

ccgctcatgt ccgacatggg tctcgatgac ggctggtggg cgaatttctc tgtcgcggta    300

ctgtgccagt cgattcagga tcttggcagt cggattcgag ggcaaatgag agcggacaaa    360

atcaatcatg acgttgcttc gttcaacgcg acggtgcgcg gccgctgcgc gcggccctac    420

gcacgcgtcc tcgcagccag ttttccgccg ttgatcaatc tgttgaatca ggtcgaccat    480

gcaacggcca gacagcagtt tcacgacgcg ttgctcggca acgtcatcaa tcggcagctg    540

tggtaccagg cgggtatgtg gacaagcccg gattgggaga tgttcaacca atatgcgaaa    600

tacatcgcat taggcgcgga tgacgcccaa gtggatgcat tgatcgatga actgactgca    660

gcgggcctgc cgatcccgcc acaggtcaat cgcagcaact ggcgaggcta tgccgaagca    720

ctgcgcgaca aacccgatat cgacctcgac gatgtcggcg gcgatacggc gaaacccatt    780

caggaaacca cttatcttcc cagctatggt cgaggcatgc ccgcacggat gccgaatggc    840

aactgctatg agttcaccgc cggtggtcag ccgggaagtc cctttcgggc tccgccaagc    900

agttgctgct tgaccggcga cacggaagtc ctctcggggg caggggttcc ggtgccgctg    960

aatcaggtaa aaccgggcga taccgtgatg acgcgtgacg gtgcggctgt cgtggctttt   1020

gtcgctcgac ctcaactcgg cgaacggaaa ctctatcgga tcaacggcgg tggccccgtg   1080
```

```
tttaccgata cgcatccttt cctgaatgcg tccgcgtccg attcccgtgc aacggccccc   1140

gcgattcttg ccgccgatcc gtcacatctg gcctggatgg taccgacact gagcgaagac   1200

ggcataggaa aactgaccac gggatgtgtg ctgaccggcc gtcgccccga gtcaagcgag   1260

tcgtttccgg tggacgtgac cacggtagag ccggtgcctc ggggaactgg cgacgactac   1320

ttgtacgacc tgaatcttct tgtcacgaca ggcgccagac aggaattctg ggccggcaag   1380

gacggccggt tctatctcgt gtcgccggaa ttccccgtgc tggctcaggc gggcgcggct   1440

gccgtcgcgg tggttgccgc gctagagggg ctgattgctg cgggcggccc gacgctctcc   1500

ggttggccgg tgacaacgcg ggaactcgtg catcgatttg gcgcggcgat tttcgatgcc   1560

gggctcgacg cagcacttcg cacggtgccc tcgtttggct cgccgacgcc cgtgcggcca   1620

ctattcgagc ggatcgacaa gctgtatcgg gatctcggtt cggtcgacgt cgtcggcgcc   1680

agtgcgatcg cggcattctt cgacggattc atgtccacca tcgtcacgtg gctgacggca   1740

tcggtggcat tgggctggag aaaaccggcc gagccctccg gcgagatcgt cgtggtcacg   1800

atattcgata tggcgctggc gcccggcacg cctgtccaga ccgccagcca aatccggatg   1860

gaagttcgcg cgcaaggaca gagcgaatcc gcatccacga cgatgtggaa ccgcagcggc   1920

agggcgaaca cccgttttca tcactatttc gatcagttga ttcacctcga cagagccaaa   1980

ctgggcgcga cgggcggcct gactttcgcg gtcgtgatgg atggcgcctc cgttccggcg   2040

ttgtcaggtg cggctcccct cgtcatcggc gatcgagccc attgcttcca gtcggcacag   2100

cttttcgacg cggccggaac ggccgtcggc acgatccgat tcgatactcg cttgcttacg   2160

cggcggacgg ccgaggacga attggcacac agcggtcttt ggacagagga ggcagccctg   2220

gcatattcca acgcgctcgg gacagcaatg gtcgcgccga tactcacgac gctcgaaggc   2280

ttggccggca gatga                                                   2295
```

<210> SEQ ID NO 29
<211> LENGTH: 1023
<212> TYPE: DNA
<213> ORGANISM: Burkholderia sp.

<400> SEQUENCE: 29

```
atgatgaaaa acctacccgc cgttgaattg ccggaacttt tcgcaaaatt tcgtccggga     60

gagaggcgag atatcgtttc gcatttcacg ccgactattg cacagcaggc tggaatcact    120

ccccacttga gtgagccgat tccggtcgag ttgatcgatg cgacaacgcc ttatttgctg    180

gtcgatgaat caaatcgaat tcttctcgcg aatgatcgtg gcgtgggtgc ctggcaatgg    240

gcattcgtcg gaagctattc cgattacgca tcgtatgttc tggggacttc atttggtagc    300

gatccagccc tcaatccggc tccgctctat cttggtccgc ctcagaacac caagtatctc    360

cagtcgaacg gatcatcgag tagctgggac tgggtgtttt gggccgactc atcttacaaa    420

tatccgaccg tatcgttgaa gactcaggcg atatcttcgc aaaccttcaa gctcatttat    480

aaaaacaact ccacggaaat ggggttgtgc gccgattcgg ggtcgtggaa ctgggtgtat    540

gttggaaata caagcagcta caccccattg acactgacag caaggaaatt cttccttggt    600

tacaatgatt tgaagaaatt atttgcagca acctggccta acgcaagcat cacggattgg    660

tctttccgag ttggcgacaa ggactatgaa ttgcttcatc aatcgaaagc gcagcagatt    720

tacaacgact ccgggcttag caagtacaaa tgggtagaag aggtatttga ctgcgacgat    780

tttagctacg cttataaagc gcaggcatca agagttgcat atgaggatta caaggctacg    840
```

ggaaacgcag tgcaaagatc ctatgcgtct ggcgttgtgt tcgggcgcaa gccggatggc 900
actgctcacg cggttaacgt gtttgtcgac tacacttgca ccgtaaagat actggaacca 960
caaaatggtt caatcataga cggcaaggat tgggcctata cgccgtactt cattctgttt 1020
tga 1023

<210> SEQ ID NO 30
<211> LENGTH: 363
<212> TYPE: DNA
<213> ORGANISM: Burkholderia ambifaria

<400> SEQUENCE: 30
atgtccgcgc gaagcacagt cgtgaagttg caaaacaact caggtaatac gttatttctc 60
gatccggcat cgatcaatct gattcatggt gaatgggtaa catatcctcc ggagaaaata 120
ccggatggtc aaactggcca atgggagagc gattcggatg gttttatgac gggaacggaa 180
ggccagcttc agtatcaatt tgctgacggg ggtggtatcg agaatgtgag actttattgg 240
gataaccctt atattggaaa caacggctac tcgataaccg ttagtgccgg gggttataag 300
gtcggttatg acggtggctc cggggataac gcgactgtta acttctacat caaacagggc 360
tga 363

<210> SEQ ID NO 31
<211> LENGTH: 363
<212> TYPE: DNA
<213> ORGANISM: Burkholderia pyrrocinia

<400> SEQUENCE: 31
atgtctgcgc gaagcactgt cgtgaagttg caaaacaatt cggggaacac gttattcctg 60
gatcccgcgt cgatcaacct gctgcacggg gaatgggtga catatcctcc ggagaaaatc 120
ccagatggcc agactggcca atgggaaagc gattcggacg gttttatgac gggaacggaa 180
ggtcagcttc aatatcaatt tgcagacggc ggcggtatcg agaacgtcag gctttactgg 240
gacaacccct atgtcggaaa taacggatac tcgatcaccg ttagtgccgc gggttataag 300
gttggttatg acggtggctc cggggataac gcaaccgtca acttctacat caagaagggc 360
tga 363

<210> SEQ ID NO 32
<211> LENGTH: 363
<212> TYPE: DNA
<213> ORGANISM: Burkholderia glumae

<400> SEQUENCE: 32
atgtcttcac gaagcactgt cgtgaaactg caaaacaatt cgggacacac actttatctg 60
gactcgacgt cgatccagct agcgcacggc gagtgggtaa cgtatccccc ggaaaaaatt 120
ccgaatggtc agaccggcca gtggcagacc gattcagacg gtttcatgac cggaaccgaa 180
ggaaagcttc aatatcaatt tgccgacaac gatggcatcg agaacgttcg gatctactgg 240
gacaatccgt acatcggcaa caacggctat tcgattaccg tcagcgcggc gggttacaag 300
gttggctacg atggcggctc cggtgataac gcgaccgtcg atttctacat caagcaggaa 360
taa 363

<210> SEQ ID NO 33
<211> LENGTH: 363
<212> TYPE: DNA
<213> ORGANISM: Burkholderia anthina -continued

<400> SEQUENCE: 33
atgtccgcac gaagcactgt tgtgaagctg caaaacaact cgggcagcac gttgtttctg 60
gactcggcat cgatcaatct gctgcatggc gaatgggtca cgtacccgcc ggagaagatc 120
ccgaatggac aaacgggggga atgggagagc gattccgacg gcttcatgac cggaaccgag 180
gggaagcttc aatatcaatt tgccgacggt ggcggtatcg aaaacttgcg gatctactgg 240
gacaacccgt attacggcgg aaacggatac tcgataaccg tgagcgctgc cggttacaaa 300
gtcggttacg acggaggctc aggagacaat gcgacggtca ctttctacat caagcaggcc 360
tga 363

<210> SEQ ID NO 34
<211> LENGTH: 363
<212> TYPE: DNA
<213> ORGANISM: Burkholderia anthina

<400> SEQUENCE: 34
atgtccgcac gaagcactgt tgtgaagctg caaaacaact cgggcagcac gttgtttctg 60
gactcggcat cgatcaatct gctgcatggc gaatgggtca cgtacccgcc ggagaagatc 120
ccgaatggac aaatggggga atgggagagc gattccgacg gcttcacgac cggaaccgag 180
gggaagcttc aatatcaatt tgccgacggt ggcggtatcg aaaacttgcg gatctactgg 240
gacaacccgt attacggcgg aaacggatac tcgataaccg tgagcgctgc cggttacaaa 300
gtcggttacg acggaggctc aggagacaat gcgacggtca ctttctacat caagcaggct 360
tga 363

<210> SEQ ID NO 35
<211> LENGTH: 369
<212> TYPE: DNA
<213> ORGANISM: Burkholderia multivorans

<400> SEQUENCE: 35
atgtctgctc gcagcgtcgc ggttaccttc ttcaatctca cctcgcatga tttaatcctc 60
gacacatctt cggtccagct ccagcacgga gaatggaaga gatatccacc ttcaatcatc 120
ccgtcgcttc aatacgggga atgggagagc gactcggacg gcatttacac cggcacacaa 180
ggcagcctcc aatatcaatt ccaatacaat ggaattcaga acattccaat ttcatgggat 240
gatccgtact acggaggaaa ttcatatgga atttcatgta gctcgtccga ttttaaaacg 300
cgatacgccg gaggggatgg agacaatgcc gtggtgcaat tttcatcga tcaaaaggga 360 tcggactag 369

<210> SEQ ID NO 36
<211> LENGTH: 372
<212> TYPE: DNA
<213> ORGANISM: Sinorhizobium medicae

<400> SEQUENCE: 36
attgagcgca gcgcacggag cgttgttatc cagctgaaca atcagaccag tgcgatcctg 60
cagttgcagc aagacacctt aagtcttgag cacggtgaat gggttatcta tccgccagcg 120
aacatatatc caggtcagct agtgtcctgg caaacagact caaacggttt catgactgga 180
acggaggggc gctgcaccta tcaattcatt gccggctcaa ctattgcgaa cgtgaagctg 240
cattgggaca acccatatgt gggtggcaac agttatagca ttgttgtcac gccaccgccc 300
tatagcggag actatggggg cggaagtgga gacaactcga cggtcaccta taaggtgtac 360
cgggtagctt ga 372

<210> SEQ ID NO 37
<211> LENGTH: 360
<212> TYPE: DNA
<213> ORGANISM: Burkholderia ambifaria

<400> SEQUENCE: 37
atggcagcgc gtagcgtagt tgcgaaattc tccaacaaca cgaagttcga tttgatgttg 60
ggggactccg aactgtggca cggacattgg gtgacttcgc cccctagctc cattgcaccg 120
ggcgcggagg gccaatggga aaccgattct gatgattatg aaagtgggac cgcaggagat 180
cttcagtatc aattcaccaa tgaggaagga actcagacgg tgagagtttc ttgggcggtt 240
ccttacttgg gatcgaataa ttttgaagtt tactgtgaag cggctggcgt tcgacctgga 300
tacaccgggg gcggtcagga caccaacgcg acggtgaatt attaccttaa tcaggcctag 360

<210> SEQ ID NO 38
<211> LENGTH: 366
<212> TYPE: DNA
<213> ORGANISM: Burkholderia cenocepacia

<400> SEQUENCE: 38
atggctgatg ctgcacgtag cgtaattgcg aagctgacca acaatacgaa atttgtattg 60
actctagata aatcatcggt tcagttggac cacggtaagt gggcaacctc acctccccgac 120 cagatctcgc ctggtgatgt tgggcaatgg gagagcgaat ccgatagctt taacacaggc 180
acggagggcc gtcttcggta tcaattctcc gatcaatcaa cgtataacgt cgatgtctat 240
tggagtgatc catttttag tggcagtgat tattcgattg attgcaatgc agatggattt 300
agggtcggcc acaccggggg tgatgggtct aacgcgactg ttgattacta cattaatgag 360
ggctga 366

<210> SEQ ID NO 39
<211> LENGTH: 399
<212> TYPE: DNA
<213> ORGANISM: Pseudomonas syringae

<400> SEQUENCE: 39
atgtctgacg ccgcaagaag cacagtcata aaagtcacaa acaactcaaa gtacaactta 60
cggttaatta cctcctcgca gaaactcccc cacggcgaat ggataactta tccaccagat 120
cgcataacta aaaactcaac atccaacggc cctgggcatg caagctggga aaccgactcc 180
gatggattca tgacaggaac agagggggaa tgctcctatt cattcacaga tgatgatgag 240
atctacgata taaacatcaa atgggataac cccttctctg gcggaaacac atactcaata 300
catccagaca acgacttagt aagatgcaca tacaccgcag ataaaggtaa taacgcgacc 360
gtaactttta cgatagaaaa tggctcaaat cataactag 399

<210> SEQ ID NO 40
<211> LENGTH: 384
<212> TYPE: DNA
<213> ORGANISM: Pseudomonas lini

<400> SEQUENCE: 40
atggctaaaa gaagcgttga tgtttatttt gaaaactacc tcgactccac cttgagtcta 60
actcaaaatt ctctgaagtt agatcatggg gaatgggata cttatcctcc gcagaagata 120

-continued

```
ttgaagccga gctctaatgt gtccggcaaa ggctattgga agacagagtc ggacgggttc    180

gctacgggca cggaggcact ttgctcctac gctttttatg attttgtcac tgaggaaatt    240

tgcaatataa atatccactg ggacgaccca tacgtggggt ctaattcgta tgaaatcacg    300

accgatagcg ataacgttaa agtttcatat agtggtggag acggcgataa cgctactgtg    360

accttcaggg cagaaaaaag ataa                                           384
```

<210> SEQ ID NO 41
<211> LENGTH: 405
<212> TYPE: DNA
<213> ORGANISM: Aquimarina muelleri

<400> SEQUENCE: 41

```
atgtcagcac gcagtacaac agtaaaattg cagaacacaa catctgatct aatcaaactt     60

accgatgctt ctctatctca tggagtatgg tcttctaacc agtatccgcc aagtactatt    120

tcagcaaata gtgacggtag ctggatgtca gagtctgatg gatttatgac aggtaccgag    180

ggtacagtaa cgtatcaatt acctaatggt attggtagta ttgtaataac ttgggataac    240

ccatatgtag gtagtaactc gtatagtatg aaagctcctg ctggatttga aattaataaa    300

agcggtggta gcggggataa tgctgtagta actttacac tttcagttag taaagtaaaa    360

caaactaaat catttgaaga ggcagtaggt gcatttgcta attaa                    405
```

<210> SEQ ID NO 42
<211> LENGTH: 357
<212> TYPE: DNA
<213> ORGANISM: Nocardia gamkensis

<400> SEQUENCE: 42

```
atggcggcac gatcgtactg ggtacgcgta tacaactaca ccgggaccga cctcactttg     60

acgaataagg cactgcagca cggagtctgg agcaacaacg gcggagccac cccacccgac    120

gtcatccctg aaggtcggcg agcggaatgg gggagcgagt ccgatggact cgccaccggc    180

accgaaggcg aggtcgtcta cgcctccgcc gcaggggaat tcaaggttta ctgggacaac    240

ccttacgtag gctccgacca gacctccgtg cgtacgccga cgcggttctc ctccgtcaag    300

gaggacagtc gcggagacaa cgccaccctc aaggtagcgc tcgtgcagga ggaatga       357
```

<210> SEQ ID NO 43
<211> LENGTH: 252
<212> TYPE: PRT
<213> ORGANISM: Pseudomonas chlororaphis

<400> SEQUENCE: 43

```
Met Ala Val Ile Lys Gly Phe Val Gly Val Cys Val Gly Ala Leu Phe
1               5                   10                  15

Ile Phe Ala Gly Ser Ala Tyr Ala Gly Val Thr Val Gln Gln Ala Ile
            20                  25                  30

Arg Glu Gly Cys Tyr Thr Ser Ala Gln Ala Lys Glu Ile Ile Ala Gln
        35                  40                  45

Gly Glu Arg Ser Thr Pro Met Gly Thr Val Thr Leu Glu Lys Ala Lys
    50                  55                  60

Leu Tyr Leu Glu Arg Val Asn Asp Arg Ser Val Thr Arg Thr Lys Val
65                  70                  75                  80

Thr Ala Pro Glu Thr Trp Val Tyr Arg Gly Tyr Asp Asp Ala Ser Asn
                85                  90                  95
```

-continued

```
Trp His Thr Glu Glu Leu Leu Asp Gly Val Ile Tyr Ser Lys Gly Gln
            100                 105                 110

Asn Ala Arg Asp Lys Ala Ile Arg Arg Gly Ile Ser Glu Lys Ser Phe
        115                 120                 125

Trp Gly Lys Asn Gly Pro Gln Leu Arg His Glu Ala Ser Ser Val Gly
    130                 135                 140

Ser Phe Pro Gly Glu Pro Thr Tyr Phe Met Met Arg Leu Leu Ala Ile
145                 150                 155                 160

Gln Thr Ser Asp Thr Pro Pro Ser Gln Phe Val Ser Phe Ala Leu Asn
                165                 170                 175

Tyr Lys Leu Ala Ser Glu Phe Gly Glu Val Val Tyr Ala Leu Gln Val
            180                 185                 190

Asn Pro Asp Ser Pro Val Leu Gly Leu Gln Asn Cys Asn Leu Lys Gly
        195                 200                 205

Glu Tyr Gln Val Gln Ile Leu Gly Gly Thr Thr Phe Gly Val Leu Tyr
    210                 215                 220

Lys Lys Lys Arg Gly Gln Asn Trp Glu Arg Tyr Asp Arg Ser Asn Arg
225                 230                 235                 240

Val Trp Gly Pro Val Ala Ser Gly Thr Val Pro Glu
                245                 250


<210> SEQ ID NO 44
<211> LENGTH: 269
<212> TYPE: PRT
<213> ORGANISM: Pseudomonas chlororaphis

<400> SEQUENCE: 44

Met Lys Ala Ile Leu Leu Ser Arg Lys Pro Val Gly Val Asn Glu Asp
1               5                   10                  15

Val Ser Tyr Phe Ser Glu Lys His Val Met Phe Tyr Gly Ala Gln Asn
            20                  25                  30

Lys Thr Ser Gly Leu Pro Val Arg Leu Val Asp Asp Thr Pro Pro Val
        35                  40                  45

Val Ser Glu Arg Asp His Pro Ser Leu Pro Gly Ile Ile Gln Ser Lys
    50                  55                  60

Ile Lys Arg Gly Thr Asp Cys Val Val Arg Gln Ile Asn Pro Val Phe
65                  70                  75                  80

Tyr Leu Arg Glu Gly Glu Leu Leu Val Ser Asp Ser Phe Ser Tyr Leu
                85                  90                  95

Ser Lys Ala Tyr Leu Glu Tyr Ala Glu Asp Thr Val Val Leu Thr Arg
            100                 105                 110

Lys Thr Asn Met Gly Glu Phe Tyr Phe Val Phe Pro Asp Ile Lys Ala
        115                 120                 125

Lys Arg Leu Tyr Asp Asp Ala Thr Gly Val Thr Leu Val Asp Ile Val
    130                 135                 140

Asp Gly Gly Arg Ser Leu Tyr Pro Ile Pro Pro Lys Ala Ser Leu Ser
145                 150                 155                 160

Thr Ser Glu Ser Val Val Leu Asp Ser Ser Leu Tyr Met Leu Thr Glu
                165                 170                 175

Val Lys Pro Thr Ser Gly Thr Thr Ile Tyr Leu Gly Trp Ser Val Pro
            180                 185                 190

Asp Ala Thr Lys Ser Asp Val Trp Trp Gly Leu Tyr Arg Gly Val Met
        195                 200                 205

Pro Asp Trp Ser Gly Leu Asp Ser Tyr Thr Asn Trp Asp Trp Leu Phe
    210                 215                 220
```

Pro Lys Gly Thr Thr Asn Thr Ala Ile Gly Ser Glu Thr Ile Thr Val
225 230 235 240

Ser Arg Met Ser Ser Gly Ala Ile Tyr Thr Leu Ala Leu Phe Ser Ser
245 250 255

Gly Trp Asn Leu Thr Asp Tyr Gln Thr Phe Asn Ala Pro
260 265

<210> SEQ ID NO 45
<211> LENGTH: 295
<212> TYPE: PRT
<213> ORGANISM: Enterobacter cloacae

<400> SEQUENCE: 45

Met Ala Thr Thr Gln Asn Gln Asp Leu Leu Ser Lys Phe His Asp Trp
1 5 10 15

Val Asp Asn Lys Ser Ala Ala Pro Leu His Gly Pro Leu Leu Lys Ala
20 25 30

His Ala Leu Phe Lys Val Glu Lys Ser Gly Asp Ser Ser Val Ser Gly
35 40 45

Gln Asn Thr Ile Ala Thr Gly Asp Gln Ala Pro His Gln Ser Asp Val
50 55 60

Gly Lys Ile Leu Asp Leu Ala Ile Lys Asn Gln Glu Lys Asp Lys Ile
65 70 75 80

Ile Asp Ile Leu Ala Ser Asn Pro Gly Asn Ala Val Thr Ser Ile Leu
85 90 95

Gly Leu Ala Lys Thr Arg Thr Thr Trp Asn Pro Leu Asp Pro Asp Asn
100 105 110

Asn Lys Asn Ala Gln Gly Phe Met Asp Phe Val Glu Gln Ile Leu Arg
115 120 125

Val Pro Tyr Phe Arg Ile Thr Gln Ser Glu His Pro Thr Val Asn Tyr
130 135 140

Glu Glu Glu Asn Tyr Asp Ser Leu Ile Asn Lys Val Ala Asp Leu Tyr
145 150 155 160

Ala Gly Ile Thr Glu Ala Ser Lys Glu Lys Val Lys Asn Ser Ile Val
165 170 175

Asn Leu Ala Met Ala Cys Thr Ser Arg Val Asn Thr Lys Asn Thr Asp
180 185 190

Thr Leu Phe Val Gln Asn Ser Ile Gln Ser Ala Asn Asp Asp Ile Val
195 200 205

Val Gln Leu Glu Gln Thr Tyr Met Leu Met Glu Arg Ser His Ser Ser
210 215 220

Gly Lys Gly Ala Pro Lys Asp Lys Tyr Lys Thr Gln Val Asp Val Lys
225 230 235 240

Val Leu Glu Leu Thr Phe Ser Ser Ser Leu Trp Thr Arg Asp Ala Ala
245 250 255

Val Lys Leu Ala Ala Lys Phe Val Lys Ser Trp Asp Asp Trp Leu Asp
260 265 270

Glu Asn Thr Thr Pro Asp Thr Ser Lys His Val Lys Phe Cys Phe Gly
275 280 285

Lys Glu Gly Ala Ala Val Glu
290 295

<210> SEQ ID NO 46
<211> LENGTH: 283
<212> TYPE: PRT

<213> ORGANISM: Desulfovibrio zosterae

<400> SEQUENCE: 46

Met Thr Val Gln Ala Lys Phe Asp Gln Trp Leu Glu Asn Pro Gln Leu
1 5 10 15

Ile Thr Met Glu Lys Gly Leu Thr Asp Ala Ala Phe Met Phe Tyr Ile
20 25 30

Pro Glu Ser Gly Asp Ser Asn Val Ser Gly Gln Asn Ser Thr Ala Thr
35 40 45

Gly Ser Asn Ala Gln Lys Glu Ser Ala Gln Gly Lys Glu Leu Asp Glu
50 55 60

Ala Ile Gly Lys Gly Asp Glu Glu Ala Ile Val Arg Leu Leu Thr Asn
65 70 75 80

Ser Thr Gly Asn Ala Val Ser Ser Ile Leu Gly Leu Ala Gln Ser Arg
85 90 95

Thr Asp Trp Asn Pro Leu Asp Pro Asn Asn Asp Lys Asn Ala Glu Gly
100 105 110

Phe Gln Asn Phe Ile Lys Ser Ile Leu Lys Val Pro Phe Phe Asn Val
115 120 125

Thr Gln Ser Glu Arg Thr Thr Val His Tyr Glu Glu Thr Asn Tyr Asn
130 135 140

Asp Leu Ile Asp Lys Val Val Asp Leu Tyr Asp Gly Ile Thr Lys Ser
145 150 155 160

Asp Ile Pro Leu Ile Lys Asn Ser Ile Val Asn Leu Ala Lys Ala Cys
165 170 175

Thr Ser Arg Val Asn Thr Lys Asn Thr Lys Thr Leu Phe Val Gln Asn
180 185 190

Thr Met Asn Ala Thr Gly Thr Asp Ile Val Val Gly Ile Gln Gln Thr
195 200 205

Phe Met Met Met Glu Arg Ser His Glu Ser His Lys Gly Ala Pro Lys
210 215 220

Asp Gln Tyr Lys Thr Glu Ile Thr Val Asn Val Met Glu Leu Thr Phe
225 230 235 240

Lys Gly Ser Ile Trp Asn Lys Asp Ala Ala Lys Lys Leu Ala Ala Lys
245 250 255

Phe Val Lys Ser Trp Asp Asp Trp Leu Asp Gly Thr Thr Thr Pro Pro
260 265 270

Glu Lys Lys Ala Ala Ala Ile Lys Tyr Cys Leu
275 280

<210> SEQ ID NO 47
<211> LENGTH: 219
<212> TYPE: PRT
<213> ORGANISM: Ralstonia sp. A12

<400> SEQUENCE: 47

Met Asp Leu Leu Thr Gln Ser Thr Ala Asn Ala Val Ser Ser Ile Leu
1 5 10 15

Gly Leu Ser Gln Thr Arg Ser Gly Trp Asn Pro Leu Asp Pro Thr Glu
20 25 30

Lys Glu Asn Ala Gln Gly Phe Gln Arg Phe Val Glu Gln Ile Leu Lys
35 40 45

Val Pro Tyr Phe Asn Thr Thr Gln Ala Glu Thr Lys Thr Val His Tyr
50 55 60

Gln Glu Ser Asn Tyr Asn Ser Leu Ile Asp Lys Val Val Asp Leu Tyr

```
65                  70                  75                  80

Asp Gly Val Thr Gln Gln Asp Lys Glu Lys Ile Lys Arg Ser Ile Val
                85                  90                  95

Asn Leu Ala Lys Ala Cys Thr Ser Arg Val Asn Gln Lys Asn Thr Gln
            100                 105                 110

Thr Leu Phe Val Gln Asn Thr Met His Ala Pro Gly Asn Ser Arg Asn
        115                 120                 125

Ile Val Val Gln Leu Ala Gln Thr Phe Met Met Met Glu Leu Asp His
    130                 135                 140

Arg Thr Gly Lys Gly Ala Pro Gln Asp Gln Phe Lys Thr Glu Ile Ser
145                 150                 155                 160

Val Arg Val Leu Glu Leu Thr Phe Gln Gly Asp Ile Trp Asp Arg Ser
                165                 170                 175

Ala Ala Glu Lys Leu Ala Ala Lys Phe Val Gln Ser Trp Asp Asp Trp
            180                 185                 190

Leu Asn Asp Ser Thr Thr Pro Pro Ser Pro Gln Gln Arg Lys Ile Ala
        195                 200                 205

Phe Cys Phe Ser Pro Arg Glu Ile Ala Ser Val
    210                 215
```

<210> SEQ ID NO 48
<211> LENGTH: 290
<212> TYPE: PRT
<213> ORGANISM: Pectobacterium carotovorum

<400> SEQUENCE: 48

```
Met Ser Asp Ile Lys His Asp Asn Ala Leu Ala Thr Phe Ser Ser Trp
1               5                   10                  15

Leu Asp Asp Asp Lys Asn Ile Lys Leu Ser Glu Ser Ser Ile Asn Thr
            20                  25                  30

His Gln Leu Phe Ala Leu Ser Ala Glu Gly Asp Ser Ser Val Ser Gly
        35                  40                  45

Gln Asn Ser Ile Ser Thr Gly Thr Leu Ala Ser Gln Glu Ser Ala Gln
    50                  55                  60

Gly Lys Ile Leu Asp Asn Ala Ile Ala Arg Gly Asp Lys Asp Glu Ile
65                  70                  75                  80

Thr Lys Val Leu Thr Ser Ser Thr Gly Asn Ala Val Ser Ser Ile Leu
                85                  90                  95

Gly Leu Ser Gln Ser Arg Ser Gly Trp Asn Pro Leu Asp Pro Asp Asn
            100                 105                 110

Asp Ser Asn Ser Lys Gly Phe Thr Arg Phe Val Glu Ser Leu Leu Lys
        115                 120                 125

Val Pro Tyr Phe Asn Thr Thr Gln Ser Glu Arg Thr Thr Val Asn Tyr
    130                 135                 140

Glu Glu Glu Asn Tyr Asp Ser Leu Ile Ser Lys Val Val Asp Leu Tyr
145                 150                 155                 160

Ser Gly Ile Glu Glu Lys Asp Lys Ser Lys Ile Lys Thr Ser Ile Val
                165                 170                 175

Asn Leu Ala Lys Ala Cys Thr Ser Arg Val Asn Thr Lys Asn Thr Lys
            180                 185                 190

Thr Leu Phe Val Gln Asn Thr Leu Asn Ala Ser Asn Lys Asn Ile Val
        195                 200                 205

Val Gln Leu Gln Gln Thr Phe Met Met Met Glu Arg Ser His Thr Ser
    210                 215                 220
```

-continued

```
Gly Lys Gly Ala Pro Lys Asp Lys Tyr Lys Thr Glu Ile Ile Val Gln
225                 230                 235                 240

Val Leu Glu Leu Thr Phe Gln Gly Asp Ile Trp Thr Lys Ser Ala Ala
                245                 250                 255

Glu Lys Leu Ala Glu Lys Phe Ala Lys Ser Trp Asp Asp Trp Leu Asn
            260                 265                 270

Asp Thr Thr Thr Pro Glu Ser Asp Asp Ala Lys Asn Ile Lys Phe Cys
        275                 280                 285

Phe Lys
    290


<210> SEQ ID NO 49
<211> LENGTH: 305
<212> TYPE: PRT
<213> ORGANISM: Salinivibrio sp.

<400> SEQUENCE: 49

Met Asn Ala Ser Asp Ala Gln Asn Leu Thr Ser Gln Phe Asp Thr Trp
1               5                   10                  15

Leu Asn Ser His Gln Ser Leu Val Ser Asn Gln Gln Gln Leu Gln His
            20                  25                  30

Ser Ala Leu Phe Ala Val Pro Arg Asp Gly Asp Ser Ser Val Ser Gly
        35                  40                  45

Gln Asn Thr Ile Gly Ala Gly Lys Asn Ala Gln Thr Glu Ser Ala Gln
    50                  55                  60

Gly Lys Lys Leu Asp Asp Ala Ile Ser Ala Gly Asn His Ser Glu Ile
65                  70                  75                  80

Val Arg Leu Leu Thr Glu Ser Thr Gly Asn Ala Val Ser Ser Ile Leu
                85                  90                  95

Gly Leu Ala Gln Ser Arg Thr Gly Trp Asn Pro Leu Asp Pro Asp Asn
            100                 105                 110

Asp Lys Asn Ala Glu Gly Phe Gln Glu Phe Val Ser Ser Ile Leu Lys
        115                 120                 125

Val Pro Phe Phe Asn Val Thr Gln Ser Glu Arg Thr Thr Val His Tyr
    130                 135                 140

Glu Glu Glu Asn Tyr Asn Ser Leu Ile Asp Lys Val Val Gly Leu Tyr
145                 150                 155                 160

Asp Gly Ile Thr Glu Gln Asp Val Pro Leu Ile Lys Asn Ser Ile Val
                165                 170                 175

Asn Leu Ala Lys Ala Cys Thr Ser Arg Val Asn Thr Gln Asn Thr Lys
            180                 185                 190

Thr Leu Phe Val Gln Asn Thr Met Asn Ala Thr Gly Thr Asp Ile Val
        195                 200                 205

Val Gly Ile Gln Gln Thr Phe Met Met Met Glu Arg Ser His Ser Ser
    210                 215                 220

Gly Lys Gly Ala Pro Lys Asp Gln Tyr Lys Thr Glu Ile Thr Val Asn
225                 230                 235                 240

Val Met Glu Leu Thr Phe Lys Gly Gly Leu Trp Asn Glu Ser Ala Ala
                245                 250                 255

Glu Lys Leu Ala Asp Lys Phe Val Lys Ser Trp Asp Asp Trp Leu Asp
            260                 265                 270

Gly Thr Thr Thr Pro Ala Ser Pro Ser Ala Asp Gln Ile Gln Phe Cys
        275                 280                 285

Phe Gly Pro Ala His Arg Ala Arg Gln Lys Gln Glu Ala Asp Ala Ile
    290                 295                 300
```

Lys
305

<210> SEQ ID NO 50
<211> LENGTH: 276
<212> TYPE: PRT
<213> ORGANISM: Klebsiella quasipneumoniae

<400> SEQUENCE: 50

Met Glu Ser Asn Glu Ile Met Cys Asn Val Glu Arg Trp Leu Asp Asn
1 5 10 15

Gln Ala Val Asn Ser Ile Gly Ile Cys Leu Asp Gly Leu Asn Thr Thr
20 25 30

Gly Asn Thr His Ile Ser Gly Gly Ser Ser Val Leu Thr Gly Ser Ala
35 40 45

Ala Thr Gln Glu Arg Glu Ile Gly Lys Glu Leu Ser Leu Ile Thr Asp
50 55 60

Ile Asp Glu Leu Ala Glu Lys Leu Val Ser Ser Pro Ala Asn Phe Val
65 70 75 80

Thr Thr Val Met Gly Ile Ala Gln Ser Arg Ser Gly Trp Lys Pro Leu
85 90 95

Glu Pro Glu Ser Ala Asp Asn Ala Glu Asn Phe Lys Lys Tyr Ile Asp
100 105 110

Gln Ile Met Lys Phe Pro Leu Met Ile Val Thr Lys Thr Asp Thr Thr
115 120 125

Thr Val Thr Tyr Ser Glu Gly Asn Tyr Asp Ser Leu Ile Asp Asn Ile
130 135 140

Ala Asp Ile Tyr Ser Gly Met Ser Asp Gly Asp Lys Asn Ser Val Lys
145 150 155 160

Ala Gly Leu Thr Ser Leu Ala Lys Ser Cys Met Ser Arg Val Asn Glu
165 170 175

Lys Gln Lys Lys Val Leu Phe Thr Gln Ser Thr Met Cys Val Asn Asp
180 185 190

Glu Val Thr Thr Ser Phe Tyr Ser Ser Asn Val Ala Met Glu Lys Lys
195 200 205

His Ser Ser Gly Lys Asn Ala Pro Ala Asp Glu Phe Ser Ser Glu Val
210 215 220

Gln Val Ser Arg Val Glu Val Lys Phe Asn Arg Met Ala Leu Asn Lys
225 230 235 240

Asn Ile Ala Lys Lys Leu Cys Ser Leu Leu Phe Lys Ser Ile Asp Asp
245 250 255

Trp Leu Glu Glu Thr Asn Thr Lys Gln Thr Asp Lys Lys Ile Glu Phe
260 265 270

Cys Phe Gly Asp
275

<210> SEQ ID NO 51
<211> LENGTH: 294
<212> TYPE: PRT
<213> ORGANISM: Pseudomonas entomophila

<400> SEQUENCE: 51

Met Ile Asp Ile Asp Thr Ile Thr Asn Thr Trp Gly Arg Trp Lys Thr
1 5 10 15

Ala Gln Tyr Gly Thr Thr Cys Trp Phe Thr Glu Ser Thr Gln Tyr Ala
20 25 30

```
Arg Asn Lys Asp Thr Arg Gly Tyr Met Gln Tyr Gln Thr Asn Val Ser
        35                  40                  45

Ala Pro Lys Asp Leu Val Tyr Ser Ser Tyr Ala Gln Ser Asp Gly Gly
    50                  55                  60

Ser Ala Leu Leu Gly Lys Tyr Asp Thr Ile Asn Asp Gly Gly Gln Val
65                  70                  75                  80

Ile Glu His Thr Val Ser Leu Gln Gln Gly Leu Ser Asp Thr Phe Thr
                85                  90                  95

Trp Ser Val Thr Glu Gln Leu Lys Ile Gly Val Ser Val Lys Ala Asn
            100                 105                 110

Ala Gly Ile Pro Leu Ile Gly Gly Ala Glu Thr Thr Ser Thr Val Glu
        115                 120                 125

Met Asp Leu Ser Ser Thr Gln Gly Ala Ser Thr Thr Lys Ser Ser Asn
    130                 135                 140

Tyr Gly Ala Ser Thr Thr Val Pro Ile Ser Pro His Thr His Gly Trp
145                 150                 155                 160

Gly Glu Val Asp Leu Ser Phe Thr Glu Leu Arg Thr Gln Trp Val Gly
                165                 170                 175

Asn Ala Ser Met Val Gly Cys Val Ala Ile Trp Phe Asn Asn Lys Val
            180                 185                 190

Ala Leu Asn Asn Asn Gly Asp Tyr His Tyr Leu Trp Phe Ile Pro Ile
        195                 200                 205

Gln Gln Val Phe Ser Glu Ile Ile Gln His Asn Ile Ile Ser Thr Ser
    210                 215                 220

Gly Tyr Val Val Gln Gly Gly Gly Val Leu Ala Gln Ala Thr Gly Thr
225                 230                 235                 240

Phe His Ser Ser Met Gly Leu Ser Leu Lys Thr Ile Ser His Glu Gln
                245                 250                 255

Pro Tyr Pro Gly Asp Asn Lys Ala Val Arg Thr Ser Phe Gly Tyr Arg
            260                 265                 270

Arg Leu Asp Lys Pro Leu Glu Ser Val Val Phe Pro Ala Glu His Asp
        275                 280                 285

Leu Asn Gly Arg Ser Arg
    290


<210> SEQ ID NO 52
<211> LENGTH: 286
<212> TYPE: PRT
<213> ORGANISM: Pseudomonas aeruginosa

<400> SEQUENCE: 52

Met Asn Asp Ile Asp Thr Ile Thr Asn Ala Trp Gly Arg Trp Lys Thr
1               5                   10                  15

Ala Gln Tyr Gly Thr Thr Cys Trp Phe Thr Glu Ser Thr Gln Tyr Gly
            20                  25                  30

Arg Asn Lys Asp Thr Arg Gly Tyr Met Gln Tyr Gln Thr Asn Val Ser
        35                  40                  45

Ala Pro Lys Asp Leu Val Tyr Ser Asn Phe Val Gln Gln Asp Gly Gly
    50                  55                  60

Ser Ala Leu Leu Gly Gln Tyr Asp Thr Ile Asn Asp Gly Ser Gln Val
65                  70                  75                  80

Ile Glu His Val Val Asn Leu Gln Gln Gly Leu Val Asp Thr Phe Thr
                85                  90                  95

Trp Ser Val Thr Glu Gln Leu Lys Val Gly Val Glu Val Lys Val Lys
```

```
            100                 105                 110

Ala Gly Ile Pro Leu Val Gly Gly Ala Glu Thr Thr Ser Thr Val Glu
        115                 120                 125

Val Ser Leu Ser Ser Thr Gln Gly Ala Ser Thr Ser Lys Ser Ser Asn
    130                 135                 140

Tyr Gly Ala Ser Thr Lys Val Pro Ile Ser Pro His Ser His Gly Trp
145                 150                 155                 160

Gly Glu Val Asp Leu Ser Phe Thr Glu Leu Arg Thr Gln Trp Val Gly
                165                 170                 175

Asn Val Gly Leu Gln Gly Cys Val Ala Ile Trp Phe Asn Asn Lys Val
            180                 185                 190

Ala Leu Asn Asn Asp Gly Asp Tyr His Tyr Leu Trp Phe Ile Pro Val
        195                 200                 205

Glu Gln Val Phe Trp Glu Cys Ile Gln His Asn Ile Val Asn Thr Ser
    210                 215                 220

Gly Tyr Val Val Gln Gly Asn Gly Val Leu Ala Gln Ala Thr Gly Thr
225                 230                 235                 240

Phe His Ser Ser Met Gly Leu Asn Leu Lys Thr Ile Ala His Glu Arg
                245                 250                 255

Pro Tyr Pro Glu Thr Ser Glu Ala Val Arg Thr Phe Tyr Asn Tyr Ala
            260                 265                 270

Ser Leu Val Pro Asp Leu Glu Thr Arg Val Arg Ser Ala Glu
        275                 280                 285


<210> SEQ ID NO 53
<211> LENGTH: 286
<212> TYPE: PRT
<213> ORGANISM: Pseudomonas phage

<400> SEQUENCE: 53

Met Asn Asp Ile Asp Thr Ile Thr Asn Ala Trp Gly Arg Trp Lys Thr
1               5                   10                  15

Ala Gln Tyr Gly Thr Thr Cys Trp Phe Thr Glu Ser Thr Gln Tyr Gly
            20                  25                  30

Arg Asn Lys Asp Thr Arg Ser Tyr Met Gln His Gln Thr Asn Val Ser
        35                  40                  45

Ala Pro Lys Asp Leu Val Tyr Ser Asn Phe Val Gln Gln Asp Gly Gly
    50                  55                  60

Ser Thr Leu Leu Gly Gln Tyr Asp Met Ile Asn Glu Gly Ser Gln Val
65                  70                  75                  80

Ile Glu Leu Ala Val Asn Leu Gln Gln Gly Leu Val Asp Thr Phe Thr
                85                  90                  95

Trp Ser Val Thr Glu Gln Leu Lys Val Gly Val Glu Val Lys Val Lys
            100                 105                 110

Ala Asn Ile Pro Leu Val Gly Gly Ala Glu Ile Thr Ser Thr Val Glu
        115                 120                 125

Leu Ser Leu Ser Ser Thr Gln Gly Ala Ser Thr Ser Lys Ser Ser Asn
    130                 135                 140

Tyr Gly Ala Ser Thr Lys Val Leu Ile Ser Pro His Ser His Gly Trp
145                 150                 155                 160

Gly Glu Val Ala Leu Ser Phe Thr Glu Leu Arg Thr Gln Trp Val Gly
                165                 170                 175

Asn Val Gly Leu Gln Gly Tyr Val Ala Ile Trp Phe Asn Asn Lys Val
            180                 185                 190
```

```
Ala Leu Asn Asn Asp Gly Asp Tyr His Tyr Leu Trp Phe Ile Pro Val
        195                 200                 205

Glu Gln Val Phe Trp Glu Cys Val Gln His Asn Ile Val Asn Thr Ser
    210                 215                 220

Gly Tyr Val Val Gln Gly Asn Gly Val Leu Ala Gln Ala Thr Gly Thr
225                 230                 235                 240

Phe His Ser Ser Val Gly Leu Asn Leu Lys Thr Ile Ala His Glu Arg
                245                 250                 255

Pro Tyr Pro Glu Thr Ser Glu Ala Val Arg Thr Phe Tyr Asn Tyr Ala
            260                 265                 270

Ser Leu Val Pro Asp Leu Glu Thr Arg Val Arg Ser Ala Glu
        275                 280                 285


<210> SEQ ID NO 54
<211> LENGTH: 286
<212> TYPE: PRT
<213> ORGANISM: Pseudomonas aeruginosa

<400> SEQUENCE: 54

Met Asn Asp Ile Asp Thr Ile Thr Asn Ala Trp Gly Arg Trp Lys Thr
1               5                   10                  15

Ala Gln Tyr Gly Thr Thr Cys Trp Phe Thr Glu Ser Thr Gln Tyr Gly
            20                  25                  30

Arg Asn Lys Asp Thr Arg Ser Tyr Met Gln His Gln Thr Asn Val Ser
        35                  40                  45

Ala Pro Lys Asp Leu Val Tyr Ser Asn Phe Val Gln Gln Asp Gly Gly
    50                  55                  60

Ser Thr Leu Leu Gly Gln Tyr Asp Met Ile Asn Glu Gly Ser Gln Val
65                  70                  75                  80

Ile Glu Leu Ala Val Asn Leu Gln Gln Gly Leu Val Asp Thr Phe Thr
                85                  90                  95

Trp Ser Val Thr Glu Gln Leu Lys Val Gly Val Glu Val Lys Val Lys
            100                 105                 110

Ala Asn Ile Pro Leu Val Gly Gly Ala Glu Ile Thr Ser Thr Val Glu
        115                 120                 125

Leu Ser Leu Ser Ser Thr Gln Gly Ala Ser Thr Ser Lys Ser Ser Asn
    130                 135                 140

Tyr Gly Ala Ser Thr Lys Val Leu Ile Ser Pro His Ser His Gly Trp
145                 150                 155                 160

Gly Glu Val Ala Leu Ser Phe Thr Glu Leu Arg Thr Gln Trp Val Gly
                165                 170                 175

Asn Val Gly Leu Gln Gly Tyr Val Ala Ile Trp Phe Asn Asn Lys Val
            180                 185                 190

Ala Leu Asn Asn Asp Gly Asp Tyr His Tyr Leu Trp Phe Ile Pro Val
        195                 200                 205

Glu Gln Val Phe Trp Glu Cys Ile Gln His Asn Ile Val Asn Thr Ser
    210                 215                 220

Gly Tyr Val Val Gln Gly Asn Gly Val Leu Ala Gln Ala Thr Gly Thr
225                 230                 235                 240

Phe His Ser Ser Val Gly Leu Asn Leu Lys Thr Ile Ala His Glu Arg
                245                 250                 255

Pro Tyr Pro Glu Thr Ser Glu Ala Val Arg Thr Phe Tyr Asn Tyr Ala
            260                 265                 270

Ser Leu Val Pro Asp Leu Glu Thr Arg Val Arg Ser Ala Glu
        275                 280                 285
```

<210> SEQ ID NO 55
<211> LENGTH: 285
<212> TYPE: PRT
<213> ORGANISM: Pectobacterium wasabiae

<400> SEQUENCE: 55

```
Met Asn Asp Ile Asp Asn Ile Thr Asn Ala Trp Gly Lys Trp Ile Thr
1               5                   10                  15

Ala Gln Tyr Gly Thr Thr Cys Trp Phe Thr Glu Ser Thr Gln Tyr Ser
            20                  25                  30

Arg Asn Lys Asp Thr Lys Asp Tyr Met Gln His Gln Thr Asn Val Thr
        35                  40                  45

Pro Pro Lys Asp Leu Val Tyr Ser Ser Ala Val Gln Ser Asp Gly Gly
    50                  55                  60

Ala Ala Ile Leu Gly Lys Tyr Asp Ile Glu Asn Gly Gly Ser Gln Ile
65                  70                  75                  80

Ile Glu His Glu Val Asn Leu Gln Gln Gly Ile Glu Asp Ser Phe Thr
                85                  90                  95

Trp Asn Val Thr Glu Asn Val Lys Leu Gly Val Ser Val Lys Leu Lys
            100                 105                 110

Ala Gly Val Pro Phe Val Gly Ala Glu Thr Thr Leu Ser Thr Glu Leu
        115                 120                 125

Ser Leu Ser Ser Met Gln Gly Ser Thr Ile Thr Lys Thr Ser Asn Tyr
    130                 135                 140

Gly Ala Ser Val Lys Val Pro Ile Thr Pro His Thr His Ser Trp Gly
145                 150                 155                 160

Gln Ile Asn Leu Ser Phe Thr Asp Ile Ala Thr Ser Trp Val Gly Asn
                165                 170                 175

Val Lys Met Glu Gly Cys Val Ala Val Trp Phe Asn Lys Lys Val Ala
            180                 185                 190

Leu Asn Asn Asp Gly Asp Tyr His Trp Leu Trp Phe Val Pro Ile Gln
        195                 200                 205

Ser Val Phe Asn Asp Cys Ile Arg Asn Asn Ile Ile Asp Thr Arg Gly
    210                 215                 220

Tyr Ile Val Gln Trp Asp Gly Val Ile Ala Gln Ala Ser Gly Lys Phe
225                 230                 235                 240

His Ser Ser Arg Gly Leu Asp Met Lys Val Ile Ala Tyr Glu Gln Pro
                245                 250                 255

Leu Gly Thr Lys Arg Gln Glu Glu Ala Ile Gln Val Ile Val His Glu
            260                 265                 270

Phe Glu Ser Lys Tyr Arg Pro Ile Pro Ala Lys Val Glu
        275                 280                 285
```

<210> SEQ ID NO 56
<211> LENGTH: 825
<212> TYPE: PRT
<213> ORGANISM: Burkholderia ambifaria

<400> SEQUENCE: 56

```
Met Phe Leu Thr Arg Val Glu His Ser Leu Ser Asp Cys Lys Cys Ala
1               5                   10                  15

His Gln Asn Ile Tyr Glu Thr Glu Ile Tyr Asp Gly Thr Ser Trp Val
            20                  25                  30

Ala His Gly Gln Met Val Val Leu Glu Asp Ala Val Thr His Asn Gly
        35                  40                  45
```

```
Val His Ala His Asn Ile Gly Tyr Asn Gly Ser Asn His Ser Leu Val
    50                  55                  60

Leu Gln Gly Gly Thr Gly Arg Gln Arg Tyr Asn Ala Arg Leu Asn Leu
65                  70                  75                  80

Thr Glu Cys Gly Ser Ala Phe Val Gly Thr Leu Ala Val Ala Gly Asp
                85                  90                  95

Ala Pro Gln Ala Ile Arg Gly Val Ala Leu Ala Asn Val Phe Asp Thr
            100                 105                 110

Lys Arg Tyr Leu Arg Pro Lys Pro Lys Thr Lys Asp Asp Pro Ala Val
        115                 120                 125

Lys Cys Asp Pro Asn Ala Pro Ser Val Ala Trp Asp Gln Phe Ser Ile
    130                 135                 140

Lys Ala Gln Trp Ile Asp Asn Val Leu Thr Val Thr Tyr Leu Leu Gly
145                 150                 155                 160

His Val Asp Val Ser Asn Arg Val Arg Val Thr Ala Val Asp Arg Gln
                165                 170                 175

Lys Gly Glu Thr Thr Leu Glu Met Val Pro Gln Leu Asp Pro Pro Gly
            180                 185                 190

Pro Gln Asp Ser Phe Val Ile Thr Leu Tyr Ser Gly Asn Arg Thr Phe
        195                 200                 205

Gly Gly Glu Tyr Thr Ser Asp Asp Glu Glu Ala Tyr Cys Trp Phe Gly
    210                 215                 220

Ser Ser Thr Pro Ser Ile Ser Glu Gln Arg Ser Arg Val Phe Ala Glu
225                 230                 235                 240

Val Arg Glu Gly Ala Ala Ala Leu Ala Thr Thr Ala His Ile Ser Thr
                245                 250                 255

Pro Leu Glu Gly Asp Ala Ala Thr Arg Thr Leu Gln Asp Leu Asp Asn
            260                 265                 270

Ile Ser Ser Leu Thr Val Val Thr Asp Lys Asp Gly Asn Arg Met Thr
        275                 280                 285

Ile Asp His Ala Gln Thr Thr Cys Gly Gly Tyr Phe Asn Lys Cys Leu
    290                 295                 300

Val Asn Ala Leu Asp Ser Lys Trp Ile Glu Gly Ile Tyr Gly His Ala
305                 310                 315                 320

Tyr Leu Leu Pro Gly Gly Val Gln Lys Val Phe Asn Asp Lys Lys Ser
                325                 330                 335

Phe Phe Gln Lys Lys Ala Val Leu Gly Thr Gly Gln Met Leu Tyr Asp
            340                 345                 350

Asn Leu Gly Thr Ser Pro Thr Tyr Ala Asp Leu Ile Lys Arg Ile Lys
        355                 360                 365

Gly Asp Ala Met Lys Gln Ser Trp Lys Ser Leu Gly Asp Thr Lys Gly
    370                 375                 380

Gly Asp Lys Asp Glu Ser Leu Ala Tyr Gln Glu Ala Ser Asn Ala Leu
385                 390                 395                 400

Tyr Ile Glu Gly Tyr Arg Asp Gly Val Pro Glu Met Gln Pro Tyr Leu
                405                 410                 415

Gln Asp Asn Pro Lys Lys Trp Ala Ala Asp Tyr Phe Ala Trp Leu Ser
            420                 425                 430

Asp Glu Ala Asn Leu Leu Thr Trp Ser Ile Gln Val Ala Ser Lys Met
        435                 440                 445

Phe Asp Asn Val Arg Gln Arg Met Tyr Glu Trp Tyr Val Lys Leu Gln
    450                 455                 460
```

Val Leu Asp Pro Asp Ser Asn Tyr Gly Gln Arg Phe Met Thr Ile Ala
465 470 475 480

Tyr Ala Ala Leu Leu Gly Val Asn Tyr Ser Lys Ser Arg Trp Ser Asp
485 490 495

Asp Leu Lys Pro Phe Leu Thr Ser Leu Ile Glu Gln Ala Ile Ala Gly
500 505 510

Lys Val Asp Pro Thr Leu Met Asp Gln Ile Gln Gln Gln Ala Ala Leu
515 520 525

Glu Asn Gln Glu Leu Leu Lys Thr Leu Ile Thr Thr Thr Asp Ser Ile
530 535 540

His Asn Leu Val Asp Gly Ile Ala Ala Ala Ile Thr Glu Tyr Gln Leu
545 550 555 560

Lys Lys Gly Asn Gln Pro Leu Ser Arg Ile Ala Gln Asp Pro Glu Leu
565 570 575

Gln Gly Met Ile Gly Gln Arg Leu Asp Gly Gln Gln Tyr Lys Ala Trp
580 585 590

Gly Glu Leu Ser Arg Lys Gly Lys Val Gly Gly Val Leu Thr Val Val
595 600 605

Phe Tyr Gly Ala Ser Ala Gly Tyr Leu Ile Tyr Ser Leu Ala Asp Asn
610 615 620

Pro Gly Arg Pro Leu Thr Pro Lys Glu Ile Ile Glu Lys Ile Asn Leu
625 630 635 640

Gly Leu Leu Ala Leu Ala Thr Leu Val Lys Gly Val Gln Lys Met Met
645 650 655

Ser Ile Gly Val Gly Arg Phe Leu Glu Asn Phe Ser Lys Ala Ala Glu
660 665 670

Gly Gly Ala Phe Arg Ala Phe Ala Gly Asp Ile Ala Thr Trp Phe Lys
675 680 685

Ala Gly Gly Lys Ile Val Pro Glu Gly Lys Leu Gly Lys Ala Phe Val
690 695 700

Thr Ile Phe Gly Glu Ser Ser Ala Glu Phe Met Ala Arg Arg Ile Gly
705 710 715 720

Pro Ala Leu Ala Val Val Gly Met Ile Leu Ser Ser Phe Met Leu Tyr
725 730 735

Asp Ala Ile Lys Ser Gly Ala Val Arg Glu Ile Val Phe Glu Ala Leu
740 745 750

Asn Thr Phe Phe Ala Leu Ala Asp Val Val Phe Ile Gly Leu Glu Leu
755 760 765

Phe Ser Val Gly Trp Ala Gly Pro Val Gly Leu Ala Ile Ala Val Val
770 775 780

Gly Val Ile Val Ile Leu Val Gln Phe Ile Trp Asn Leu Ile Glu Pro
785 790 795 800

Pro Thr Pro Ala Pro Asp Pro Ile Thr Glu Phe Val Asn Gly Pro Met
805 810 815

Val Asn Gln Gly Phe Ala Val Ser Ala
820 825

<210> SEQ ID NO 57
<211> LENGTH: 802
<212> TYPE: PRT
<213> ORGANISM: Burkholderia ambifaria

<400> SEQUENCE: 57

Met Ala Arg Trp Ser Thr Lys Gly Ser Arg Phe Pro Arg Asn Gly Lys
1 5 10 15

```
Cys Arg Ala Pro Ala Arg Arg Leu Asp Pro His Ser Leu Ser Ile Ala
            20                  25                  30

Arg Cys Gln Glu Ile Ala Leu Leu Leu Thr Val Gln Arg Ser Ala Ile
        35                  40                  45

Arg Leu Ser Gly Ser Ser Asp Ser Ala Pro Asp Ser Val Ile Glu Gln
    50                  55                  60

Leu Val Asn Leu Leu Pro Asp Tyr Ser Gly Gly Arg Arg Leu His Ala
65                  70                  75                  80

Leu Leu Val Asn Arg Leu Lys Gly Ala Leu Pro Gly Asn Tyr Ser Gln
                85                  90                  95

Ile Phe Gly Thr Gly Pro Ser Phe Arg Ser Ile Phe Phe Ala Asp Tyr
            100                 105                 110

Gln Pro Asp Pro Leu Leu Pro Leu Met Ser Asp Met Gly Leu Asp Asp
        115                 120                 125

Gly Trp Trp Ala Asn Phe Ser Val Ala Val Leu Cys Gln Ser Ile Gln
    130                 135                 140

Asp Leu Gly Ser Arg Ile Arg Gly Gln Met Arg Ala Asp Lys Ile Asn
145                 150                 155                 160

His Asp Val Ala Ser Phe Asn Ala Thr Val Arg Gly Arg Cys Ala Arg
                165                 170                 175

Pro Tyr Ala Arg Val Leu Ala Ala Ser Phe Pro Pro Leu Ile Asn Leu
            180                 185                 190

Leu Asn Gln Val Asp His Ala Thr Ala Arg Gln Gln Phe His Asp Ala
        195                 200                 205

Leu Leu Gly Asn Val Ile Asn Arg Gln Leu Trp Tyr Gln Ala Gly Met
    210                 215                 220

Trp Thr Ser Pro Asp Trp Glu Met Phe Asn Gln Tyr Ala Lys Tyr Ile
225                 230                 235                 240

Ala Leu Gly Ala Asp Asp Ala Gln Val Asp Ala Leu Ile Asp Glu Leu
                245                 250                 255

Thr Ala Ala Gly Leu Pro Ile Pro Pro Gln Val Asn Arg Ser Asn Trp
            260                 265                 270

Arg Gly Tyr Ala Glu Ala Leu Arg Asp Lys Pro Asp Ile Asp Leu Asp
        275                 280                 285

Asp Val Gly Gly Asp Thr Ala Lys Pro Ile Gln Glu Thr Thr Tyr Leu
    290                 295                 300

Pro Ser Tyr Gly Arg Gly Met Pro Ala Arg Met Pro Asn Gly Asn Cys
305                 310                 315                 320

Tyr Glu Phe Thr Ala Gly Gly Gln Pro Gly Ser Pro Phe Arg Ala Pro
                325                 330                 335

Pro Ser Ser Cys Cys Phe Thr Gly Asp Thr Glu Val Leu Ser Gly Ala
            340                 345                 350

Gly Val Pro Val Pro Leu Asn Gln Val Lys Pro Gly Asp Thr Val Met
        355                 360                 365

Thr Arg Asp Gly Ala Ala Val Val Ala Phe Val Ala Arg Pro Gln Leu
    370                 375                 380

Gly Glu Arg Lys Leu Tyr Arg Ile Asn Gly Gly Gly Pro Val Phe Thr
385                 390                 395                 400

Asp Thr His Pro Phe Leu Asn Ala Ser Ala Ser Asp Ser Arg Ala Met
                405                 410                 415

Ala Pro Ala Ile Leu Ala Ala Asp Pro Ala His Leu Ala Trp Met Val
            420                 425                 430
```

-continued

```
Pro Thr Leu Ser Glu Asp Gly Ile Gly Lys Leu Thr Thr Gly Cys Val
        435                 440                 445

Leu Thr Gly Arg Arg Pro Glu Ser Ser Glu Ser Phe Pro Val Asp Val
    450                 455                 460

Thr Thr Val Glu Pro Val Pro Arg Gly Thr Gly Asp Asp Tyr Leu Tyr
465                 470                 475                 480

Asp Leu Asn Leu Leu Val Thr Thr Gly Ala Arg Gln Glu Phe Trp Ala
                485                 490                 495

Gly Lys Asp Gly Arg Phe Tyr Leu Val Ser Pro Glu Phe Pro Val Leu
            500                 505                 510

Ala Gln Ala Gly Ala Ala Ala Val Ala Val Val Ala Ala Leu Glu Gly
        515                 520                 525

Leu Ile Ala Ala Gly Gly Pro Thr Leu Ser Gly Trp Pro Val Thr Thr
    530                 535                 540

Arg Glu Leu Val His Arg Phe Gly Ala Ala Ile Phe Asp Ala Gly Leu
545                 550                 555                 560

Asp Ala Ala Leu Arg Thr Val Pro Ser Phe Gly Ser Pro Thr Pro Val
                565                 570                 575

Arg Pro Leu Phe Glu Arg Ile Asp Lys Leu Tyr Arg Asp Leu Gly Ser
            580                 585                 590

Val Asp Val Val Gly Ala Ser Ala Ile Ala Ala Phe Phe Asp Gly Phe
        595                 600                 605

Met Ser Thr Ile Val Thr Trp Leu Thr Ala Ser Val Ala Leu Gly Trp
    610                 615                 620

Arg Lys Pro Ala Glu Pro Ser Gly Glu Ile Val Val Val Thr Ile Phe
625                 630                 635                 640

Asp Met Ala Leu Ala Pro Gly Thr Pro Val Gln Thr Ala Ser Gln Ile
                645                 650                 655

Arg Met Glu Val Arg Ala Gln Gly Gln Ser Glu Ser Ala Ser Ala Met
            660                 665                 670

Met Trp Asn Arg Ser Gly Arg Ala Asn Thr Arg Phe His His Tyr Phe
        675                 680                 685

Asp Gln Leu Ile His Leu Asp Arg Ala Lys Leu Gly Ala Thr Gly Gly
    690                 695                 700

Leu Thr Phe Ala Val Val Met Asp Gly Ala Ser Val Pro Ala Leu Ser
705                 710                 715                 720

Gly Ala Ala Pro Leu Val Ile Gly Asp Arg Ala His Cys Phe Gln Ser
                725                 730                 735

Ala Gln Leu Phe Asp Ala Ala Gly Ala Ala Val Gly Thr Ile Arg Phe
            740                 745                 750

Asp Thr Arg Leu Leu Thr Arg Arg Thr Ala Glu Asp Glu Leu Ala His
        755                 760                 765

Ser Gly Leu Trp Thr Glu Glu Ala Ala Leu Ala Tyr Ser Asn Ala Leu
    770                 775                 780

Gly Thr Ala Met Ile Ala Pro Ile Leu Thr Thr Leu Glu Gly Leu Ala
785                 790                 795                 800

Gly Arg
```

<210> SEQ ID NO 58
<211> LENGTH: 825
<212> TYPE: PRT
<213> ORGANISM: Burkholderia cenocepacia

<400> SEQUENCE: 58

-continued

```
Met Phe Leu Thr Arg Val Glu His Ser Leu Ser Asp Cys Lys Cys Ala
1               5                   10                  15

His Gln Asn Ile Tyr Glu Thr Glu Ile Tyr Asp Gly Thr Ser Trp Val
            20                  25                  30

Ala His Gly Gln Met Val Val Leu Glu Asp Ala Val Thr His Asn Gly
        35                  40                  45

Val His Ala His Asn Ile Gly Tyr Asn Gly Ser Asn His Ser Leu Val
    50                  55                  60

Leu Gln Gly Gly Thr Gly Arg Gln Arg Tyr Asn Ala Arg Leu Asn Leu
65                  70                  75                  80

Thr Glu Cys Gly Ser Ala Phe Val Gly Thr Leu Ala Val Ala Gly Asp
                85                  90                  95

Ala Pro Gln Ala Ile Arg Gly Val Ala Leu Ala Asn Val Phe Asp Thr
            100                 105                 110

Lys Arg Tyr Leu Arg Pro Lys Pro Lys Thr Lys Asp Asp Pro Ala Val
        115                 120                 125

Lys Cys Asp Pro Asn Ala Pro Ser Val Ala Trp Asp Gln Phe Ser Ile
    130                 135                 140

Lys Ala Gln Trp Ile Asp Asn Val Leu Thr Val Thr Tyr Leu Leu Gly
145                 150                 155                 160

His Val Asp Val Ser Asn Arg Val Arg Val Thr Ala Val Asp Arg Lys
                165                 170                 175

Lys Gly Glu Thr Thr Leu Glu Met Val Pro Gln Leu Asp Pro Pro Gly
            180                 185                 190

Pro Gln Asp Ser Phe Val Ile Thr Leu Tyr Ser Gly Asn Arg Thr Phe
        195                 200                 205

Gly Gly Glu Tyr Thr Ser Asp Asp Glu Glu Ala Tyr Cys Trp Phe Gly
    210                 215                 220

Ser Ser Thr Pro Ser Ile Ser Glu Gln Arg Ser Arg Val Phe Ala Glu
225                 230                 235                 240

Val Arg Glu Gly Ala Ala Ala Leu Ala Thr Thr Ala Arg Ile Ser Thr
                245                 250                 255

Pro Leu Glu Gly Asp Ala Ala Thr Arg Thr Leu Gln Asp Leu Asp Asn
            260                 265                 270

Ile Ser Ser Leu Thr Val Val Thr Asp Lys Asp Gly Asn Arg Met Thr
        275                 280                 285

Ile Asp His Ala Gln Thr Thr Cys Gly Gly Tyr Phe Asn Lys Cys Leu
    290                 295                 300

Val Asn Ala Leu Asp Ser Lys Trp Ile Glu Gly Ile Tyr Gly His Ala
305                 310                 315                 320

Tyr Ser Leu Pro Gly Gly Val Gln Lys Val Phe Asn Asp Lys Lys Ser
                325                 330                 335

Phe Phe Gln Lys Lys Ala Val Leu Gly Thr Gly Gln Met Leu Tyr Asp
            340                 345                 350

Asn Leu Gly Thr Ser Pro Thr Tyr Ala Asp Leu Ile Lys Arg Ile Lys
        355                 360                 365

Gly Asp Ala Met Lys Gln Ser Trp Lys Ser Leu Gly Asp Thr Lys Gly
    370                 375                 380

Gly Asp Lys Asp Glu Ser Leu Ala Tyr Gln Glu Ala Ser Asn Ala Leu
385                 390                 395                 400

Tyr Ile Glu Gly Tyr Arg Asp Gly Val Pro Glu Met Gln Pro Tyr Leu
                405                 410                 415

Gln Asp Asn Pro Lys Lys Trp Ala Ala Asp Tyr Phe Ala Trp Leu Ser
```

```
            420                 425                 430

Asp Glu Ala Asn Leu Leu Thr Trp Ser Ile Gln Val Ala Ser Lys Met
        435                 440                 445

Phe Asp Asn Val Arg Gln Arg Met Tyr Glu Trp Tyr Val Lys Leu Gln
    450                 455                 460

Val Leu Asp Pro Asp Gly Asn Tyr Gly Gln Arg Phe Met Thr Ile Ala
465                 470                 475                 480

Tyr Ala Ala Leu Leu Gly Val Asn Tyr Ser Lys Ser Arg Trp Ser Asp
                485                 490                 495

Asp Leu Lys Pro Phe Leu Thr Ser Leu Ile Glu Gln Ala Ile Ala Gly
            500                 505                 510

Lys Val Asp Pro Thr Leu Met Asp Gln Ile Gln Gln Gln Ala Ala Leu
        515                 520                 525

Glu Asn Gln Glu Leu Leu Lys Thr Leu Ile Thr Thr Thr Asp Ser Ile
    530                 535                 540

His Asn Leu Val Asp Gly Ile Ala Ala Ala Ile Thr Glu Tyr Gln Leu
545                 550                 555                 560

Lys Lys Gly Asn Gln Pro Leu Ser Arg Ile Ala Gln Asp Pro Glu Leu
                565                 570                 575

Gln Gly Met Ile Gly Gln Arg Leu Asp Gly Gln Gln Tyr Lys Ala Trp
            580                 585                 590

Gly Glu Leu Ser Arg Lys Gly Lys Val Gly Gly Val Leu Thr Val Val
        595                 600                 605

Phe Tyr Gly Ala Ser Ala Gly Tyr Leu Ile Tyr Ser Leu Ala Asp Asn
    610                 615                 620

Pro Gly Arg Pro Leu Thr Pro Lys Glu Ile Ile Glu Lys Ile Asn Leu
625                 630                 635                 640

Gly Leu Leu Ala Leu Ala Thr Leu Val Lys Gly Val Gln Lys Met Met
                645                 650                 655

Ser Ile Gly Val Gly Arg Phe Leu Glu Asn Phe Ser Lys Ala Ala Glu
            660                 665                 670

Gly Gly Ala Phe Arg Ala Phe Ala Gly Asp Ile Ala Thr Trp Phe Lys
        675                 680                 685

Ala Gly Gly Lys Ile Val Pro Glu Gly Lys Leu Gly Lys Ala Phe Val
    690                 695                 700

Thr Ile Phe Gly Glu Ser Ser Ala Glu Phe Met Ala Arg Arg Ile Gly
705                 710                 715                 720

Pro Ala Leu Ala Val Val Gly Met Ile Leu Ser Ser Phe Met Leu Tyr
                725                 730                 735

Asp Ala Ile Lys Ser Gly Ala Val Arg Glu Ile Val Phe Glu Ala Leu
            740                 745                 750

Asn Thr Phe Phe Ala Leu Ala Asp Val Val Phe Ile Gly Leu Glu Leu
        755                 760                 765

Phe Ser Val Gly Trp Ala Gly Pro Val Gly Leu Ala Ile Ala Val Val
    770                 775                 780

Gly Val Ile Val Ile Leu Val Gln Phe Ile Trp Asn Leu Ile Glu Pro
785                 790                 795                 800

Pro Thr Pro Ala Pro Asp Pro Ile Thr Glu Phe Val Asn Gly Pro Met
                805                 810                 815

Val Asn Gln Gly Phe Ala Val Ser Ala
            820                 825
```

<210> SEQ ID NO 59

<211> LENGTH: 682
<212> TYPE: PRT
<213> ORGANISM: Burkholderia cenocepacia

<400> SEQUENCE: 59

Met Ser Asp Met Gly Leu Asp Asp Gly Trp Trp Ala Asn Phe Ser Val
1 5 10 15

Ala Val Leu Cys Gln Ser Ile Gln Asp Leu Gly Ser Arg Ile Arg Gly
20 25 30

Gln Met Arg Ala Asp Lys Ile Asn His Asp Val Ala Ser Phe Asn Ala
35 40 45

Thr Val Arg Gly Arg Cys Ala Arg Pro Tyr Ala Arg Val Leu Ala Ala
50 55 60

Ser Phe Pro Pro Leu Ile Asn Leu Leu Asn Gln Val Asp His Ala Thr
65 70 75 80

Ala Arg Gln Gln Phe His Asp Ala Leu Leu Gly Asn Val Ile Asn Arg
85 90 95

Gln Leu Trp Tyr Gln Ala Gly Met Trp Thr Ser Pro Asp Trp Glu Met
100 105 110

Phe Asn Gln Tyr Ala Lys Tyr Ile Ala Leu Gly Ala Asp Asp Ala Gln
115 120 125

Val Asp Ala Leu Ile Asp Glu Leu Thr Ala Ala Gly Leu Pro Ile Pro
130 135 140

Pro Gln Val Asn Arg Ser Asn Trp Arg Gly Tyr Ala Glu Ala Leu Arg
145 150 155 160

Asp Lys Pro Asp Ile Asp Leu Asp Asp Val Gly Gly Asp Thr Ala Lys
165 170 175

Pro Ile Gln Glu Thr Thr Tyr Leu Pro Ser Tyr Gly Arg Gly Met Pro
180 185 190

Ala Arg Met Pro Asn Gly Asn Cys Tyr Glu Phe Thr Ala Gly Gly Gln
195 200 205

Pro Gly Ser Pro Phe Arg Ala Pro Pro Ser Ser Cys Cys Leu Thr Gly
210 215 220

Asp Thr Glu Val Leu Ser Gly Ala Gly Val Pro Val Pro Leu Asn Gln
225 230 235 240

Val Lys Pro Gly Asp Thr Val Met Thr Arg Asp Gly Ala Ala Val Val
245 250 255

Ala Phe Val Ala Arg Pro Gln Leu Gly Glu Arg Lys Leu Tyr Arg Ile
260 265 270

Asn Gly Gly Gly Pro Val Phe Thr Asp Thr His Pro Phe Leu Asn Ala
275 280 285

Ser Ala Ser Asp Ser Arg Ala Thr Ala Pro Ala Ile Leu Ala Ala Asp
290 295 300

Pro Ser His Leu Ala Trp Met Val Pro Thr Leu Ser Glu Asp Gly Ile
305 310 315 320

Gly Lys Leu Thr Thr Gly Cys Val Leu Thr Gly Arg Arg Pro Glu Ser
325 330 335

Ser Glu Ser Phe Pro Val Asp Val Thr Thr Val Glu Pro Val Pro Arg
340 345 350

Gly Thr Gly Asp Asp Tyr Leu Tyr Asp Leu Asn Leu Leu Val Thr Thr
355 360 365

Gly Ala Arg Gln Glu Phe Trp Ala Gly Lys Asp Gly Arg Phe Tyr Leu
370 375 380

Val Ser Pro Glu Phe Pro Val Leu Ala Gln Ala Gly Ala Ala Ala Val

```
385                 390                 395                 400

Ala Val Val Ala Ala Leu Glu Gly Leu Ile Ala Ala Gly Gly Pro Thr
                405                 410                 415

Leu Ser Gly Trp Pro Val Thr Thr Arg Glu Leu Val His Arg Phe Gly
            420                 425                 430

Ala Ala Ile Phe Asp Ala Gly Leu Asp Ala Ala Leu Arg Thr Val Pro
        435                 440                 445

Ser Phe Gly Ser Pro Thr Pro Val Arg Pro Leu Phe Glu Arg Ile Asp
    450                 455                 460

Lys Leu Tyr Arg Asp Leu Gly Ser Val Asp Val Val Gly Ala Ser Ala
465                 470                 475                 480

Ile Ala Ala Phe Phe Asp Gly Phe Met Ser Thr Ile Val Thr Trp Leu
                485                 490                 495

Thr Ala Ser Val Ala Leu Gly Trp Arg Lys Pro Ala Glu Pro Ser Gly
            500                 505                 510

Glu Ile Val Val Val Thr Ile Phe Asp Met Ala Leu Ala Pro Gly Thr
        515                 520                 525

Pro Val Gln Thr Ala Ser Gln Ile Arg Met Glu Val Arg Ala Gln Gly
    530                 535                 540

Gln Ser Glu Ser Ala Ser Thr Thr Met Trp Asn Arg Ser Gly Arg Ala
545                 550                 555                 560

Asn Thr Arg Phe His His Tyr Phe Asp Gln Leu Ile His Leu Asp Arg
                565                 570                 575

Ala Lys Leu Gly Ala Thr Gly Gly Leu Thr Phe Ala Val Val Met Asp
            580                 585                 590

Gly Ala Ser Val Pro Ala Leu Ser Gly Ala Ala Pro Leu Val Ile Gly
        595                 600                 605

Asp Arg Ala His Cys Phe Gln Ser Ala Gln Leu Phe Asp Ala Ala Gly
    610                 615                 620

Thr Ala Val Gly Thr Ile Arg Phe Asp Thr Arg Leu Leu Thr Arg Arg
625                 630                 635                 640

Thr Ala Glu Asp Glu Leu Ala His Ser Gly Leu Trp Thr Glu Glu Ala
                645                 650                 655

Ala Leu Ala Tyr Ser Asn Ala Leu Gly Thr Ala Met Val Ala Pro Ile
            660                 665                 670

Leu Thr Thr Leu Glu Gly Leu Ala Gly Arg
        675                 680


<210> SEQ ID NO 60
<211> LENGTH: 764
<212> TYPE: PRT
<213> ORGANISM: Burkholderia cepacia

<400> SEQUENCE: 60

Met Leu Leu Thr Val Gln Arg Ser Ala Ile Arg Leu Arg Gly Thr Ser
1               5                   10                  15

Asp Ser Ala Pro Asp Ser Val Ile Glu Gln Leu Val Asn Leu Leu Pro
            20                  25                  30

Asp Tyr Ser Gly Gly Arg Arg Leu His Ala Leu Leu Val Asn Arg Leu
        35                  40                  45

Lys Gly Ala Leu Pro Gly Asn Tyr Ser Gln Ile Phe Gly Thr Gly Pro
    50                  55                  60

Ser Phe Arg Ser Ile Phe Phe Ala Asp Tyr Gln Pro Asp Pro Leu Leu
65                  70                  75                  80
```

-continued

```
Pro Leu Met Ser Asp Met Gly Leu Asp Asp Gly Trp Trp Ala Asn Phe
                85                  90                  95

Ser Val Ala Val Leu Cys Gln Ser Ile Gln Asp Leu Gly Ser Arg Ile
            100                 105                 110

Arg Gly Gln Met Arg Ala Asp Lys Ile Asn His Asp Val Ala Ser Phe
        115                 120                 125

Asn Ala Thr Val Arg Gly Arg Cys Ala Arg Pro Tyr Ala Arg Val Leu
    130                 135                 140

Ala Ala Ser Phe Pro Pro Leu Ile Asn Leu Leu Asn Gln Val Asp His
145                 150                 155                 160

Ala Thr Ala Arg Gln Gln Phe His Asp Ala Leu Leu Gly Asn Val Ile
                165                 170                 175

Asn Arg Gln Leu Trp Tyr Gln Ala Gly Met Trp Thr Ser Pro Asp Trp
            180                 185                 190

Glu Met Phe Asn Gln Tyr Ala Lys Tyr Ile Ala Leu Gly Ala Asp Asp
        195                 200                 205

Ala Gln Val Asp Ala Leu Ile Asp Glu Leu Thr Ala Ala Gly Leu Pro
    210                 215                 220

Ile Pro Pro Gln Val Asn Arg Ser Asn Trp Arg Gly Tyr Ala Glu Ala
225                 230                 235                 240

Leu Arg Asp Lys Pro Asp Ile Asp Leu Asp Asp Val Gly Gly Asp Thr
                245                 250                 255

Ala Lys Pro Ile Gln Glu Thr Thr Tyr Leu Pro Ser Tyr Gly Arg Gly
            260                 265                 270

Met Pro Ala Arg Met Pro Asn Gly Asn Cys Tyr Glu Phe Thr Ala Gly
        275                 280                 285

Gly Gln Pro Gly Ser Pro Phe Arg Ala Pro Pro Ser Ser Cys Cys Phe
    290                 295                 300

Thr Gly Asp Thr Glu Val Leu Ser Gly Ala Gly Val Pro Val Pro Leu
305                 310                 315                 320

Asn Gln Val Lys Pro Gly Asp Thr Val Met Thr Arg Asp Gly Ala Ala
                325                 330                 335

Val Val Ala Phe Val Ala Arg Pro Gln Leu Gly Glu Arg Lys Leu Tyr
            340                 345                 350

Arg Ile Asn Gly Gly Gly Pro Val Phe Thr Asp Thr His Pro Phe Leu
        355                 360                 365

Asn Ala Ser Ala Ser Asp Ser Arg Ala Met Ala Pro Ala Ile Leu Ala
    370                 375                 380

Ala Asp Pro Ala His Leu Ala Trp Met Val Pro Thr Leu Ser Glu Asp
385                 390                 395                 400

Gly Ile Gly Lys Leu Thr Thr Gly Cys Val Leu Thr Gly Arg Arg Pro
                405                 410                 415

Glu Ser Ser Glu Ser Phe Pro Val Asp Val Thr Thr Val Glu Pro Val
            420                 425                 430

Pro Arg Gly Thr Gly Asp Asp Tyr Leu Tyr Asp Leu Asn Leu Leu Val
        435                 440                 445

Thr Thr Gly Ala Arg Gln Glu Phe Trp Ala Gly Lys Asp Gly Arg Phe
    450                 455                 460

Tyr Leu Val Ser Pro Glu Phe Pro Val Leu Ala Gln Ala Gly Ala Ala
465                 470                 475                 480

Ala Val Ala Val Val Ala Ala Leu Glu Gly Leu Ile Ala Ala Gly Gly
                485                 490                 495

Pro Thr Leu Ser Gly Trp Pro Val Thr Thr Arg Glu Leu Val His Arg
```

```
            500                 505                 510

Phe Gly Ala Ala Ile Phe Asp Ala Gly Leu Asp Ala Ala Leu Arg Thr
        515                 520                 525

Val Pro Ser Phe Gly Ser Pro Thr Pro Val Arg Pro Leu Phe Glu Arg
    530                 535                 540

Ile Asp Lys Leu Tyr Arg Asp Leu Gly Ser Val Asp Val Val Gly Ala
545                 550                 555                 560

Ser Ala Ile Ala Ala Phe Phe Asp Gly Phe Met Ser Thr Ile Val Thr
                565                 570                 575

Trp Leu Thr Ala Ser Val Ala Leu Gly Trp Arg Lys Pro Ala Glu Pro
            580                 585                 590

Ser Gly Glu Ile Val Val Val Thr Ile Phe Asp Met Ala Leu Ala Pro
        595                 600                 605

Gly Thr Pro Val Gln Thr Ala Ser Gln Ile Arg Met Glu Val Arg Ala
    610                 615                 620

Gln Gly Gln Ser Glu Ser Ala Ser Ala Met Met Trp Asn Arg Ser Gly
625                 630                 635                 640

Arg Ala Asn Thr Arg Phe His His Tyr Phe Asp Gln Leu Ile His Leu
                645                 650                 655

Asp Arg Ala Lys Leu Gly Ala Thr Gly Gly Leu Thr Phe Ala Val Val
            660                 665                 670

Met Asp Gly Ala Ser Val Pro Ala Leu Ser Gly Ala Ala Pro Leu Val
        675                 680                 685

Ile Gly Asp Arg Ala His Cys Phe Gln Ser Ala Gln Leu Phe Asp Ala
    690                 695                 700

Ala Gly Ala Ala Val Gly Thr Ile Arg Phe Asp Thr Arg Leu Leu Thr
705                 710                 715                 720

Arg Arg Thr Ala Glu Asp Glu Leu Ala His Ser Gly Leu Trp Thr Glu
                725                 730                 735

Glu Ala Ala Leu Ala Tyr Ser Asn Ala Leu Gly Thr Ala Met Ile Ala
            740                 745                 750

Pro Ile Leu Thr Thr Leu Glu Gly Leu Ala Gly Arg
        755                 760


<210> SEQ ID NO 61
<211> LENGTH: 825
<212> TYPE: PRT
<213> ORGANISM: Burkholderia cepacia

<400> SEQUENCE: 61

Met Phe Leu Thr Arg Val Glu His Ser Leu Ser Asp Cys Lys Cys Ala
1               5                   10                  15

His Gln Asn Ile Tyr Glu Thr Glu Ile Tyr Asp Gly Thr Ser Trp Val
            20                  25                  30

Ala His Gly Gln Met Val Val Leu Glu Asp Ala Val Thr His Asn Gly
        35                  40                  45

Val His Ala His Asn Ile Gly Tyr Asn Gly Ser Asn His Ser Leu Val
    50                  55                  60

Leu Gln Gly Gly Thr Gly Arg Gln Arg Tyr Asn Ala Arg Leu Asn Leu
65                  70                  75                  80

Thr Glu Cys Gly Ser Ala Phe Val Gly Thr Leu Ala Val Ala Gly Asp
                85                  90                  95

Ala Pro Gln Ala Ile Arg Gly Val Ala Leu Ala Asn Val Phe Asp Thr
            100                 105                 110
```

-continued

```
Lys Arg Tyr Leu Arg Pro Lys Pro Lys Thr Lys Asp Asp Pro Ala Val
        115                 120                 125

Lys Cys Asp Pro Asn Ala Pro Ser Val Ala Trp Asp Gln Phe Ser Ile
    130                 135                 140

Lys Ala Gln Trp Ile Asp Asn Val Leu Thr Val Thr Tyr Leu Leu Gly
145                 150                 155                 160

Leu Val Asp Val Ser Asn Arg Val Arg Val Thr Ala Val Asp Arg Lys
                165                 170                 175

Lys Gly Glu Thr Thr Leu Glu Met Val Pro Gln Leu Asp Pro Pro Gly
            180                 185                 190

Pro Gln Asp Ser Phe Val Ile Thr Leu Tyr Ser Gly Asn Arg Thr Phe
        195                 200                 205

Gly Gly Glu Tyr Thr Ser Asp Asp Glu Glu Ala Tyr Cys Trp Phe Gly
    210                 215                 220

Ser Ser Thr Pro Ser Ile Ser Glu Gln Arg Ser Arg Val Phe Ala Glu
225                 230                 235                 240

Val Arg Glu Gly Ala Ala Ala Leu Ala Thr Thr Ala Arg Ile Ser Thr
                245                 250                 255

Pro Leu Glu Gly Asp Ala Ala Thr Arg Thr Leu Gln Asp Leu Asp Asn
            260                 265                 270

Ile Ser Ser Leu Thr Val Val Thr Asp Lys Asp Gly Asn Arg Met Thr
        275                 280                 285

Ile Asp His Ala Gln Thr Thr Cys Gly Gly Tyr Phe Asn Lys Cys Leu
    290                 295                 300

Val Asn Ala Leu Asp Ser Lys Trp Ile Glu Gly Ile Tyr Gly His Ala
305                 310                 315                 320

Tyr Ser Leu Pro Gly Gly Val Gln Lys Val Phe Asn Asp Lys Lys Ser
                325                 330                 335

Phe Phe Gln Lys Lys Ala Val Leu Gly Thr Gly Gln Met Leu Tyr Asp
            340                 345                 350

Asn Leu Gly Thr Ser Pro Thr Tyr Ala Asp Leu Ile Lys Arg Ile Lys
        355                 360                 365

Gly Asp Ala Met Lys Gln Ser Trp Lys Ser Leu Gly Asp Thr Lys Gly
    370                 375                 380

Gly Asp Lys Asp Glu Ser Leu Ala Tyr Gln Glu Ala Ser Asn Ala Leu
385                 390                 395                 400

Tyr Ile Glu Gly Tyr Arg Asp Gly Val Pro Glu Met Gln Pro Tyr Leu
                405                 410                 415

Gln Asp Asn Pro Lys Lys Trp Ala Ala Asp Tyr Phe Ala Trp Leu Ser
            420                 425                 430

Asp Glu Ala Asn Leu Leu Thr Trp Ser Ile Gln Val Ala Ser Lys Met
        435                 440                 445

Phe Asp Asn Val Arg Gln Arg Met Tyr Glu Trp Tyr Val Lys Leu Gln
    450                 455                 460

Val Leu Asp Pro Asp Gly Asn Tyr Gly Gln Arg Phe Met Thr Ile Ala
465                 470                 475                 480

Tyr Ala Ala Leu Leu Gly Val Asn Tyr Ser Lys Ser Arg Trp Ser Asp
                485                 490                 495

Asp Leu Lys Pro Phe Leu Thr Ser Leu Ile Glu Gln Ala Ile Ala Gly
            500                 505                 510

Lys Val Asp Pro Thr Leu Met Asp Gln Ile Gln Gln Gln Ala Ala Leu
        515                 520                 525

Glu Asn Gln Glu Leu Leu Lys Thr Leu Ile Thr Thr Thr Asp Ser Ile
```

```
    530                 535                 540

His Asn Leu Val Asp Gly Ile Ala Ala Ala Ile Thr Glu Tyr Gln Leu
545                 550                 555                 560

Lys Lys Gly Asn Gln Pro Leu Ser Arg Ile Ala Gln Asp Pro Glu Leu
                565                 570                 575

Gln Gly Met Ile Gly Gln Arg Leu Asp Gly Gln Gln Tyr Lys Ala Trp
            580                 585                 590

Gly Glu Leu Ser Arg Lys Gly Lys Val Gly Gly Val Leu Thr Val Val
        595                 600                 605

Phe Tyr Gly Ala Ser Ala Gly Tyr Leu Ile Tyr Ser Leu Ala Asp Asn
    610                 615                 620

Pro Gly Arg Pro Leu Thr Pro Lys Glu Ile Ile Glu Lys Ile Asn Leu
625                 630                 635                 640

Gly Leu Leu Ala Leu Ala Thr Leu Val Lys Gly Val Gln Lys Met Met
                645                 650                 655

Ser Ile Gly Val Gly Arg Phe Leu Glu Asn Phe Ser Lys Ala Ala Glu
            660                 665                 670

Gly Gly Ala Phe Arg Ala Phe Ala Gly Asp Ile Ala Thr Trp Phe Lys
        675                 680                 685

Ala Gly Gly Lys Ile Val Pro Glu Gly Lys Leu Gly Lys Ala Phe Val
    690                 695                 700

Thr Ile Phe Gly Glu Ser Ser Ala Glu Phe Met Ala Arg Arg Ile Gly
705                 710                 715                 720

Pro Ala Leu Ala Val Val Gly Met Ile Leu Ser Ser Phe Met Leu Tyr
                725                 730                 735

Asp Ala Ile Lys Ser Gly Ala Val Arg Glu Ile Val Phe Glu Ala Leu
            740                 745                 750

Asn Thr Phe Phe Ala Leu Ala Asp Val Val Phe Ile Gly Leu Glu Leu
        755                 760                 765

Phe Ser Val Gly Trp Ala Gly Pro Val Gly Leu Ala Ile Ala Val Val
    770                 775                 780

Gly Val Ile Val Ile Leu Val Gln Phe Ile Trp Asn Leu Ile Glu Pro
785                 790                 795                 800

Pro Thr Pro Ala Pro Asp Pro Ile Thr Glu Phe Val Asn Gly Pro Met
                805                 810                 815

Val Asn Gln Gly Phe Ala Val Ser Ala
            820                 825


<210> SEQ ID NO 62
<211> LENGTH: 555
<212> TYPE: PRT
<213> ORGANISM: Burkholderia cepacia

<400> SEQUENCE: 62

Met Leu Leu Thr Val Gln Arg Ser Ala Ile Arg Leu Ser Gly Ser Ser
1               5                   10                  15

Asp Ser Ala Pro Asp Ser Val Ile Glu Gln Leu Val Asn Leu Leu Pro
            20                  25                  30

Asp Tyr Ser Gly Gly Arg Arg Leu His Ala Leu Leu Val Asn Arg Leu
        35                  40                  45

Lys Gly Ala Leu Pro Gly Asn Tyr Ser Gln Ile Phe Gly Thr Gly Pro
    50                  55                  60

Ser Phe Arg Ser Ile Phe Phe Ser Asp Tyr Gln Pro Asp Pro Leu Leu
65                  70                  75                  80
```

-continued

```
Pro Leu Met Ser Asp Met Gly Leu Asp Asp Gly Trp Trp Ala Asn Phe
                85                  90                  95

Ser Val Ala Val Leu Cys Gln Ser Ile Gln Asp Leu Gly Ser Arg Ile
            100                 105                 110

Arg Gly Gln Met Arg Ala Asp Lys Ile Asn His Asp Val Ala Ser Phe
        115                 120                 125

Asn Ala Thr Val Arg Gly Arg Cys Ala Arg Pro Tyr Ala Arg Val Leu
    130                 135                 140

Ala Ala Ser Phe Pro Pro Leu Ile Asn Leu Leu Asn Gln Val Asp His
145                 150                 155                 160

Ala Thr Ala Arg Gln Gln Phe His Asp Ala Leu Leu Gly Asn Val Ile
                165                 170                 175

Asn Arg Gln Leu Trp Tyr Gln Ala Gly Met Trp Thr Ser Pro Asp Trp
            180                 185                 190

Glu Met Phe Asn Gln Tyr Ala Lys Tyr Ile Ala Leu Gly Ala Asp Asp
        195                 200                 205

Ala Gln Val Asp Ala Leu Ile Asp Glu Leu Thr Ala Ala Gly Leu Pro
    210                 215                 220

Ile Pro Pro Gln Val Asn Arg Ser Asn Trp Arg Gly Tyr Ala Glu Ala
225                 230                 235                 240

Leu Arg Asp Lys Pro Asp Ile Asp Leu Asp Asp Val Gly Gly Asp Thr
                245                 250                 255

Ala Lys Pro Ile Gln Glu Thr Thr Tyr Leu Pro Ser Tyr Gly Arg Gly
            260                 265                 270

Met Pro Ala Arg Met Pro Asn Gly Asn Cys Tyr Glu Phe Thr Ala Gly
        275                 280                 285

Gly Gln Pro Gly Ser Pro Phe Arg Ala Pro Pro Ser Ser Cys Cys Leu
    290                 295                 300

Thr Gly Asp Thr Glu Val Leu Ser Gly Ala Gly Val Pro Val Pro Leu
305                 310                 315                 320

Asn Gln Val Lys Pro Gly Asp Thr Val Met Thr Arg Asp Gly Ala Ala
                325                 330                 335

Val Val Ala Phe Val Ala Arg Pro Gln Leu Gly Glu Arg Lys Leu Tyr
            340                 345                 350

Arg Ile Asn Gly Gly Gly Pro Val Phe Thr Asp Thr His Pro Phe Leu
        355                 360                 365

Asn Ala Ser Ala Ser Asp Ser Arg Ala Thr Ala Pro Ala Ile Leu Ala
    370                 375                 380

Ala Asp Pro Ala His Leu Ala Trp Met Val Pro Thr Leu Ser Glu Asp
385                 390                 395                 400

Gly Ile Gly Lys Leu Thr Thr Gly Cys Val Leu Thr Gly Arg Arg Pro
                405                 410                 415

Glu Ser Ser Glu Ser Phe Pro Val Asp Val Thr Thr Val Glu Pro Val
            420                 425                 430

Pro Arg Gly Thr Gly Asp Asp Tyr Leu Tyr Asp Leu Asn Leu Leu Val
        435                 440                 445

Thr Thr Gly Ala Arg Gln Glu Phe Trp Ala Gly Lys Asp Gly Arg Phe
    450                 455                 460

Tyr Leu Val Ser Pro Glu Phe Pro Val Leu Ala Gln Ala Gly Ala Ala
465                 470                 475                 480

Ala Val Ala Val Val Ala Ala Leu Glu Gly Leu Ile Ala Ala Gly Gly
                485                 490                 495

Pro Thr Leu Ser Gly Trp Pro Val Thr Thr Gln Glu Leu Val His Arg
```

500 505 510

Phe Gly Ala Ala Ile Phe Asp Ala Gly Leu Asp Ala Ala Leu Arg Thr
515 520 525

Val Pro Ser Phe Gly Ser Pro Thr Pro Val Arg Pro Leu Phe Glu Arg
530 535 540

Ile Asp Lys Leu Tyr Arg Asp Leu Gly Ser Val
545 550 555

<210> SEQ ID NO 63
<211> LENGTH: 682
<212> TYPE: PRT
<213> ORGANISM: Burkholderia cepacia

<400> SEQUENCE: 63

Met Ser Asp Met Gly Leu Asp Asp Gly Trp Trp Ala Asn Phe Ser Val
1 5 10 15

Ala Val Leu Cys Gln Ser Ile Gln Asp Leu Gly Ser Arg Ile Arg Gly
20 25 30

Gln Met Arg Ala Asp Lys Ile Asn His Asp Val Ala Ser Phe Asn Ala
35 40 45

Thr Val Arg Gly Arg Cys Ala Arg Pro Tyr Ala Arg Val Leu Ala Ala
50 55 60

Ser Phe Pro Pro Leu Ile Asn Leu Leu Asn Gln Val Asp His Ala Thr
65 70 75 80

Ala Arg Gln Gln Phe His Asp Ala Leu Leu Gly Asn Val Ile Asn Arg
85 90 95

Gln Leu Trp Tyr Gln Ala Gly Met Trp Thr Ser Pro Asp Trp Glu Met
100 105 110

Phe Asn Gln Tyr Ala Lys Tyr Ile Ala Leu Gly Ala Asp Asp Ala Gln
115 120 125

Val Asp Ala Leu Ile Asp Glu Leu Thr Ala Ala Gly Leu Pro Ile Pro
130 135 140

Pro Gln Val Asn Arg Ser Asn Trp Arg Gly Tyr Ala Glu Ala Leu Arg
145 150 155 160

Asp Lys Pro Asp Ile Asp Leu Asp Asp Val Gly Gly Asp Thr Ala Lys
165 170 175

Pro Ile Gln Glu Thr Thr Tyr Leu Pro Ser Tyr Gly Arg Gly Met Pro
180 185 190

Ala Arg Met Pro Asn Gly Asn Cys Tyr Glu Phe Thr Ala Gly Gly Gln
195 200 205

Pro Gly Ser Pro Phe Arg Ala Pro Pro Ser Ser Cys Cys Leu Thr Gly
210 215 220

Asp Thr Glu Val Leu Ser Gly Ala Gly Val Pro Val Pro Leu Asn Gln
225 230 235 240

Val Lys Pro Gly Asp Thr Val Met Thr Arg Asp Gly Ala Ala Val Val
245 250 255

Ala Phe Val Ala Arg Pro Gln Leu Gly Glu Arg Lys Leu Tyr Arg Ile
260 265 270

Asn Gly Gly Gly Pro Val Phe Thr Asp Thr His Pro Phe Leu Asn Ala
275 280 285

Ser Ala Ser Asp Ser Arg Ala Thr Ala Pro Ala Ile Leu Ala Ala Asp
290 295 300

Pro Ala His Leu Ala Trp Met Val Pro Thr Leu Ser Glu Asp Gly Ile
305 310 315 320

-continued

```
Gly Lys Leu Thr Thr Gly Cys Val Leu Thr Gly Arg Arg Pro Glu Ser
                325                 330                 335

Ser Glu Ser Phe Pro Val Asp Val Thr Thr Val Glu Pro Val Pro Arg
            340                 345                 350

Gly Thr Gly Asp Asp Tyr Leu Tyr Asp Leu Asn Leu Leu Val Thr Thr
        355                 360                 365

Gly Ala Arg Gln Glu Phe Trp Ala Gly Lys Asp Gly Arg Phe Tyr Leu
    370                 375                 380

Val Ser Pro Glu Phe Pro Val Leu Ala Gln Ala Gly Ala Ala Ala Val
385                 390                 395                 400

Ala Val Val Ala Ala Leu Glu Gly Leu Ile Ala Ala Gly Gly Pro Thr
                405                 410                 415

Leu Ser Gly Trp Pro Val Thr Thr Gln Glu Leu Val His Arg Phe Gly
            420                 425                 430

Ala Ala Ile Phe Asp Ala Gly Leu Asp Ala Ala Leu Arg Thr Val Pro
        435                 440                 445

Ser Phe Gly Ser Pro Thr Pro Val Arg Pro Leu Phe Glu Arg Ile Asp
    450                 455                 460

Lys Leu Tyr Arg Asp Leu Gly Ser Val Asp Val Val Gly Ala Ser Ala
465                 470                 475                 480

Ile Ala Ala Phe Phe Asp Gly Phe Met Ser Thr Ile Val Thr Trp Leu
                485                 490                 495

Thr Ala Ser Val Ala Leu Gly Trp Arg Lys Pro Ala Glu Pro Ser Gly
            500                 505                 510

Glu Ile Val Val Val Thr Ile Phe Asp Met Ala Leu Ala Pro Gly Thr
        515                 520                 525

Pro Val Gln Thr Ala Ser Gln Ile Arg Met Glu Val Arg Ala Gln Gly
    530                 535                 540

Gln Ser Glu Ser Ala Ser Thr Met Met Trp Asn Arg Ser Gly Arg Ala
545                 550                 555                 560

Asn Thr Arg Phe His His Tyr Phe Asp Gln Leu Ile His Leu Asp Arg
                565                 570                 575

Ala Lys Leu Gly Ala Thr Gly Gly Leu Thr Phe Ala Val Val Met Asp
            580                 585                 590

Gly Ala Ser Val Pro Ala Leu Ser Gly Ala Ala Pro Leu Val Ile Gly
        595                 600                 605

Asp Arg Ala His Cys Phe Gln Ser Ala Gln Leu Phe Asp Ala Ala Gly
    610                 615                 620

Thr Ala Val Gly Thr Ile Arg Phe Asp Thr Arg Leu Leu Thr Arg Arg
625                 630                 635                 640

Thr Ala Glu Asp Glu Leu Ala His Ser Gly Leu Trp Thr Glu Glu Ala
                645                 650                 655

Ala Leu Ala Tyr Ser Asn Ala Leu Gly Thr Ala Met Val Ala Pro Ile
            660                 665                 670

Leu Thr Thr Leu Glu Gly Leu Ala Gly Arg
        675                 680
```

<210> SEQ ID NO 64
<211> LENGTH: 825
<212> TYPE: PRT
<213> ORGANISM: Burkholderia cepacia

<400> SEQUENCE: 64

```
Met Phe Leu Thr Arg Val Glu His Ser Leu Ser Asp Cys Lys Cys Ala
1               5                   10                  15
```

-continued

```
His Gln Asn Ile Tyr Glu Thr Glu Ile Tyr Asp Gly Thr Ser Trp Val
            20                  25                  30

Ala His Gly Gln Met Val Val Leu Glu Asp Ala Val Thr His Asn Gly
        35                  40                  45

Val His Ala His Asn Ile Gly Tyr Asn Gly Ser Asn His Ser Leu Val
    50                  55                  60

Leu Gln Gly Gly Thr Gly Arg Gln Arg Tyr Asn Ala Arg Leu Asn Leu
65                  70                  75                  80

Thr Glu Cys Gly Ser Ala Phe Val Gly Thr Leu Glu Val Ala Gly Asp
                85                  90                  95

Ala Pro Gln Ala Ile Arg Gly Val Ala Leu Ala Asn Val Phe Asp Thr
            100                 105                 110

Lys Arg Tyr Leu Arg Pro Lys Pro Lys Thr Lys Asp Asp Pro Ala Val
        115                 120                 125

Lys Cys Asp Pro Asn Ala Pro Ser Val Ala Trp Asp Gln Phe Ser Ile
    130                 135                 140

Lys Ala Gln Trp Ile Asp Asn Val Leu Thr Val Thr Tyr Leu Leu Gly
145                 150                 155                 160

His Val Asp Val Ser Asn Arg Val Arg Val Thr Ala Val Asp Arg Gln
                165                 170                 175

Lys Gly Glu Thr Thr Leu Glu Met Val Pro Gln Leu Asp Pro Pro Gly
            180                 185                 190

Pro Gln Asp Ser Phe Val Ile Thr Leu Tyr Ser Gly Asn Arg Thr Phe
        195                 200                 205

Gly Gly Glu Tyr Thr Ser Asp Asp Glu Glu Ala Tyr Cys Trp Phe Gly
    210                 215                 220

Ser Ser Thr Pro Ser Ile Ser Glu Gln Arg Ser Arg Val Phe Ala Glu
225                 230                 235                 240

Val Arg Glu Gly Ala Ala Ala Leu Ala Thr Thr Ala Arg Ile Ser Thr
                245                 250                 255

Pro Leu Glu Gly Asp Ala Ala Thr Arg Thr Leu Gln Asp Leu Asp Asn
            260                 265                 270

Ile Ser Ser Leu Thr Val Val Thr Asp Lys Asp Gly Asn Arg Met Thr
        275                 280                 285

Ile Asp His Ala Gln Thr Thr Cys Gly Gly Tyr Phe Asn Lys Cys Leu
    290                 295                 300

Val Asn Ala Leu Asp Ser Lys Trp Ile Glu Gly Ile Tyr Gly His Ala
305                 310                 315                 320

Tyr Leu Leu Pro Gly Gly Val Gln Lys Val Phe Asn Asp Lys Lys Ser
                325                 330                 335

Phe Phe Gln Lys Lys Ala Val Leu Gly Thr Gly Gln Met Leu Tyr Asp
            340                 345                 350

Asn Leu Gly Thr Ser Pro Thr Tyr Ala Asp Leu Ile Lys Arg Ile Lys
        355                 360                 365

Gly Asp Ala Met Lys Gln Ser Trp Lys Ser Leu Gly Asp Thr Lys Gly
    370                 375                 380

Gly Asp Lys Asp Glu Ser Leu Ala Tyr Gln Glu Ala Ser Asn Ala Leu
385                 390                 395                 400

Tyr Ile Glu Gly Tyr Arg Asp Gly Val Pro Glu Met Gln Pro Tyr Leu
                405                 410                 415

Gln Asp Asn Pro Lys Lys Trp Ala Ala Asp Tyr Phe Ala Trp Leu Ser
            420                 425                 430
```

```
Asp Glu Ala Asn Leu Leu Thr Trp Ser Ile Gln Val Ala Ser Lys Met
        435                 440                 445

Phe Asp Asn Val Arg Gln Arg Met Tyr Glu Trp Tyr Val Lys Leu Gln
    450                 455                 460

Val Leu Asp Pro Asp Ser Asn Tyr Gly Gln Arg Phe Met Thr Ile Ala
465                 470                 475                 480

Tyr Ala Ala Leu Leu Gly Val Asn Tyr Ser Lys Ser Arg Trp Ser Asp
                485                 490                 495

Asp Leu Lys Pro Phe Leu Thr Ser Leu Ile Glu Gln Ala Ile Ala Gly
            500                 505                 510

Lys Val Asp Pro Thr Leu Met Asp Gln Ile Gln Gln Gln Ala Ala Leu
        515                 520                 525

Glu Asn Gln Glu Leu Leu Lys Thr Leu Ile Thr Thr Thr Asp Ser Ile
    530                 535                 540

His Asn Leu Val Asp Gly Ile Ala Ala Ala Ile Thr Glu Tyr Gln Leu
545                 550                 555                 560

Lys Lys Gly Asn Gln Pro Leu Ser Arg Ile Ala Gln Asp Pro Glu Leu
                565                 570                 575

Gln Gly Met Ile Gly Gln Arg Leu Asp Gly Gln Gln Tyr Lys Ala Trp
            580                 585                 590

Gly Glu Leu Ser Arg Lys Gly Lys Val Gly Gly Val Leu Thr Val Val
        595                 600                 605

Phe Tyr Gly Ala Ser Ala Gly Tyr Leu Ile Tyr Ser Leu Ala Asp Asn
    610                 615                 620

Pro Gly Arg Pro Leu Thr Pro Lys Glu Ile Ile Glu Lys Ile Asn Leu
625                 630                 635                 640

Gly Leu Leu Ala Leu Ala Thr Leu Val Lys Gly Val Gln Lys Met Met
                645                 650                 655

Ser Ile Gly Val Gly Arg Phe Leu Glu Asn Phe Ser Lys Ala Ala Glu
            660                 665                 670

Gly Gly Ala Phe Arg Ala Phe Ala Gly Asp Ile Ala Thr Trp Phe Lys
        675                 680                 685

Ala Gly Gly Lys Ile Val Pro Glu Gly Lys Leu Gly Lys Ala Phe Val
    690                 695                 700

Thr Ile Phe Gly Glu Ser Ser Ala Glu Phe Met Ala Arg Arg Ile Gly
705                 710                 715                 720

Pro Ala Leu Ala Val Val Gly Met Ile Leu Ser Ser Phe Met Leu Tyr
                725                 730                 735

Asp Ala Ile Lys Ser Gly Ala Val Arg Glu Ile Val Phe Glu Ala Leu
            740                 745                 750

Asn Thr Phe Phe Ala Leu Ala Asp Val Val Phe Ile Gly Leu Glu Leu
        755                 760                 765

Phe Ser Val Gly Trp Ala Gly Pro Val Gly Leu Ala Ile Ala Val Val
    770                 775                 780

Gly Val Ile Val Ile Leu Val Gln Phe Ile Trp Asn Leu Ile Glu Pro
785                 790                 795                 800

Pro Thr Pro Ala Pro Asp Pro Ile Thr Glu Phe Val Asn Gly Pro Met
                805                 810                 815

Val Asn Gln Gly Phe Ala Val Ser Ala
            820                 825
```

<210> SEQ ID NO 65
<211> LENGTH: 764
<212> TYPE: PRT

-continued

<213> ORGANISM: Burkholderia cepacia

<400> SEQUENCE: 65

```
Met Leu Leu Thr Val Gln Arg Ser Ala Ile Arg Leu Ser Gly Ser Ser
1               5                   10                  15

Asp Ser Ala Pro Asp Ser Val Ile Glu Gln Leu Val Asn Leu Leu Pro
            20                  25                  30

Asp Tyr Ser Gly Gly Arg Arg Leu His Ala Leu Leu Val Asn Arg Leu
        35                  40                  45

Lys Gly Ala Leu Pro Gly Asn Tyr Ser Gln Ile Phe Gly Thr Gly Pro
    50                  55                  60

Ser Phe Arg Ser Ile Phe Phe Ala Asp Tyr Gln Pro Asp Pro Leu Leu
65                  70                  75                  80

Pro Leu Met Ser Asp Met Gly Leu Asp Asp Gly Trp Trp Ala Asn Phe
                85                  90                  95

Ser Val Ala Val Leu Cys Gln Ser Ile Gln Asp Leu Gly Ser Arg Ile
            100                 105                 110

Arg Gly Gln Met Arg Ala Asp Lys Ile Asn His Asp Val Ala Ser Phe
        115                 120                 125

Asn Ala Thr Val Arg Gly Arg Cys Ala Arg Pro Tyr Ala Arg Val Leu
    130                 135                 140

Ala Ala Ser Phe Pro Pro Leu Ile Asn Leu Leu Asn Gln Val Asp His
145                 150                 155                 160

Ala Thr Ala Arg Gln Gln Phe His Asp Ala Leu Leu Gly Asn Val Ile
                165                 170                 175

Asn Arg Gln Leu Trp Tyr Gln Ala Gly Met Trp Thr Ser Pro Asp Trp
            180                 185                 190

Glu Met Phe Asn Gln Tyr Ala Lys Tyr Ile Ala Leu Gly Ala Asp Asp
        195                 200                 205

Ala Gln Val Asp Ala Leu Ile Asp Glu Leu Thr Ala Ala Gly Leu Pro
    210                 215                 220

Ile Pro Pro Gln Val Asn Arg Ser Asn Trp Arg Gly Tyr Ala Glu Ala
225                 230                 235                 240

Leu Arg Asp Lys Pro Asp Ile Asp Leu Asp Asp Val Gly Gly Asp Thr
                245                 250                 255

Ala Lys Pro Ile Gln Glu Thr Thr Tyr Leu Pro Ser Tyr Gly Arg Gly
            260                 265                 270

Met Pro Ala Arg Met Pro Asn Gly Asn Cys Tyr Glu Phe Thr Ala Gly
        275                 280                 285

Gly Gln Pro Gly Ser Pro Phe Arg Ala Pro Pro Ser Ser Cys Cys Phe
    290                 295                 300

Thr Gly Asp Thr Glu Val Leu Ser Gly Ala Gly Val Pro Val Pro Leu
305                 310                 315                 320

Asn Gln Val Lys Pro Gly Asp Thr Val Met Thr Arg Asp Gly Ala Ala
                325                 330                 335

Val Val Ala Phe Val Ala Arg Pro Gln Leu Gly Glu Arg Lys Leu Tyr
            340                 345                 350

Arg Ile Asn Gly Gly Gly Pro Val Phe Thr Asp Thr His Pro Phe Leu
        355                 360                 365

Asn Ala Ser Ala Ser Asp Ser Arg Ala Met Ala Pro Ala Ile Leu Ala
    370                 375                 380

Ala Asp Pro Ala His Leu Ala Trp Met Val Pro Thr Leu Ser Glu Asp
385                 390                 395                 400
```

Gly Ile Gly Lys Leu Thr Thr Gly Cys Val Leu Thr Gly Arg Arg Pro
405 410 415

Glu Ser Ser Glu Ser Phe Pro Val Asp Val Thr Thr Val Glu Pro Val
420 425 430

Pro Arg Gly Thr Gly Asp Asp Tyr Leu Tyr Asp Leu Asn Leu Leu Val
435 440 445

Thr Thr Gly Ala Arg Gln Glu Phe Trp Ala Gly Lys Asp Gly Arg Phe
450 455 460

Tyr Leu Val Ser Pro Glu Phe Pro Val Leu Ala Gln Ala Gly Ala Ala
465 470 475 480

Ala Val Ala Val Val Ala Ala Leu Glu Gly Leu Ile Ala Ala Gly Gly
485 490 495

Pro Thr Leu Ser Gly Trp Pro Val Thr Thr Arg Glu Leu Val His Arg
500 505 510

Phe Gly Ala Ala Ile Phe Asp Ala Gly Leu Asp Ala Ala Leu Arg Thr
515 520 525

Val Pro Ser Phe Gly Ser Pro Thr Pro Val Arg Pro Leu Phe Glu Arg
530 535 540

Ile Asp Lys Leu Tyr Arg Asp Leu Gly Ser Val Asp Val Val Gly Ala
545 550 555 560

Ser Ala Ile Ala Ala Phe Phe Asp Gly Phe Met Ser Thr Ile Val Thr
565 570 575

Trp Leu Thr Ala Ser Val Ala Leu Gly Trp Arg Lys Pro Ala Glu Pro
580 585 590

Ser Gly Glu Ile Val Val Val Thr Ile Phe Asp Met Ala Leu Ala Pro
595 600 605

Gly Thr Pro Val Gln Thr Ala Ser Gln Ile Arg Met Glu Val Arg Ala
610 615 620

Gln Gly Gln Ser Glu Ser Ala Ser Ala Met Met Trp Asn Arg Ser Gly
625 630 635 640

Arg Ala Asn Thr Arg Phe His His Tyr Phe Asp Gln Leu Ile His Leu
645 650 655

Asp Arg Ala Lys Leu Gly Ala Thr Gly Gly Leu Thr Phe Ala Val Val
660 665 670

Met Asp Gly Ala Ser Val Pro Ala Leu Ser Gly Ala Ala Pro Leu Val
675 680 685

Ile Gly Asp Arg Ala His Cys Phe Gln Ser Ala Gln Leu Phe Asp Ala
690 695 700

Ala Gly Ala Ala Val Gly Thr Ile Arg Phe Asp Thr Arg Leu Leu Thr
705 710 715 720

Arg Arg Thr Ala Glu Asp Glu Leu Ala His Ser Gly Leu Trp Thr Glu
725 730 735

Glu Ala Ala Leu Ala Tyr Ser Asn Ala Leu Gly Thr Ala Met Ile Ala
740 745 750

Pro Ile Leu Thr Thr Leu Glu Gly Leu Ala Gly Arg
755 760

<210> SEQ ID NO 66
<211> LENGTH: 825
<212> TYPE: PRT
<213> ORGANISM: Burkholderia cepacia

<400> SEQUENCE: 66

Met Phe Leu Thr Arg Val Glu His Ser Leu Ser Asp Cys Lys Cys Ala
1 5 10 15

His Gln Asn Ile Tyr Glu Thr Glu Ile Tyr Asp Gly Thr Ser Trp Val
20 25 30

Ala His Gly Gln Met Val Val Leu Glu Asp Ala Val Thr His Asn Gly
35 40 45

Val His Ala His Asn Ile Gly Tyr Asn Gly Ser Asn His Ser Leu Val
50 55 60

Leu Gln Gly Gly Thr Gly Arg Gln Arg Tyr Asn Ala Arg Leu Asn Leu
65 70 75 80

Thr Glu Cys Gly Ser Ala Phe Val Gly Thr Leu Glu Val Ala Gly Asp
85 90 95

Ala Pro Arg Ala Ile Arg Gly Val Ala Leu Ala Asn Val Phe Asp Thr
100 105 110

Lys Arg Tyr Leu Arg Pro Lys Pro Lys Thr Lys Asp Asp Pro Ala Val
115 120 125

Lys Cys Asp Pro Asn Ala Pro Ser Val Ala Trp Asp Gln Phe Ser Ile
130 135 140

Lys Ala Gln Trp Ile Asp Asn Val Leu Thr Val Thr Tyr Leu Leu Gly
145 150 155 160

His Val Asp Val Ser Asn Arg Val Arg Val Thr Ala Val Asp Arg Gln
165 170 175

Lys Gly Glu Thr Thr Leu Glu Met Val Pro Gln Leu Asp Pro Pro Gly
180 185 190

Pro Gln Asp Ser Phe Val Ile Thr Leu Tyr Ser Gly Asn Arg Thr Phe
195 200 205

Gly Gly Glu Tyr Thr Ser Asp Asp Glu Glu Ala Tyr Cys Trp Phe Gly
210 215 220

Ser Ser Thr Pro Ser Ile Ser Glu Gln Arg Ser Arg Val Phe Ala Glu
225 230 235 240

Val Arg Glu Gly Ala Ala Ala Leu Ala Thr Thr Ala Arg Ile Ser Thr
245 250 255

Pro Leu Glu Gly Asp Ala Ala Thr Arg Thr Leu Gln Asp Leu Asp Asn
260 265 270

Ile Ser Ser Leu Thr Val Val Thr Asp Lys Asp Gly Asn Arg Met Thr
275 280 285

Ile Asp His Ala Gln Thr Thr Cys Gly Gly Tyr Phe Asn Lys Cys Leu
290 295 300

Val Asn Ala Leu Asp Ser Lys Trp Ile Glu Gly Ile Tyr Gly His Ala
305 310 315 320

Tyr Leu Leu Pro Gly Gly Val Gln Lys Val Phe Asn Asp Lys Lys Ser
325 330 335

Phe Phe Gln Lys Lys Ala Val Leu Gly Thr Gly Gln Met Leu Tyr Asp
340 345 350

Asn Leu Gly Thr Ser Pro Thr Tyr Ala Asp Leu Ile Lys Arg Ile Lys
355 360 365

Gly Asp Ala Met Lys Gln Ser Trp Lys Ser Leu Gly Asp Thr Lys Gly
370 375 380

Gly Asp Lys Asp Glu Ser Leu Ala Tyr Gln Glu Ala Ser Asn Ala Leu
385 390 395 400

Tyr Ile Glu Gly Tyr Arg Asp Gly Val Pro Glu Met Gln Pro Tyr Leu
405 410 415

Gln Asp Asn Pro Lys Lys Trp Ala Ala Asp Tyr Phe Ala Trp Leu Ser
420 425 430

-continued

```
Asp Glu Ala Asn Leu Leu Thr Trp Ser Ile Gln Val Ala Ser Lys Met
        435                 440                 445

Phe Asp Asn Val Arg Gln Arg Met Tyr Glu Trp Tyr Val Lys Leu Gln
    450                 455                 460

Val Leu Asp Pro Asp Ser Asn Tyr Gly Gln Arg Phe Met Thr Ile Ala
465                 470                 475                 480

Tyr Ala Ala Leu Leu Gly Val Asn Tyr Ser Lys Ser Arg Trp Ser Asp
                485                 490                 495

Asp Leu Lys Pro Phe Leu Thr Ser Leu Ile Glu Gln Ala Ile Ala Gly
            500                 505                 510

Lys Val Asp Pro Thr Leu Met Asp Gln Ile Gln Gln Gln Ala Ala Leu
        515                 520                 525

Glu Asn Gln Glu Leu Leu Lys Thr Leu Ile Thr Thr Thr Asp Ser Ile
    530                 535                 540

His Asn Leu Val Asp Gly Ile Ala Ala Ala Ile Thr Glu Tyr Gln Leu
545                 550                 555                 560

Lys Lys Gly Asn Gln Pro Leu Ser Arg Ile Ala Gln Asp Pro Glu Leu
                565                 570                 575

Gln Gly Met Ile Gly Gln Arg Leu Asp Gly Gln Gln Tyr Lys Ala Trp
            580                 585                 590

Gly Glu Leu Ser Arg Lys Gly Lys Val Gly Gly Val Leu Thr Val Val
        595                 600                 605

Phe Tyr Gly Ala Ser Ala Gly Tyr Leu Ile Tyr Ser Leu Ala Asp Asn
    610                 615                 620

Pro Gly Arg Pro Leu Thr Pro Lys Glu Ile Ile Glu Lys Ile Asn Leu
625                 630                 635                 640

Gly Leu Leu Ala Leu Ala Thr Leu Val Lys Gly Val Gln Lys Met Met
                645                 650                 655

Ser Ile Gly Val Gly Arg Phe Leu Glu Asn Phe Ser Lys Ala Ala Glu
            660                 665                 670

Gly Gly Ala Phe Arg Ala Phe Ala Gly Asp Ile Ala Thr Trp Phe Lys
        675                 680                 685

Ala Gly Gly Lys Ile Val Pro Glu Gly Lys Leu Gly Lys Ala Phe Val
    690                 695                 700

Thr Ile Phe Gly Glu Ser Ser Ala Glu Phe Met Ala Arg Arg Ile Gly
705                 710                 715                 720

Pro Ala Leu Ala Val Val Gly Met Ile Leu Ser Ser Phe Met Leu Tyr
                725                 730                 735

Asp Ala Ile Lys Ser Gly Ala Val Arg Glu Ile Val Phe Glu Ala Leu
            740                 745                 750

Asn Thr Phe Phe Ala Leu Ala Asp Val Val Phe Ile Gly Leu Glu Leu
        755                 760                 765

Phe Ser Val Gly Trp Ala Gly Pro Val Gly Leu Ala Ile Ala Val Val
    770                 775                 780

Gly Val Ile Val Ile Leu Val Gln Phe Ile Trp Asn Leu Ile Glu Pro
785                 790                 795                 800

Pro Thr Pro Ala Pro Asp Pro Ile Thr Glu Phe Val Asn Gly Pro Met
                805                 810                 815

Val Asn Gln Gly Phe Ala Val Ser Ala
            820                 825
```

<210> SEQ ID NO 67
<211> LENGTH: 387
<212> TYPE: PRT

<213> ORGANISM: Burkholderia cepacia

<400> SEQUENCE: 67

```
Met Ala Pro Ala Ile Leu Ala Ala Asp Pro Ala His Leu Ala Trp Met
1               5                   10                  15

Val Pro Thr Leu Ser Glu Asp Gly Ile Gly Lys Leu Thr Thr Gly Cys
            20                  25                  30

Val Leu Thr Gly Arg Arg Pro Glu Ser Ser Glu Ser Phe Pro Val Asp
        35                  40                  45

Val Thr Thr Val Glu Pro Val Pro Arg Gly Thr Gly Asp Asp Tyr Leu
    50                  55                  60

Tyr Asp Leu Asn Leu Leu Val Thr Thr Gly Ala Arg Gln Glu Phe Trp
65                  70                  75                  80

Ala Gly Lys Asp Gly Arg Phe Tyr Leu Val Ser Pro Glu Phe Pro Val
                85                  90                  95

Leu Ala Gln Ala Gly Ala Ala Ala Val Ala Val Val Ala Ala Leu Glu
            100                 105                 110

Gly Leu Ile Ala Ala Gly Gly Pro Thr Leu Ser Gly Trp Pro Val Thr
        115                 120                 125

Thr Arg Glu Leu Val His Arg Phe Gly Ala Ala Ile Phe Asp Ala Gly
    130                 135                 140

Leu Asp Ala Ala Leu Arg Thr Val Pro Ser Phe Gly Ser Pro Thr Pro
145                 150                 155                 160

Val Arg Pro Leu Phe Glu Arg Ile Asp Lys Leu Tyr Arg Asp Leu Gly
                165                 170                 175

Ser Val Asp Val Val Gly Ala Ser Ala Ile Ala Ala Phe Phe Asp Gly
            180                 185                 190

Phe Met Ser Thr Ile Val Thr Trp Leu Thr Ala Ser Val Ala Leu Gly
        195                 200                 205

Trp Arg Lys Pro Ala Glu Pro Ser Gly Glu Ile Val Val Val Thr Ile
    210                 215                 220

Phe Asp Met Ala Leu Ala Pro Gly Thr Pro Val Gln Thr Ala Ser Gln
225                 230                 235                 240

Ile Arg Met Glu Val Arg Ala Gln Gly Gln Ser Glu Ser Ala Ser Ala
                245                 250                 255

Met Met Trp Asn Arg Ser Gly Arg Ala Asn Thr Arg Phe His His Tyr
            260                 265                 270

Phe Asp Gln Leu Ile His Leu Asp Arg Ala Lys Leu Gly Ala Thr Gly
        275                 280                 285

Gly Leu Thr Phe Ala Val Val Met Asp Gly Ala Ser Val Pro Ala Leu
    290                 295                 300

Ser Gly Ala Ala Pro Leu Val Ile Gly Asp Arg Ala His Cys Phe Gln
305                 310                 315                 320

Ser Ala Gln Leu Phe Asp Ala Ala Gly Ala Ala Val Gly Thr Ile Arg
                325                 330                 335

Phe Asp Thr Arg Leu Leu Thr Arg Arg Thr Ala Glu Asp Glu Leu Ala
            340                 345                 350

His Ser Gly Leu Trp Thr Glu Glu Ala Ala Leu Ala Tyr Ser Asn Ala
        355                 360                 365

Leu Gly Thr Ala Met Ile Ala Pro Ile Leu Thr Thr Leu Glu Gly Leu
    370                 375                 380

Ala Gly Arg
385
```

<210> SEQ ID NO 68
<211> LENGTH: 764
<212> TYPE: PRT
<213> ORGANISM: Burkholderia cepacia

<400> SEQUENCE: 68

```
Met Leu Leu Thr Val Gln Arg Thr Ala Ile Arg Leu Ser Gly Ser Ser
1               5                   10                  15

Asp Ser Ala Pro Asp Ser Val Ile Glu Gln Leu Val Asn Leu Leu Pro
            20                  25                  30

Asp Tyr Ser Gly Gly Arg Arg Leu His Ala Leu Leu Val Asn Arg Leu
        35                  40                  45

Lys Gly Ala Leu Pro Gly Asn Tyr Ser Gln Ile Phe Gly Thr Gly Pro
    50                  55                  60

Ser Phe Arg Ser Ile Phe Phe Ala Asp Tyr Gln Pro Asp Pro Leu Leu
65                  70                  75                  80

Pro Leu Met Ser Asp Met Gly Leu Asp Asp Gly Trp Trp Ala Asn Phe
                85                  90                  95

Ser Val Ala Val Leu Cys Gln Ser Ile Gln Asp Leu Gly Ser Arg Ile
            100                 105                 110

Arg Gly Gln Met Arg Ala Asp Lys Ile Asn His Asp Val Ala Ser Phe
        115                 120                 125

Asn Ala Thr Val Arg Gly Arg Cys Ala Arg Pro Tyr Ala Arg Val Leu
    130                 135                 140

Ala Ala Ser Phe Pro Pro Leu Ile Asn Leu Leu Asn Gln Val Asp His
145                 150                 155                 160

Ala Thr Ala Arg Gln Gln Phe His Asp Ala Leu Leu Gly Asn Val Ile
                165                 170                 175

Asn Arg Gln Leu Trp Tyr Gln Ala Gly Met Trp Thr Ser Pro Asp Trp
            180                 185                 190

Glu Met Phe Asn Gln Tyr Ala Lys Tyr Ile Ala Leu Gly Ala Asp Asp
        195                 200                 205

Ala Gln Val Asp Ala Leu Ile Asp Glu Leu Thr Ala Ala Gly Leu Pro
    210                 215                 220

Ile Pro Pro Gln Val Asn Arg Ser Asn Trp Arg Gly Tyr Ala Glu Ala
225                 230                 235                 240

Leu Arg Asp Lys Pro Asp Ile Asp Leu Asp Asp Val Gly Gly Asp Thr
                245                 250                 255

Ala Lys Pro Ile Gln Glu Thr Thr Tyr Leu Pro Ser Tyr Gly Arg Gly
            260                 265                 270

Met Pro Ala Arg Met Pro Asn Gly Asn Cys Tyr Glu Phe Thr Ala Gly
        275                 280                 285

Gly Gln Pro Gly Ser Pro Phe Arg Ala Pro Pro Ser Ser Cys Cys Leu
    290                 295                 300

Thr Gly Asp Thr Glu Val Leu Ser Gly Ala Gly Val Pro Val Pro Leu
305                 310                 315                 320

Asn Gln Val Lys Pro Gly Asp Thr Val Met Thr Arg Asp Gly Ala Ala
                325                 330                 335

Val Val Ala Phe Val Ala Arg Pro Gln Leu Gly Glu Arg Lys Leu Tyr
            340                 345                 350

Arg Ile Asn Gly Gly Gly Pro Val Phe Thr Asp Thr His Pro Phe Leu
        355                 360                 365

Asn Ala Ser Ala Ser Asp Ser Arg Ala Thr Ala Pro Ala Ile Leu Ala
    370                 375                 380
```

```
Ala Asp Pro Ser His Leu Ala Trp Met Val Pro Thr Leu Ser Glu Asp
385                 390                 395                 400

Gly Ile Gly Lys Leu Thr Thr Gly Cys Val Leu Thr Gly Arg Arg Pro
                405                 410                 415

Glu Ser Ser Glu Ser Phe Pro Val Asp Val Thr Thr Val Glu Pro Val
            420                 425                 430

Pro Arg Gly Thr Gly Asp Asp Tyr Leu Tyr Asp Leu Asn Leu Leu Val
        435                 440                 445

Thr Thr Gly Ala Arg Gln Glu Phe Trp Ala Gly Lys Asp Gly Arg Phe
    450                 455                 460

Tyr Leu Val Ser Pro Glu Phe Pro Val Leu Ala Gln Ala Gly Ala Ala
465                 470                 475                 480

Ala Val Ala Val Val Ala Ala Leu Glu Gly Leu Ile Ala Ala Gly Gly
                485                 490                 495

Pro Thr Leu Ser Gly Trp Pro Val Thr Thr Arg Glu Leu Val His Arg
            500                 505                 510

Phe Gly Ala Ala Ile Phe Asp Ala Gly Leu Asp Ala Ala Leu Arg Thr
        515                 520                 525

Val Pro Ser Phe Gly Ser Pro Thr Pro Val Arg Pro Leu Phe Glu Arg
    530                 535                 540

Ile Asp Lys Leu Tyr Arg Asp Leu Gly Ser Val Asp Val Val Gly Ala
545                 550                 555                 560

Ser Ala Ile Ala Ala Phe Phe Asp Gly Phe Met Ser Thr Ile Val Thr
                565                 570                 575

Trp Leu Thr Ala Ser Val Ala Leu Gly Trp Arg Lys Pro Ala Glu Pro
            580                 585                 590

Ser Gly Glu Ile Val Val Val Thr Ile Phe Asp Met Ala Leu Ala Pro
        595                 600                 605

Gly Thr Pro Val Gln Thr Ala Ser Gln Ile Arg Met Glu Val Arg Ala
    610                 615                 620

Gln Gly Gln Ser Glu Ser Ala Ser Thr Thr Met Trp Asn Arg Ser Gly
625                 630                 635                 640

Arg Ala Asn Thr Arg Phe His His Tyr Phe Asp Gln Leu Ile His Leu
                645                 650                 655

Asp Arg Ala Lys Leu Gly Ala Thr Gly Gly Leu Thr Phe Ala Val Val
            660                 665                 670

Met Asp Gly Ala Ser Val Pro Ala Leu Ser Gly Ala Ala Pro Leu Val
        675                 680                 685

Ile Gly Asp Arg Ala His Cys Phe Gln Ser Ala Gln Leu Phe Asp Ala
    690                 695                 700

Ala Gly Thr Ala Val Gly Thr Ile Arg Phe Asp Thr Arg Leu Leu Thr
705                 710                 715                 720

Arg Arg Thr Ala Glu Asp Glu Leu Ala His Ser Gly Leu Trp Thr Glu
                725                 730                 735

Glu Ala Ala Leu Ala Tyr Ser Asn Ala Leu Gly Thr Ala Met Val Ala
            740                 745                 750

Pro Ile Leu Thr Thr Leu Glu Gly Leu Ala Gly Arg
        755                 760
```

<210> SEQ ID NO 69
<211> LENGTH: 340
<212> TYPE: PRT
<213> ORGANISM: Burkholderia sp.

<400> SEQUENCE: 69

Met Met Lys Asn Leu Pro Ala Val Glu Leu Pro Glu Leu Phe Ala Lys
1 5 10 15

Phe Arg Pro Gly Glu Arg Arg Asp Ile Val Ser His Phe Thr Pro Thr
20 25 30

Ile Ala Gln Gln Ala Gly Ile Thr Pro His Leu Ser Glu Pro Ile Pro
35 40 45

Val Glu Leu Ile Asp Ala Thr Thr Pro Tyr Leu Leu Val Asp Glu Ser
50 55 60

Asn Arg Ile Leu Leu Ala Asn Asp Arg Gly Val Gly Ala Trp Gln Trp
65 70 75 80

Ala Phe Val Gly Ser Tyr Ser Asp Tyr Ala Ser Tyr Val Leu Gly Thr
85 90 95

Ser Phe Gly Ser Asp Pro Ala Leu Asn Pro Ala Pro Leu Tyr Leu Gly
100 105 110

Pro Pro Gln Asn Thr Lys Tyr Leu Gln Ser Asn Gly Ser Ser Ser Ser
115 120 125

Trp Asp Trp Val Phe Trp Ala Asp Ser Ser Tyr Lys Tyr Pro Thr Val
130 135 140

Ser Leu Lys Thr Gln Ala Ile Ser Ser Gln Thr Phe Lys Leu Ile Tyr
145 150 155 160

Lys Asn Asn Ser Thr Glu Met Gly Leu Cys Ala Asp Ser Gly Ser Trp
165 170 175

Asn Trp Val Tyr Val Gly Asn Thr Ser Ser Tyr Thr Pro Leu Thr Leu
180 185 190

Thr Ala Arg Lys Phe Phe Leu Gly Tyr Asn Asp Leu Lys Lys Leu Phe
195 200 205

Ala Ala Thr Trp Pro Asn Ala Ser Ile Thr Asp Trp Ser Phe Arg Val
210 215 220

Gly Asp Lys Asp Tyr Glu Leu Leu His Gln Ser Lys Ala Gln Gln Ile
225 230 235 240

Tyr Asn Asp Ser Gly Leu Ser Lys Tyr Lys Trp Val Glu Glu Val Phe
245 250 255

Asp Cys Asp Asp Phe Ser Tyr Ala Tyr Lys Ala Gln Ala Ser Arg Val
260 265 270

Ala Tyr Glu Asp Tyr Lys Ala Thr Gly Asn Ala Val Gln Arg Ser Tyr
275 280 285

Ala Ser Gly Val Val Phe Gly Arg Lys Pro Asp Gly Thr Ala His Ala
290 295 300

Val Asn Val Phe Val Asp Tyr Thr Cys Thr Val Lys Ile Leu Glu Pro
305 310 315 320

Gln Asn Gly Ser Ile Ile Asp Gly Lys Asp Trp Ala Tyr Thr Pro Tyr
325 330 335

Phe Ile Leu Phe
340

<210> SEQ ID NO 70
<211> LENGTH: 120
<212> TYPE: PRT
<213> ORGANISM: Burkholderia ambifaria

<400> SEQUENCE: 70

Met Ser Ala Arg Ser Thr Val Val Lys Leu Gln Asn Asn Ser Gly Asn
1 5 10 15

```
Thr Leu Phe Leu Asp Pro Ala Ser Ile Asn Leu Ile His Gly Glu Trp
            20                  25                  30

Val Thr Tyr Pro Pro Glu Lys Ile Pro Asp Gly Gln Thr Gly Gln Trp
        35                  40                  45

Glu Ser Asp Ser Asp Gly Phe Met Thr Gly Thr Glu Gly Gln Leu Gln
    50                  55                  60

Tyr Gln Phe Ala Asp Gly Gly Gly Ile Glu Asn Val Arg Leu Tyr Trp
65                  70                  75                  80

Asp Asn Pro Tyr Ile Gly Asn Asn Gly Tyr Ser Ile Thr Val Ser Ala
                85                  90                  95

Gly Gly Tyr Lys Val Gly Tyr Asp Gly Gly Ser Gly Asp Asn Ala Thr
            100                 105                 110

Val Asn Phe Tyr Ile Lys Gln Gly
        115                 120


<210> SEQ ID NO 71
<211> LENGTH: 120
<212> TYPE: PRT
<213> ORGANISM: Burkholderia pyrrocinia

<400> SEQUENCE: 71

Met Ser Ala Arg Ser Thr Val Val Lys Leu Gln Asn Asn Ser Gly Asn
1               5                   10                  15

Thr Leu Phe Leu Asp Pro Ala Ser Ile Asn Leu Leu His Gly Glu Trp
            20                  25                  30

Val Thr Tyr Pro Pro Glu Lys Ile Pro Asp Gly Gln Thr Gly Gln Trp
        35                  40                  45

Glu Ser Asp Ser Asp Gly Phe Met Thr Gly Thr Glu Gly Gln Leu Gln
    50                  55                  60

Tyr Gln Phe Ala Asp Gly Gly Gly Ile Glu Asn Val Arg Leu Tyr Trp
65                  70                  75                  80

Asp Asn Pro Tyr Val Gly Asn Asn Gly Tyr Ser Ile Thr Val Ser Ala
                85                  90                  95

Ala Gly Tyr Lys Val Gly Tyr Asp Gly Gly Ser Gly Asp Asn Ala Thr
            100                 105                 110

Val Asn Phe Tyr Ile Lys Lys Gly
        115                 120


<210> SEQ ID NO 72
<211> LENGTH: 120
<212> TYPE: PRT
<213> ORGANISM: Burkholderia glumae

<400> SEQUENCE: 72

Met Ser Ser Arg Ser Thr Val Val Lys Leu Gln Asn Asn Ser Gly His
1               5                   10                  15

Thr Leu Tyr Leu Asp Ser Thr Ser Ile Gln Leu Ala His Gly Glu Trp
            20                  25                  30

Val Thr Tyr Pro Pro Glu Lys Ile Pro Asn Gly Gln Thr Gly Gln Trp
        35                  40                  45

Gln Thr Asp Ser Asp Gly Phe Met Thr Gly Thr Glu Gly Lys Leu Gln
    50                  55                  60

Tyr Gln Phe Ala Asp Asn Asp Gly Ile Glu Asn Val Arg Ile Tyr Trp
65                  70                  75                  80

Asp Asn Pro Tyr Ile Gly Asn Asn Gly Tyr Ser Ile Thr Val Ser Ala
                85                  90                  95
```

```
Ala Gly Tyr Lys Val Gly Tyr Asp Gly Gly Ser Gly Asp Asn Ala Thr
            100                 105                 110

Val Asp Phe Tyr Ile Lys Gln Glu
        115                 120


<210> SEQ ID NO 73
<211> LENGTH: 120
<212> TYPE: PRT
<213> ORGANISM: Burkholderia anthina

<400> SEQUENCE: 73

Met Ser Ala Arg Ser Thr Val Val Lys Leu Gln Asn Asn Ser Gly Ser
1               5                   10                  15

Thr Leu Phe Leu Asp Ser Ala Ser Ile Asn Leu Leu His Gly Glu Trp
            20                  25                  30

Val Thr Tyr Pro Pro Glu Lys Ile Pro Asn Gly Gln Thr Gly Glu Trp
        35                  40                  45

Glu Ser Asp Ser Asp Gly Phe Met Thr Gly Thr Glu Gly Lys Leu Gln
    50                  55                  60

Tyr Gln Phe Ala Asp Gly Gly Gly Ile Glu Asn Leu Arg Ile Tyr Trp
65                  70                  75                  80

Asp Asn Pro Tyr Tyr Gly Gly Asn Gly Tyr Ser Ile Thr Val Ser Ala
                85                  90                  95

Ala Gly Tyr Lys Val Gly Tyr Asp Gly Gly Ser Gly Asp Asn Ala Thr
            100                 105                 110

Val Thr Phe Tyr Ile Lys Gln Ala
        115                 120


<210> SEQ ID NO 74
<211> LENGTH: 120
<212> TYPE: PRT
<213> ORGANISM: Burkholderia anthina

<400> SEQUENCE: 74

Met Ser Ala Arg Ser Thr Val Val Lys Leu Gln Asn Asn Ser Gly Ser
1               5                   10                  15

Thr Leu Phe Leu Asp Ser Ala Ser Ile Asn Leu Leu His Gly Glu Trp
            20                  25                  30

Val Thr Tyr Pro Pro Glu Lys Ile Pro Asn Gly Gln Met Gly Glu Trp
        35                  40                  45

Glu Ser Asp Ser Asp Gly Phe Thr Thr Gly Thr Glu Gly Lys Leu Gln
    50                  55                  60

Tyr Gln Phe Ala Asp Gly Gly Gly Ile Glu Asn Leu Arg Ile Tyr Trp
65                  70                  75                  80

Asp Asn Pro Tyr Tyr Gly Gly Asn Gly Tyr Ser Ile Thr Val Ser Ala
                85                  90                  95

Ala Gly Tyr Lys Val Gly Tyr Asp Gly Gly Ser Gly Asp Asn Ala Thr
            100                 105                 110

Val Thr Phe Tyr Ile Lys Gln Ala
        115                 120


<210> SEQ ID NO 75
<211> LENGTH: 122
<212> TYPE: PRT
<213> ORGANISM: Burkholderia multivorans

<400> SEQUENCE: 75

Met Ser Ala Arg Ser Val Ala Val Thr Phe Phe Asn Leu Thr Ser His
```

```
1               5                   10                  15

Asp Leu Ile Leu Asp Thr Ser Ser Val Gln Leu Gln His Gly Glu Trp
            20                  25                  30

Lys Arg Tyr Pro Pro Ser Ile Ile Pro Ser Leu Gln Tyr Gly Glu Trp
        35                  40                  45

Glu Ser Asp Ser Asp Gly Ile Tyr Thr Gly Thr Gln Gly Ser Leu Gln
    50                  55                  60

Tyr Gln Phe Gln Tyr Asn Gly Ile Gln Asn Ile Pro Ile Ser Trp Asp
65                  70                  75                  80

Asp Pro Tyr Tyr Gly Gly Asn Ser Tyr Gly Ile Ser Cys Ser Ser Ser
                85                  90                  95

Asp Phe Lys Thr Arg Tyr Ala Gly Gly Asp Gly Asp Asn Ala Val Val
            100                 105                 110

Gln Phe Phe Ile Asp Gln Lys Gly Ser Asp
        115                 120


<210> SEQ ID NO 76
<211> LENGTH: 139
<212> TYPE: PRT
<213> ORGANISM: Sinorhizobium medicae

<400> SEQUENCE: 76

Met Ser Asp Ala Ile Ala Gly Ser Glu Pro Thr Lys Ser Arg Gly Pro
1               5                   10                  15

Ile Glu Arg Ser Ala Arg Ser Val Val Ile Gln Leu Asn Asn Gln Thr
            20                  25                  30

Ser Ala Ile Leu Gln Leu Gln Gln Asp Thr Leu Ser Leu Glu His Gly
        35                  40                  45

Glu Trp Val Ile Tyr Pro Pro Ala Asn Ile Tyr Pro Gly Gln Leu Val
    50                  55                  60

Ser Trp Gln Thr Asp Ser Asn Gly Phe Met Thr Gly Thr Glu Gly Arg
65                  70                  75                  80

Cys Thr Tyr Gln Phe Ile Ala Gly Ser Thr Ile Ala Asn Val Lys Leu
                85                  90                  95

His Trp Asp Asn Pro Tyr Val Gly Gly Asn Ser Tyr Ser Ile Val Val
            100                 105                 110

Thr Pro Pro Pro Tyr Ser Gly Asp Tyr Gly Gly Gly Ser Gly Asp Asn
        115                 120                 125

Ser Thr Val Thr Tyr Lys Val Tyr Arg Val Ala
    130                 135


<210> SEQ ID NO 77
<211> LENGTH: 119
<212> TYPE: PRT
<213> ORGANISM: Burkholderia ambifaria

<400> SEQUENCE: 77

Met Ala Ala Arg Ser Val Val Ala Lys Phe Ser Asn Asn Thr Lys Phe
1               5                   10                  15

Asp Leu Met Leu Gly Asp Ser Glu Leu Trp His Gly His Trp Val Thr
            20                  25                  30

Ser Pro Pro Ser Ser Ile Ala Pro Gly Ala Glu Gly Gln Trp Glu Thr
        35                  40                  45

Asp Ser Asp Asp Tyr Glu Ser Gly Thr Ala Gly Asp Leu Gln Tyr Gln
    50                  55                  60

Phe Thr Asn Glu Glu Gly Thr Gln Thr Val Arg Val Ser Trp Ala Val
```

```
65                  70                  75                  80

Pro Tyr Leu Gly Ser Asn Asn Phe Glu Val Tyr Cys Glu Ala Ala Gly
                85                  90                  95

Val Arg Pro Gly Tyr Thr Gly Gly Gly Gln Asp Thr Asn Ala Thr Val
            100                 105                 110

Asn Tyr Tyr Leu Asn Gln Ala
        115


<210> SEQ ID NO 78
<211> LENGTH: 121
<212> TYPE: PRT
<213> ORGANISM: Burkholderia cenocepacia

<400> SEQUENCE: 78

Met Ala Asp Ala Ala Arg Ser Val Ile Ala Lys Leu Thr Asn Asn Thr
1               5                   10                  15

Lys Phe Val Leu Thr Leu Asp Lys Ser Ser Val Gln Leu Asp His Gly
            20                  25                  30

Lys Trp Ala Thr Ser Pro Pro Asp Gln Ile Ser Pro Gly Asp Val Gly
        35                  40                  45

Gln Trp Glu Ser Glu Ser Asp Ser Phe Asn Thr Gly Thr Glu Gly Arg
    50                  55                  60

Leu Arg Tyr Gln Phe Ser Asp Gln Ser Thr Tyr Asn Val Asp Val Tyr
65                  70                  75                  80

Trp Ser Asp Pro Phe Phe Ser Gly Ser Asp Tyr Ser Ile Asp Cys Asn
                85                  90                  95

Ala Asp Gly Phe Arg Val Gly His Thr Gly Gly Asp Gly Ser Asn Ala
            100                 105                 110

Thr Val Asp Tyr Tyr Ile Asn Glu Gly
        115                 120


<210> SEQ ID NO 79
<211> LENGTH: 132
<212> TYPE: PRT
<213> ORGANISM: Pseudomonas syringae

<400> SEQUENCE: 79

Met Ser Asp Ala Ala Arg Ser Thr Val Ile Lys Val Thr Asn Asn Ser
1               5                   10                  15

Lys Tyr Asn Leu Arg Leu Ile Thr Ser Ser Gln Lys Leu Pro His Gly
            20                  25                  30

Glu Trp Ile Thr Tyr Pro Pro Asp Arg Ile Thr Lys Asn Ser Thr Ser
        35                  40                  45

Asn Gly Pro Gly His Ala Ser Trp Glu Thr Asp Ser Asp Gly Phe Met
    50                  55                  60

Thr Gly Thr Glu Gly Glu Cys Ser Tyr Ser Phe Thr Asp Asp Asp Glu
65                  70                  75                  80

Ile Tyr Asp Ile Asn Ile Lys Trp Asp Asn Pro Phe Ser Gly Gly Asn
                85                  90                  95

Thr Tyr Ser Ile His Pro Asp Asn Asp Leu Val Arg Cys Thr Tyr Thr
            100                 105                 110

Ala Asp Lys Gly Asn Asn Ala Thr Val Thr Phe Thr Ile Glu Asn Gly
        115                 120                 125

Ser Asn His Asn
    130
```

<210> SEQ ID NO 80
<211> LENGTH: 127
<212> TYPE: PRT
<213> ORGANISM: Pseudomonas lini

<400> SEQUENCE: 80

```
Met Ala Lys Arg Ser Val Asp Val Tyr Phe Glu Asn Tyr Leu Asp Ser
1               5                   10                  15

Thr Leu Ser Leu Thr Gln Asn Ser Leu Lys Leu Asp His Gly Glu Trp
            20                  25                  30

Asp Thr Tyr Pro Pro Gln Lys Ile Leu Lys Pro Ser Ser Asn Val Ser
        35                  40                  45

Gly Lys Gly Tyr Trp Lys Thr Glu Ser Asp Gly Phe Ala Thr Gly Thr
    50                  55                  60

Glu Ala Leu Cys Ser Tyr Ala Phe Tyr Asp Phe Val Thr Glu Glu Ile
65                  70                  75                  80

Cys Asn Ile Asn Ile His Trp Asp Asp Pro Tyr Val Gly Ser Asn Ser
                85                  90                  95

Tyr Glu Ile Thr Thr Asp Ser Asp Asn Val Lys Val Ser Tyr Ser Gly
            100                 105                 110

Gly Asp Gly Asp Asn Ala Thr Val Thr Phe Arg Ala Glu Lys Arg
        115                 120                 125
```

<210> SEQ ID NO 81
<211> LENGTH: 134
<212> TYPE: PRT
<213> ORGANISM: Aquimarina muelleri

<400> SEQUENCE: 81

```
Met Ser Ala Arg Ser Thr Thr Val Lys Leu Gln Asn Thr Thr Ser Asp
1               5                   10                  15

Leu Ile Lys Leu Thr Asp Ala Ser Leu Ser His Gly Val Trp Ser Ser
            20                  25                  30

Asn Gln Tyr Pro Pro Ser Thr Ile Ser Ala Asn Ser Asp Gly Ser Trp
        35                  40                  45

Met Ser Glu Ser Asp Gly Phe Met Thr Gly Thr Glu Gly Thr Val Thr
    50                  55                  60

Tyr Gln Leu Pro Asn Gly Ile Gly Ser Ile Val Ile Thr Trp Asp Asn
65                  70                  75                  80

Pro Tyr Val Gly Ser Asn Ser Tyr Ser Met Lys Ala Pro Ala Gly Phe
                85                  90                  95

Glu Ile Asn Lys Ser Gly Gly Ser Gly Asp Asn Ala Val Val Thr Phe
            100                 105                 110

Thr Leu Ser Val Ser Lys Val Lys Gln Thr Lys Ser Phe Glu Glu Ala
        115                 120                 125

Val Gly Ala Phe Ala Asn
    130
```

<210> SEQ ID NO 82
<211> LENGTH: 118
<212> TYPE: PRT
<213> ORGANISM: Nocardia gamkensis

<400> SEQUENCE: 82

```
Met Ala Ala Arg Ser Tyr Trp Val Arg Val Tyr Asn Tyr Thr Gly Thr
1               5                   10                  15

Asp Leu Thr Leu Thr Asn Lys Ala Leu Gln His Gly Val Trp Ser Asn
            20                  25                  30
```

-continued

```
Asn Gly Gly Ala Thr Pro Pro Asp Val Ile Pro Glu Gly Arg Arg Ala
        35                  40                  45

Glu Trp Gly Ser Glu Ser Asp Gly Leu Ala Thr Gly Thr Glu Gly Glu
    50                  55                  60

Val Val Tyr Ala Ser Ala Ala Gly Glu Phe Lys Val Tyr Trp Asp Asn
65                  70                  75                  80

Pro Tyr Val Gly Ser Asp Gln Thr Ser Val Arg Thr Pro Thr Arg Phe
                85                  90                  95

Ser Ser Val Lys Glu Asp Ser Arg Gly Asp Asn Ala Thr Leu Lys Val
            100                 105                 110

Ala Leu Val Gln Glu Glu
        115


<210> SEQ ID NO 83
<211> LENGTH: 5
<212> TYPE: PRT
<213> ORGANISM: Unknown
<220> FEATURE:
<223> OTHER INFORMATION: Synthetic

<400> SEQUENCE: 83

Glu Glu Lys Lys Asn
1               5


<210> SEQ ID NO 84
<211> LENGTH: 16
<212> TYPE: DNA
<213> ORGANISM: Artificial Sequence
<220> FEATURE:
<223> OTHER INFORMATION: synthetic

<400> SEQUENCE: 84

taccttgtta cgactt                                                      16


<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85

agagtttgat cmtggctcag                                                  20
```